US006491933B2

(12) United States Patent
Lorenzi et al.

(10) Patent No.: US 6,491,933 B2
(45) Date of Patent: *Dec. 10, 2002

(54) PERSONAL CARE ARTICLES COMPRISING HOTMELT COMPOSITIONS

(75) Inventors: Marc Paul Lorenzi, Egham (GB); Edward Dewey Smith, III, Mason, OH (US); Nicola Jacqueline Phipps, Bracknell (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/785,882

(22) Filed: Feb. 16, 2001

(65) Prior Publication Data

US 2001/0018068 A1 Aug. 30, 2001

Related U.S. Application Data

(63) Continuation-in-part of application No. 09/443,741, filed on Nov. 19, 1999, now Pat. No. 6,217,889
(60) Provisional application No. 60/146,747, filed on Aug. 2, 1999.

(51) Int. Cl.$^7$ .......................... A01N 25/34; A61K 6/00; A61K 7/00
(52) U.S. Cl. ........................................ 424/401; 402/404
(58) Field of Search .................................. 424/401, 402

(56) References Cited

U.S. PATENT DOCUMENTS

| | | | | |
|---|---|---|---|---|
| 3,283,357 A | 11/1966 | Decker et al. | ................. | 15/506 |
| 3,537,121 A | 11/1970 | McAvoy | ................... | 15/230.12 |
| 3,581,447 A | 6/1971 | Falivene | ...................... | 51/400 |
| 3,597,299 A | 8/1971 | Thomas et al. | ............... | 161/57 |
| 3,896,807 A | 7/1975 | Buchalter | .................... | 128/261 |
| 3,910,284 A | 10/1975 | Orentreich | ................. | 128/355 |
| 4,189,395 A | 2/1980 | Bland | .......................... | 252/91 |
| 4,287,633 A | 9/1981 | Gropper | ...................... | 15/209 |
| 4,303,543 A | 12/1981 | Mansy | ....................... | 252/117 |
| 4,515,703 A | 5/1985 | Haq | ............................ | 252/92 |
| 4,559,157 A | 12/1985 | Smith et al. | .................. | 252/90 |
| 4,569,343 A | 2/1986 | Kimura et al. | .............. | 128/155 |
| 4,600,620 A | 7/1986 | Lloyd et al. | ................ | 428/195 |
| 4,603,069 A | 7/1986 | Haq et al. | ..................... | 428/76 |
| 4,665,580 A | 5/1987 | Morris | ........................ | 15/118 |
| 4,674,237 A | 6/1987 | Sullivan | ....................... | 51/391 |
| 4,690,821 A | 9/1987 | Smith et al. | ................. | 424/401 |
| 4,735,739 A | 4/1988 | Floyd et al. | .................... | 252/91 |
| 4,758,467 A | 7/1988 | Lempiere | ...................... | 428/290 |
| 4,769,022 A | 9/1988 | Chang et al. | ............... | 604/368 |
| 4,806,572 A | 2/1989 | Kellett | ........................ | 521/112 |
| 4,820,435 A | 4/1989 | Zafiroglu | ..................... | 252/90 |
| 4,891,227 A | 1/1990 | Thaman et al. | ............. | 424/443 |
| 4,931,201 A | 6/1990 | Julemont | ...................... | 252/91 |
| 4,948,585 A | 8/1990 | Schlein | ........................ | 424/404 |
| 5,139,841 A | 8/1992 | Makoui et al. | ............. | 428/109 |
| 5,156,843 A | 10/1992 | Leong et al. | ............... | 424/411 |

(List continued on next page.)

FOREIGN PATENT DOCUMENTS

| | | | | |
|---|---|---|---|---|
| BE | 855362 | 10/1977 | | |
| CA | 810361 | 4/1969 | ................. | 15/121 |
| CN | 1050066 | 3/1991 | .......... | D21H/25/06 |
| EP | 0 211 664 | 2/1987 | ........... | A47L/13/17 |
| EP | 0 186 208 B1 | 5/1990 | ........... | C11D/17/04 |
| EP | 0 161 911 B1 | 8/1990 | ........... | C11D/17/04 |
| EP | 0 353 013 B1 | 9/1993 | ........... | A47L/13/17 |
| EP | 0 604 731 | 7/1994 | ........... | B32B/31/00 |
| EP | 0 421 163 B1 | 11/1994 | ........... | C11D/17/04 |
| EP | 0 353 014 B1 | 1/1996 | ........... | A47L/13/17 |
| EP | 0 750 062 | 12/1996 | ............ | D04H/1/40 |
| EP | 0 836 842 | 5/1998 | ........... | A61F/13/15 |
| EP | 0 864 418 | 9/1998 | ........... | B32B/29/00 |
| EP | 0 870 496 | 10/1998 | ............ | A61K/7/50 |
| JP | 06-017361 | 1/1994 | ............ | D04H/1/54 |
| WO | WO 98/27257 | 6/1998 | ............ | D04H/1/00 |
| WO | WO 99/21532 A | 5/1999 | | |
| WO | WO 99/37200 A | 7/1999 | | |

Primary Examiner—Thurman K. Page
Assistant Examiner—S. Howard
(74) Attorney, Agent, or Firm—Marianne Dressman; Dara M. Kendall; Tara M. Rosnell

(57) ABSTRACT

The present invention relates to a substantially dry, disposable personal care article suitable for cleansing, said article comprising:

a) a water insoluble substrate comprising a creped nonwoven layer; and b) a cleansing component disposed adjacent to said creped nonwoven layer, wherein said component comprises from about 10% to about 1000%, by weight of the water insoluble substrate, of a lathering surfactant and wherein the cleansing component exhibits a log [(η @ 25° C.)/(η @ 200° C.)] greater than about 0.45.

Additionally, the present invention relates to a similar article that is characterized by a cleansing component that exhibits a complex viscosity measured under an oscillation stress of 1 Pa of greater than about 100 Pa·s. at 25° C. The present invention further relates to a substantially dry, disposable personal care article suitable for conditioning wherein the above-described article comprises a therapeutic benefit component, disposed adjacent to said water insoluble substrate, wherein said component comprises from about 10% to about 1000%, by weight of the water insoluble substrate, of a therapeutic benefit component in addition to or in lieu of the cleansing component.

These articles have been found to be particularly useful for personal cleansing applications, namely for the skin and hair. Thus, the present invention further relates to methods of cleansing and conditioning the skin and hair utilizing the articles of the present invention.

20 Claims, No Drawings

U.S. PATENT DOCUMENTS

| | | | |
|---|---|---|---|
| 5,302,446 A | 4/1994 | Horn | 428/286 |
| 5,412,830 A | 5/1995 | Girardot et al. | 15/118 |
| 5,507,968 A | 4/1996 | Palaikis | 252/90 |
| 5,538,732 A | 7/1996 | Smith et al. | 424/402 |
| 5,605,749 A | 2/1997 | Pike et al. | 442/60 |
| 5,698,475 A | 12/1997 | Vlasblom | 442/59 |
| 5,702,992 A | 12/1997 | Martin et al. | 442/123 |
| 5,756,112 A | 5/1998 | Mackey | 424/402 |
| 5,763,332 A | 6/1998 | Gordon et al. | 442/84 |
| 6,217,889 B1 * | 4/2001 | Lorenzi et al. | 424/401 |

* cited by examiner

PERSONAL CARE ARTICLES COMPRISING HOTMELT COMPOSITIONS

CROSS REFERENCE TO RELATED APPLICATION

This application claims the benefit of U.S. provisional patent application Serial No. 60/146,747, filed on Aug. 2, 1999 in the names of Lorenzi et al. and is a continuation-in-part of U.S. patent application Ser. No. 09/443,741, filed on Nov. 19, 1999, now U.S. Pat. No. 6,217,889, in the names of Lorenzi et al.

TECHNICAL FIELD

The present invention relates to disposable, personal care articles suitable for cleansing and/or therapeutically treating the skin, hair and any other sites in need of such treatment. These articles comprise a water insoluble substrate comprising a first creped nonwoven layer; and a cleansing component disposed adjacent to the water insoluble substrate, wherein the cleansing component comprises from about 10% to about 1000%, by weight of the water insoluble substrate, of a lathering surfactant and wherein the cleansing component exhibits a log $[(\eta\ @\ 25°\ C.)/(\eta\ @\ 200°\ C.)]$ greater than about 0.45. In another embodiment, the cleansing component additionally exhibits a complex viscosity measured under an oscillation stress of 1 Pa of greater than about 100 Pa·s at 25° C. The articles may optionally include a therapeutic benefit component. Consumers use the articles by wetting them with water and rubbing them on the area to be cleansed and/or therapeutically treated (e.g., conditioned).

The invention also encompasses methods for cleansing and/or conditioning the skin and hair using the articles of the present invention.

BACKGROUND OF THE INVENTION

Personal care products, particularly cleansing and conditioning products, have traditionally been marketed in a variety of forms such as bar soaps, creams, lotions, and gels. Typically, these products have attempted to satisfy a number of criteria to be acceptable to consumers. These criteria include cleansing effectiveness, skin feel, mildness to skin, hair, and ocular mucosae, and lather volume. Ideal personal cleansers should gently cleanse the skin or hair, cause little or no irritation, and should not leave the skin or hair with a heavy buildup or overly dry when used frequently.

It is also highly desirable to deliver such cleansing and conditioning benefits from a disposable product. Disposable products are convenient because they obviate the need to carry or store cumbersome bottles, bars, jars, tubes, and other forms of clutter including cleansing products and other products capable of providing therapeutic or aesthetic benefits. Disposable products are also a more sanitary alternative to the use of a sponge, washcloth, or other cleansing implement intended for extensive reuse, because such implements can develop bacterial growth, unpleasant odors, and other undesirable characteristics related to repeated use.

The articles of the present invention surprisingly provide effective cleansing and/or therapeutic benefits to the skin and hair in a convenient, inexpensive, and sanitary manner. The present invention provides the convenience of not needing to carry, store, or use a separate implement (such as a washcloth or sponge), a cleanser and optionally a therapeutic benefit product. These articles are convenient to use because they are in the form of either a single, disposable personal care article or multiple disposable articles useful for cleansing as well as application of a therapeutic or aesthetic benefit agent. Moreover, these articles are suitable for use within or in conjunction with another personal care implement that is designed for more extensive use. In this instance, the articles of the present invention are disposed within or attached to a separate personal care implement that is not readily disposable, e.g., a bath towel or washcloth. In addition, the disposable articles of the present invention may be removeably attached to a handle or grip suitable for moving the article over the surface to be cleansed and/or therapeutically treated (e.g., conditioned).

Most importantly, the articles of the present invention are not only effective at cleansing but are also manufactured more efficiently due to their inclusion of a cleansing component that can be characterized as a "hotmelt". A "hotmelt" is any material that undergoes a transition from a solid or semi-solid state at a lower temperature, to a liquid or semi-liquid state at a higher temperature (the extent to which can be physically measured rheologically by a skilled artisan). The use of a hotmelt surfactant system, i.e., the cleansing component, allows for benefits such as: 1) speed and ease of manufacture resulting from a one stage liquid tank mixing process; 2) increased processing speed during coating of the articles with the cleansing component; 3) minimal or no drying time; 4) reduced preservative use due to lack of water present; improved chemical compatibility in anhydrous embodiments of the cleansing component; and 5) reduced tackiness and/or strikethrough due to the solid state of the cleansing component at room temperature.

Although in preferred embodiments the articles of the present invention are suitable for personal care applications, they may also be useful in a variety of other industries such as the automotive care, marine vehicle care, household care, animal care, etc. where surfaces or areas are in need of cleansing and/or application of a benefit agent, e.g., wax, conditioner, UV protectant, etc.

In preferred embodiments of the present invention, the articles are suitable for personal care applications and are useful for cleansing and optionally conditioning the skin, hair, and similar surfaces in need of such treatment. Consumers use these articles by wetting them with water and rubbing on the area to be treated. The article comprises a water insoluble substrate comprising a first creped nonwoven layer; and a cleansing component containing a lathering surfactant or additionally a therapeutic benefit component wherein the cleansing component exhibits a log $[(\eta\ @\ 25°\ C.)/(\eta\ @\ 200°\ C.)]$ greater than about 0.45. In another embodiment, the cleansing component additionally exhibits a complex viscosity measured under an oscillation stress of 1 Pa of greater than about 100 Pa·s. at 25° C. Without being limited by theory, it is believed that the creped nonwoven layer of the substrate having these defined properties enhances lathering which in turn increases cleansing and exfoliation, and optimizes delivery and deposition of a therapeutic or aesthetic benefit agent which might be contained within the article.

SUMMARY OF THE INVENTION

The present invention relates to a substantially dry, disposable personal care article suitable for cleansing, said article comprising:

a) a water insoluble substrate comprising a first creped nonwoven layer; and b) a cleansing component disposed adjacent to said water insoluble substrate, wherein said component comprises from about 10% to about 1000%, by weight of the water insoluble substrate, of a lathering surfactant and wherein the cleansing component exhibits a log $[(\eta\ @\ 25°\ C.)/(\eta\ @\ 200°\ C.)]$ greater than about 0.45. In one embodiment, the cleansing component also has a complex viscosity measured under an oscillation stress of 1 Pa of greater than about 100 Pa·s. at 25° C.

In another embodiment, the present invention further relates to a substantially dry, disposable personal care article suitable for cleansing and conditioning wherein the article comprises:

a) a water insoluble substrate comprising a first creped nonwoven layer;

b) a cleansing component disposed adjacent to said water insoluble substrate, wherein said component comprises from about 10% to about 1000%, by weight of the water insoluble substrate, of a lathering surfactant; and c) a therapeutic benefit component, disposed adjacent to said water insoluble substrate, wherein said component comprises from about 10% to about 1000%, by weight of the water insoluble substrate, of a therapeutic benefit agent and wherein the cleansing component exhibits a log $[(\eta\ @\ 25°\ C.)/(\eta\ @\ 200°\ C.)]$ greater than about 0.45. Also, in a preferred embodiment, the cleansing component exhibits a complex viscosity measured under an oscillation stress of 1 Pa of greater than about 100 Pa·s. at 25° C.

The present invention also relates to a method of cleansing and additionally conditioning the skin and hair that comprises the steps of: a) wetting such articles with water and b) contacting the skin or hair with the wetted articles.

All percentages and ratios used herein, unless otherwise indicated, are by weight and all measurements made are at 25° C., unless otherwise designated. The invention hereof can comprise, consist of, or consist essentially of, the essential as well as optional ingredients and components described therein.

In the description of the invention various embodiments and/or individual features are disclosed. As will be apparent for the skilled practitioner all combinations of such embodiments and features are possible and can result in preferred executions of the invention.

All documents referred to herein, including patents, patent applications, and printed publications, are hereby incorporated by reference in their entirety in this disclosure.

DETAILED DESCRIPTION OF THE INVENTION

As used herein, "disposable" is used in its ordinary sense to mean an article that is disposed or discarded after a limited number of usage events, preferably less than 25, more preferably less than about 10, and most preferably less than about 2 entire usage events.

As used herein, "substantially dry" means that the articles of the present invention exhibit a Moisture Retention of less than about 0.95 gms, preferably less than about 0.75 gms, even more preferably, less than about 0.5 gms, even more preferably less than about 0.25 gms, even still more preferably less than about 0.15 gms, and most preferably, less than about 0.1 gms. The determination of the Moisture Retention is discussed later.

The personal care articles of the present invention comprise the following essential components.

WATER INSOLUBLE SUBSTRATE

The articles of the present invention comprise a water insoluble substrate that further comprises a first creped nonwoven layer exhibiting distinct physical properties. Preferably, the substrate layers, including the creped nonwoven layer and any additional layers, are soft yet invigorating to the skin of the consumer when used. In any case, however, the nonwoven layer and any additional layers are each defined as having both an interior and exterior surface. In both cases, the interior surfaces of the layers are those which face the inside or innermost portion of the article of the present invention whereas the exterior surfaces of the layers are those which face the outside or outermost portion of the article. Generally, the orientation of the articles of the present invention may be defined either such that the creped nonwoven layer is closer to the side of the article suitable for gripping (i.e., the gripping side) or closer to the side of the article to be contacted with the area to be cleansed and/or therapeutically treated, e.g. the skin/site contact side. Both sides of the article, however, are suitable for contact with the skin.

Without being limited by theory, the water insoluble substrate enhances cleansing and/or therapeutic treatment. The substrate can have the same or differing textures on each side such that the gripping side of the article is the same or a different texture as the skin/site contact side. The substrate may act as an efficient lathering and exfoliating implement. By physically coming into contact with the skin or hair, the substrate significantly aids in cleansing and removal of dirt, makeup, dead skin, and other debris. In preferred embodiments, however, the substrate is non-scouring or nonabrasive to the skin.

CREPED NONWOVEN LAYER

The water insoluble substrate of the present invention further comprises a first creped nonwoven layer (or "first layer"). This nonwoven layer is preferably lofty and fluid-permeable. This nonwoven layer is useful for engaging or retaining the cleansing component and/or therapeutic benefit component within the article. Furthermore, the creped nonwoven layer is suitable for contact with the skin in which case it is preferred that the layer is soft to the skin.

Materials suitable for the nonwoven layer are selected from the group consisting of cellulosic nonwovens, non-lofty nonwovens, sponges (i.e., both natural and synthetic), formed films, non-lofty battings, and combinations thereof. Preferably, the nonwoven layer comprises materials selected from the group consisting of cellulosic nonwovens, non-lofty nonwovens, formed films, non-lofty battings, foams, sponges, reticulated foams, vacuum-formed laminates, scrims, polymeric nets, and combinations thereof. More preferably, the nonwoven layer comprises materials selected from the group consisting of cellulosic nonwovens, non-lofty nonwovens, formed films, non-lofty battings, and combinations thereof. As used herein, "nonwoven" means that the layer does not comprise fibers which are woven into a fabric but the layer need not comprise fibers at all, e.g., formed films, sponges, foams, scrims, etc. When the layer comprises fiber, the fibers can either be random (i.e., randomly aligned) or they can be carded (i.e., combed to be oriented in primarily one direction). Furthermore, the nonwoven layer can be a composite material composed of a combination of additional layers, i.e., plies, of random and carded fibers.

The creped nonwoven layer may comprise a variety of both natural and synthetic fibers or materials. As used herein, "natural" means that the materials are derived from plants, animals, insects or byproducts of plants, animals, and insects. The conventional base starting material is usually a fibrous web comprising any of the common synthetic or natural textile-length fibers, or combinations thereof.

Nonlimiting examples of natural materials useful in the present invention include, but are not limited to, silk fibers, keratin fibers and cellulosic fibers. Nonlimiting examples of keratin fibers include those selected from the group consisting of wool fibers, camel hair fibers, and the like. Nonlimiting examples of cellulosic fibers include those selected from the group consisting of wood pulp fibers, cotton fibers, hemp fibers, jute fibers, flax fibers, and combinations thereof. Cellulosic fiber materials are preferred in the present invention.

Nonlimiting examples of synthetic materials useful in the present invention include those selected from the group consisting of acetate fibers, acrylic fibers, cellulose ester fibers, modacrylic fibers, polyamide fibers, polyester fibers, polyolefin fibers, polyvinyl alcohol fibers, rayon fibers, polyethylene foam, polyurethane foam, and combinations thereof. Examples of suitable synthetic materials include acrylics such as acrilan, creslan, and the acrylonitrile-based fiber, orion; cellulose ester fibers such as cellulose acetate, arnel, and acele; polyamides such as nylons (e.g., nylon 6, nylon 66, nylon 610, and the like); polyesters such as fortrel, kodel, and the polyethylene terephthalate fiber, polybutylene terephthalate fiber, dacron; polyolefins such as polypropylene, polyethylene; polyvinyl acetate fibers; polyurethane foams and combinations thereof. These and other suitable fibers and the nonwovens prepared therefrom are generally described in Riedel, "Nonwoven Bonding Methods and Materials," *Nonwoven World* (1987); *The Encyclopedia Americana*, vol. 11, pp. 147–153, and vol. 26, pp. 566–581 (1984); U.S. Pat. No. 4,891,227, to Thaman et al., issued Jan. 2, 1990; and U.S. Pat. No. 4,891,228.

Nonwovens made from natural materials consist of webs or sheets most commonly formed on a fine wire screen from a liquid suspension of the fibers. See C. A. Hampel et al., *The Encyclopedia of Chemistry*, third edition, 1973, pp. 793–795 (1973); *The Encyclopedia Americana*, vol. 21, pp. 376–383 (1984); and G. A. Smook, *Handbook of Pulp and Paper Technologies*, Technical Association for the Pulp and Paper Industry (1986).

Natural material nonwovens useful in the present invention may be obtained from a wide variety of commercial sources. Nonlimiting examples of suitable commercially available paper layers useful herein include Airtex®, an embossed airlaid cellulosic layer having a base weight of about 71 gsy, available from James River, Green Bay, Wis.; and Walkisoft®, an embossed airlaid cellulosic having a base weight of about 75 gsy, available from Walkisoft U.S.A., Mount Holly, N.C.

Additional suitable nonwoven materials include, but are not limited to, those disclosed in U.S. Pat. Nos. 4,447,294, issued to Osborn on May 8, 1984; 4,603,176 issued to Bjorkquist on Jul. 29, 1986; 4,981,557 issued to Bjorkquist on Jan. 1, 1991; 5,085,736 issued to Bjorkquist on Feb. 4, 1992; 5,138,002 issued to Bjorkquist on Aug. 8, 1992; 5,262,007 issued to Phan et al. on Nov. 16, 1993; 5,264,082, issued to Phan et al. on Nov. 23, 1993; 4,637,859 issued to Trokhan on Jan. 20, 1987; 4,529,480 issued to Trokhan on Jul. 16, 1985; 4,687,153 issued to McNeil on Aug. 18, 1987; 5,223,096 issued to Phan et al. on Jun. 29, 1993 and 5,679,222, issued to Rasch et al. on Oct. 21, 1997.

Methods of making nonwovens are well known in the art. Generally, these nonwovens can be made by air-laying, water-laying, meltblowing, coforming, spunbonding, or carding processes in which the fibers or filaments are first cut to desired lengths from long strands, passed into a water or air stream, and then deposited onto a screen through which the fiber-laden air or water is passed. The resulting layer, regardless of its method of production or composition, is then subjected to at least one of several types of bonding operations to anchor the individual fibers together to form a self-sustaining web. In the present invention the creped nonwoven layer can be prepared by a variety of processes including, but not limited to, air-entanglement, hydroentanglement, thermal bonding, and combinations of these processes.

Creped nonwoven substrates made from synthetic materials useful in the present invention can be obtained from a wide variety of commercial sources. Nonlimiting examples of suitable nonwoven layer materials useful herein include HEF 40-047, an apertured hydroentangled material containing about 50% rayon and 50% polyester, and having a basis weight of about 61 grams per square meter (gsm), available from Veratec, Inc., Walpole, Mass.; HEF 140-102, an apertured hydroentangled material containing about 50% rayon and 50% polyester, and having a basis weight of about 67 gsm, available from Veratec, Inc., Walpole, Mass.; Novonet® 149-616, a thermo-bonded grid patterned material containing about 100% polypropylene, and having a basis weight of about 60 gsm available from Veratec, Inc., Walpole, Mass.; Novonet® 149-801, a thermo-bonded grid patterned material containing about 69% rayon, about 25% polypropylene, and about 6% cotton, and having a basis weight of about 90 gsm, available from Veratec, Inc. Walpole, Mass.; Novonet® 149-191, a thermo-bonded grid patterned material containing about 69% rayon, about 25% polypropylene, and about 6% cotton, and having a basis weight of about 120 gsm, available from Veratec, Inc. Walpole, Mass.; HEF Nubtex® 149-801, a nubbed, apertured hydroentangled material, containing about 100% polyester, and having a basis weight of about 84 gsm, available from Veratec, Inc. Walpole, Mass.; Keybak® 951V, a dry formed apertured material, containing about 75% rayon, about 25% acrylic fibers, and having a basis weight of about 51 gsm, available from Chicopee, New Brunswick, N.J.; Keybak® 1368, an apertured material, containing about 75% rayon, about 25% polyester, and having a basis weight of about 47 gsm, available from Chicopee, New Brunswick, N.J.; Duralace® 1236, an apertured, hydroentangled material, containing about 100% rayon, and having a basis weight from about 48 gsm to about 138 gsm, available from Chicopee, New Brunswick, N.J.; Duralace® 5904, an apertured, hydroentangled material, containing about 100% polyester, and having a basis weight from about 48 gsm to about 138 gsm, available from Chicopee, New Brunswick, N.J.; Chicopee® 5763, a carded hydroapertured material (8×6 apertures per inch, 3×2 apertures per cm), containing about 70% rayon, about 30% polyester, and a optionally a latex binder (Acrylate or EVA based) of up to about 5% w/w, and having a basis weight from about 60 gsm to about 90 gsm, available form Chicopee, New Brunswick, N.J.; Chicopee® 9900 series (e.g., Chicopee 9931, 62 gsm, 50/50 rayon/polyester, and Chicopee 9950 50 gsm, 50/50 rayon/polyester), a carded, hydroentangled material, containing a fiber composition of from 50% rayon/50% polyester to 0% rayon/100% polyester or 100% rayon/0% polyester, and having a basis weight of from about 36 gsm to about 84 gsm, available form Chicopee, New Brunswick, N.J.; Sontara 8868, a hydroentangled material, containing about 50% cellulose and about 50% polyester, and having a basis weight of about 72 gsm, available from Dupont Chemical Corp. Preferred nonwoven substrate materials have a basis weight of about from 24 gsm to about 96 gsm, more preferably from about 36 gsm to about 84 gsm, and most preferably from about 42 gsm to about 78 gsm.

The creped nonwoven layer may also be a polymeric mesh sponge as described in European Patent Application No. EP 702550A1 (published Mar. 27, 1996). Such polymeric mesh sponges comprise a plurality of plies of an extruded tubular netting mesh prepared from a nylon or a strong flexible polymer, such as addition polymers of olefin monomers and polyamides of polycarboxylic acids.

Preferably, the creped nonwoven layer may also be arranged with a polymeric net, e.g., through lamination via heat or chemical means such as adhesives, through hydroentanglement, etc. This arrangement enhances the integrity of the creped nonwoven layer as well as the overall article thereby increasing the substantivity of the article. Polymeric nets (referred to herein as a "scrim" materials) that are useful herein are described in detail in U.S. Pat. No. 4,636,419. The scrim materials can be formed directly at the extrusion die or can be derived from extruded films by fibrillation or by embossing, followed by stretching and splitting. The scrim can be derived from a polyolefin such as polyethylene or polypropylene, copolymers thereof, poly (butylene terephthalate), polyethylene terephthalate, Nylon 6, Nylon 66, and the like. Scrim materials are available from various commercial sources. A preferred scrim material useful in the present invention is a polypropylene scrim, available from Conwed Plastics (Minneapolis, Min.).

In another aspect of the present invention, Applicants have also discovered that the incorporation of the scrim material into the creped nonwoven layer, followed by heating, provides macroscopic three-dimensional character to the sheet. This macroscopic three-dimensionality has been found to greatly enhance cleansing performance of the article, even where the basis weight of the sheet is essentially uniform. In particular, macroscopic three-dimensionality is achieved when the scrim/fiber composite is subjected to heating, then cooling. This process results in shrinkage (in the X-Y dimension) of the scrim and, as a result of its being attached with the fibers, provides a sheet with greater three-dimensionality. As used herein, the term "X-Y dimension" refers to the plane orthogonal to the thickness of the layer, ply, or article, or a component thereof. The X and Y dimensions usually correspond to the length and width, respectively, of the sheet or a sheet component. As used herein, the term "Z-dimension" refers to the dimension orthogonal to the length and width of the cleaning sheet of the present invention, or a component thereof. The Z-dimension usually corresponds to the thickness of the sheet.

The degree of added three-dimensionality is controlled by the level of heating applied to the scrim/cleaning combination. The inclusion of a scrim is particularly beneficial when the fiber aspect of the structure is a nonwoven, particularly when the structure is hydroentangled. Further detail of suitable scrim material containing nonwovens may be found in copending U.S. application Ser. Nos. 09/082,396 and 09/082,349, both filed on May 20, 1998, by Fereshtehkho et al.

The creped nonwoven layer may also comprise formed films and composite materials, i.e., multiple materials containing formed films. Preferably, such formed films comprise plastics which tend to be soft to the skin. Suitable soft plastic formed films include, but are not limited to, polyolefins such as low density polyethylenes (LDPE). In such cases where the nonwoven layer comprises a plastic formed film, it is preferred that the nonwoven layer be apertured, e.g., macroapertured or microapertured, such that the layer is fluid permeable. In one embodiment, the nonwoven layer comprises a plastic formed film that is only microapertured. The surface aberrations of the microapertures, i.e., the male side, are preferably located on the interior surface of the second layer and preferably face toward the inside of the substrate, i.e., toward the cleansing component and/or therapeutic benefit component. In certain embodiments which include apertures having petal-like edged surface aberrations, without being limited by theory, it is believed that when the surface aberrations of the apertures face toward the surfactant-containing cleansing component/ therapeutic benefit component, the application of pressure by the hand to the article allows the petal-like edges of the surface aberrations to fold inward thereby creating numerous valves on the interior surface of the layer which in effect meter out the cleansing component/therapeutic benefit component contained within the article thereby extending the article's useful life.

In another embodiment, the nonwoven layer comprises a plastic formed film which is both microapertured and macroapertured. In such embodiments, the nonwoven layer is well-suited to contact the area to be cleansed and/or therapeutically treated given the cloth-like feel of such microapertured films. Preferably, in such an embodiment, the surface aberrations of the microapertures face opposite of the surface aberrations of the macroapertures on the nonwoven layer. In such an instance, it is believed that the macroapertures maximize the overall wetting/lathering of the article by the three-dimensional thickness formed from the surface aberrations that are under constant compression and decompression during the use of the article thereby creating lathering bellows.

In any case, the nonwoven layer comprising a formed film preferably has at least about 100 apertures/$cm^2$, more preferably at least 500 apertures/$cm^2$, even still more preferably at least about 1000 apertures/$cm^2$, and most preferably at least about 1500 apertures/$cm^2$ of the substrate. More preferred embodiments of the present invention include a nonwoven layer which has water flux rate of from about 5 $cm^3/cm^2$-s to about 70 $cm^3/cm^2$-s, more preferably from about 10 $cm^3/cm^2$-s to about 50 $cm^3/cm^2$-s and most preferably from about 15 $cm^3/cm^2$-s to about 40 $cm^3/cm^2$-s.

Suitable formed films and formed film-containing composite materials useful in the nonwoven layer of the present invention include, but are not limited to, those disclosed in U.S. Pat. No. 4,342,314 issued to Radel et al. on Aug. 3, 1982, commonly assigned co-pending application U.S. Ser. No. 08/326,571 and PCT Application No. US95/07435, filed June 12, 1995 and published Jan. 11, 1996, and U.S. Pat. No. 4,629,643, issued to Curro et al. on Dec. 16, 1986. Furthermore, the nonwoven layer may be a formed film composite material comprising at least one formed film and at least one nonwoven wherein the layer is vacuum formed. A suitable formed film composite material includes, but is not limited to, a vacuum laminated composite formed film material formed by combining a carded polypropylene nonwoven having a basis weight of 30 gsm with a formed film.

Suitable creped nonwoven layer may comprise formed films which are macroscopically expanded. As used herein, "macroscopically expanded, refers to webs, ribbons, and films which have been caused to conform to the surface of a three-dimensional forming structure so that both surfaces thereof exhibit a three-dimensional forming pattern of surface aberrations corresponding to the macroscopic cross-section of the forming structure, wherein the surface aberrations comprising the pattern are individually discernible to the normal naked eye (i.e., normal naked eye having 20/20 vision) when the perpendicular distance between the viewer's eye and the plane of the web is about 12 inches.

As used herein, "embossed" it is meant that the forming structure of the material exhibits a pattern comprised primarily of male projections. On the other hand, "debossed" refers to when the forming structure of the material exhibits a pattern comprised primarily of female capillary networks.

Preferred macroscopically expanded films comprise formed films which are structural elastic-like films. These films are described in U.S. Pat. No. 5,554,145, issued Sep. 10, 1996, to Roe et al.

Materials suitable for use in the creped nonwoven layer which have a thickness of at least one millimeter include, but are not limited to, those web materials disclosed in U.S. Pat. No. 5,518,801, issued to Chappell et al. on May 21, 1996.

Additionally, the creped nonwoven layer and any additional optional layers are preferably bonded to one another in order to maintain the integrity of the article. This bonding may consist of spot bonding (e.g., hot point bonding), continuous joining (e.g., laminated, etc.) or in a discontinuous pattern, or by bonding at the external edges (or periphery) of the layers and/or at discrete loci or combinations thereof. The bonding may also be arranged such that geometric shapes and patterns, e.g. diamonds, circles, squares, etc., are created on the exterior surfaces of the layers and the resulting article.

In any event, it is preferred that the bonded area present between the creped nonwoven layer and any optional layers be not greater than about 50% of the total surface area of the layers, preferably not greater than about 15%, more preferably not greater than about 10%, and most preferably not greater than about 8%.

Any layer discussed herein comprises at least two surfaces, namely an interior surface and an exterior surface, each of which may have the same or different texture and abrasiveness. Preferably, the articles of the present invention comprise substrates and therefore layers which are soft to the skin. However, differing texture substrates can result from the use of different combinations of materials or from the use of different manufacturing processes or a combination thereof. For instance, a dual textured water insoluble substrate can be made to provide a personal care article with the advantage of having a more abrasive side for exfoliation and a softer, absorbent side for gentle cleansing and therapeutic treatment. In addition, the separate layers of the substrate can be manufactured to have different colors, thereby helping the user to further distinguish the surfaces.

Furthermore, any layers of the articles as well as the articles themselves may be made into a wide variety of shapes and forms including flat pads, thick pads, thin sheets, ball-shaped implements, irregularly shaped implements. The exact size of the layers will depend upon the desired use and characteristics of the article and may range in surface area size from about a square inch to about hundreds of square inches. Especially convenient layer and article shapes include, but are not limited to, square, circular, rectangular, hourglass, mitt-type or oval shapes having a surface area of from about 5 in$^2$ to about 200 in$^2$, preferably from about 6 in$^2$ to about 120 in$^2$, and more preferably from about 15 in$^2$ to about 100 in$^2$, and a thickness of from about 0.5 mm to about 50 mm, preferably from about 1 mm to about 25 mm, and more preferably from about 2 mm to about 20 mm.

CLEANSING COMPONENT

The articles of the present invention comprise a cleansing component that further comprises one or more surfactants. It is been discovered that when the cleansing component contains a hotmelt surfactant system, improved processibility of the resultant article follows. In particular, the cleansing component is remeltable and typically solidifies upon cooling such that no additional mechanical drying means is necessary during processing of the article. Additionally, the hotmelt system of the cleansing component allows it to last longer during use than a typical liquid cleansing composition would. This extended life is primarily due to the semi-solid nature that the hotmelt system lends to the cleansing component thereby slowing dissolution.

The cleansing component of the present articles exhibit at least a log [($\eta$ @ 25° C.)/($\eta$ @ 200° C.)] greater than about 0.45, preferably greater than about 1.5, even more preferably greater than about 3, still even more preferably greater than about 4, and most preferably greater than about 5. Preferably, the cleansing component exhibits a log [($\eta$ @ 25° C.)/($\eta$ @ 125° C.)] greater than about 0.45, preferably greater than about 1.5, even more preferably greater than about 3, still even more preferably greater than about 4, and most preferably greater than about 5. Preferably, the cleansing component exhibits a log [($\eta$ @ 25° C.)/($\eta$ @ 100° C.)] greater than about 0.45, preferably greater than about 1.5, even more preferably greater than about 3, still even more preferably greater than about 4, and most preferably greater than about 5. Still more preferably, the cleansing component exhibits a log [($\eta$ @ 25° C.)/($\eta$ @ 80° C.)] greater than about 0.45, preferably greater than about 1.5, even more preferably greater than about 3, still even more preferably greater than about 4, and most preferably greater than about 5. In the most preferred embodiments of the present invention the cleansing component exhibits a log[($\eta$ @ 25° C.)/($\eta$ @ 60° C.)] greater than about 0.45, preferably greater than about 1.5, even more preferably greater than about 3, still even more preferably greater than about 4, and most preferably greater than about 5. Over the latter temperature range, it has been discovered that many of the chemicals that might also be included in the cleansing component also tend to exhibit improved stability in the component and are less prone to chemical breakdown due to the lower temperatures.

Additionally, the stable and aesthetically desirable semi-solid nature of the cleansing component of the present article prior to use can also be characterized as follows. The cleansing component preferably exhibits a complex viscosity measured under an oscillation stress of 1 Pa of greater than about 100 Pa·s., more preferably, greater than about 500 Pa·s., even more preferably, greater than about, 1000 Pa·s., and most preferably, greater than about 2000 Pa·s., all at 25° C. This viscosity is measured utilizing the oscillation method described below.

Both of these methods of characterization, however, illustrate the semi-solid state nature of the cleansing component of the articles at 25° C.

The cleansing component is disposed adjacent to the creped nonwoven layer of the water insoluble substrate. In certain embodiments, the cleansing component is impregnated into the water insoluble substrate. In another embodiment, the cleansing component is deposited onto either or both surfaces of the water insoluble substrate. The articles of the present invention comprise from about 10% to about 1,000%, preferably from about 50% to about 600%, and more preferably from about 100% to about 250%, based on the weight of the water insoluble substrate, of the surfactant. Also, the articles of the present invention preferably comprise at least about 1 gram of cleansing component that is positioned adjacent to the substrate.

The surfactants of the cleansing component are preferably lathering surfactants. As used herein, "lathering surfactant"

means a surfactant, which when combined with water and mechanically agitated generates a foam or lather. Such surfactants are preferred since increased lather is important to consumers as an indication of cleansing effectiveness. In certain embodiments, the surfactants or combinations of surfactants are mild. As used herein, "mild" means that the surfactants as well as the articles of the present invention demonstrate skin mildness comparable to a mild alkyl glyceryl ether sulfonate (AGS) surfactant based synthetic bar, i.e., synbar. Methods for measuring mildness, or inversely the irritancy, of surfactant containing articles, are based on a skin barrier destruction test. In this test, the milder the surfactant, the lesser the skin barrier is destroyed. Skin barrier destruction is measured by the relative amount of radio-labeled (tritium labeled) water ($3H-H_2O$) which passes from the test solution through the skin epidermis into the physiological buffer contained in the diffusate chamber. This test is described by T. J. Franz in the *J. Invest. Dermatol.*, 1975, 64, pp. 190–195; and in U.S. Pat. No. 4,673,525, to Small et al., issued Jun. 16, 1987, which are both incorporated by reference herein in their entirety. Other testing methodologies for determining surfactant mildness well known to one skilled in the art can also be used.

A wide variety of lathering surfactants are useful herein and include those selected from the group consisting of anionic lathering surfactants, nonionic lathering surfactants, cationic lathering surfactants, amphoteric lathering surfactants, and mixtures thereof.

Anionic Lathering Surfactants

Nonlimiting examples of anionic lathering surfactants useful in the compositions of the present invention are disclosed in McCutcheon's, *Detergents and Emulsifiers*, North American edition (1986), published by Allured Publishing Corporation; McCutcheon's, *Functional Materials*, North American Edition (1992); and U.S. Pat. No. 3,929,678, to Laughlin et al., issued Dec. 30, 1975, each of which is incorporated by reference herein in their entirety.

A wide variety of anionic surfactants are potentially useful herein. Nonlimiting examples of anionic lathering surfactants include those selected from the group consisting of alkyl and alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, acyl glutamates, acyl sarcosinates, alkyl sulfoacetates, acylated peptides, alkyl ether carboxylates, acyl lactylates, anionic fluorosurfactants, and combinations thereof. Combinations of anionic surfactants can be used effectively in the present invention.

Anionic surfactants for use in the cleansing component include alkyl and alkyl ether sulfates. These materials have the respective formulae $R1O-SO3M$ and $R1(CH2H4O)x-O-SO3M$, wherein R1 is a saturated or unsaturated, branched or unbranched alkyl group from about 8 to about 24 carbon atoms, x is 1 to 10, and M is a water-soluble cation such as ammonium, sodium, potassium, magnesium, triethanolamine, diethanolamine and monoethanolamine. The alkyl sulfates are typically made by the sulfation of monohydric alcohols (having from about 8 to about 24 carbon atoms) using sulfur trioxide or other known sulfation technique. The alkyl ether sulfates are typically made as condensation products of ethylene oxide and monohydric alcohols (having from about 8 to about 24 carbon atoms) and then sulfated. These alcohols can be derived from fats, e.g., coconut oil or tallow, or can be synthetic. Specific examples of alkyl sulfates which may be used in the cleansing component are sodium, ammonium, potassium, magnesium, or TEA salts of lauryl or myristyl sulfate. Examples of alkyl ether sulfates which may be used include ammonium, sodium, magnesium, or TEA laureth-3 sulfate.

Another suitable class of anionic surfactants are the sulfated monoglycerides of the form $R1CO-O-CH2-C(OH)H-CH2-O-SO3M$, wherein R1 is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. These are typically made by the reaction of glycerin with fatty acids (having from about 8 to about 24 carbon atoms) to form a monoglyceride and the subsequent sulfation of this monoglyceride with sulfur trioxide. An example of a sulfated monoglyceride is sodium cocomonoglyceride sulfate.

Other suitable anionic surfactants include olefin sulfonates of the form $R1SO3M$, wherein R1 is a mono-olefin having from about 12 to about 24 carbon atoms, and M is a water-soluble cation such as ammonium, sodium, potassium, magnesium, triethanolamine, diethanolamine and monoethanolamine. These compounds can be produced by the sulfonation of alpha olefins by means of uncomplexed sulfur trioxide, followed by neutralization of the acid reaction mixture in conditions such that any sultones which have been formed in the reaction are hydrolyzed to give the corresponding hydroxyalkanesulfonate. An example of a sulfonated olefin is sodium C14/C16 alpha olefin sulfonate.

Other suitable anionic surfactants are the linear alkylbenzene sulfonates of the form $R1-C6H4-SO3M$, wherein R1 is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. These are formed by the sulfonation of linear alkyl benzene with sulfur trioxide. An example of this anionic surfactant is sodium dodecylbenzene sulfonate.

Still other anionic surfactants suitable for this cleansing component include the primary or secondary alkane sulfonates of the form $R1SO3M$, wherein R1 is a saturated or unsaturated, branched or unbranched alkyl chain from about 8 to about 24 carbon atoms, and M is a water-soluble cation such as ammonium, sodium, potassium, magnesium, triethanolamine, diethanolamine and monoethanolamine. These are commonly formed by the sulfonation of paraffins using sulfur dioxide in the presence of chlorine and ultraviolet light or another known sulfonation method. The sulfonation can occur in either the secondary or primary positions of the alkyl chain. An example of an alkane sulfonate useful herein is alkali metal or ammonium C13–C17 paraffin sulfonates.

Still other suitable anionic surfactants are the alkyl sulfosuccinates, which include disodium N-octadecylsulfosuccinamate; diammonium lauryl sulfosuccinate; tetrasodium N-(1,2-dicarboxyethyl)-N-octadecylsulfosuccinate; diamyl ester of sodium sulfosuccinic acid; dihexyl ester of sodium sulfosuccinic acid; and dioctyl esters of sodium sulfosuccinic acid.

Also useful are taurates that are based on taurine, which is also known as 2-aminoethanesulfonic acid. Examples of taurates include N-alkyltaurines such as the one prepared by reacting dodecylamine with sodium isethionate as detailed in U.S. Pat. No. 2,658,072. Other examples based of taurine include the acyl taurines formed by the reaction of n-methyl taurine with fatty acids (having from about 8 to about 24 carbon atoms).

Another class of anionic surfactants suitable for use in the cleansing component is the acyl isethionates. The acyl isethionates typically have the formula R1CO—O—CH2CH2SO3M wherein R1 is a saturated or unsaturated, branched or unbranched alkyl group having from about 10 to about 30 carbon atoms, and M is a cation. These are typically formed by the reaction of fatty acids (having from about 8 to about 30 carbon atoms) with an alkali metal isethionate. Nonlimiting examples of these acyl isethionates include ammonium cocoyl isethionate, sodium cocoyl isethionate, sodium lauroyl isethionate, and mixtures thereof.

Still other suitable anionic surfactants are the alkylglyceryl ether sulfonates of the form R1—OCH2—C(OH)H—CH2—SO3M, wherein R1 is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. These can be formed by the reaction of epichlorohydrin and sodium bisulfite with fatty alcohols (having from about 8 to about 24 carbon atoms) or other known methods. One example is sodium cocoglyceryl ether sulfonate.

Other suitable anionic surfactants include the sulfonated fatty acids of the form R1—CH(SO4)—COOH and sulfonated methyl esters of the from R1—CH(SO4)—CO—O—CH3, where R1 is a saturated or unsaturated, branched or unbranched alkyl group from about 8 to about 24 carbon atoms. These can be formed by the sulfonation of fatty acids or alkyl methyl esters (having from about 8 to about 24 carbon atoms) with sulfur trioxide or by another known sulfonation technique. Examples include alpha sulphonated coconut fatty acid and lauryl methyl ester.

Other anionic materials include phosphates such as monoalkyl, dialkyl, and trialkylphosphate salts formed by the reaction of phosphorous pentoxide with monohydric branched or unbranched alcohols having from about 8 to about 24 carbon atoms. These could also be formed by other known phosphation methods. An example from this class of surfactants is sodium mono or dilaurylphosphate.

Other anionic materials include acyl glutamates corresponding to the formula R1CO—N(COOH)—CH2CH2—CO2M wherein R1 is a saturated or unsaturated, branched or unbranched alkyl or alkenyl group of about 8 to about 24 carbon atoms, and M is a water-soluble cation. Nonlimiting examples of which include sodium lauroyl glutamate and sodium cocoyl glutamate.

Other anionic materials include alkanoyl sarcosinates corresponding to the formula R1CON(CH3)—CH2CH2—CO2M wherein R1 is a saturated or unsaturated, branched or unbranched alkyl or alkenyl group of about 10 to about 20 carbon atoms, and M is a water-soluble cation. Nonlimiting examples of which include sodium lauroyl sarcosinate, sodium cocoyl sarcosinate, and ammonium lauroyl sarcosinate.

Other anionic materials include alkyl ether carboxylates corresponding to the formula R1—(OCH2CH2)$x$—OCH2—CO2M wherein R1 is a saturated or unsaturated, branched or unbranched alkyl or alkenyl group of about 8 to about 24 carbon atoms, x is 1 to 10, and M is a water-soluble cation. Nonlimiting examples of which include sodium laureth carboxylate.

Other anionic materials include acyl lactylates corresponding to the formula R1CO—[O—CH(CH3)—CO]$x$—CO2M wherein R1 is a saturated or unsaturated, branched or unbranched alkyl or alkenyl group of about 8 to about 24 carbon atoms, x is 3, and M is a water-soluble cation. Nonlimiting examples of which include sodium cocoyl lactylate.

Other anionic materials include the carboxylates, nonlimiting examples of which include sodium lauroyl carboxylate, sodium cocoyl carboxylate, and ammonium lauroyl carboxylate. Anionic flourosurfactants can also be used.

Other anionic materials include natural soaps derived from the saponification of vegetable and/or animal fats & oils exmaples of which include sodium laurate, sodium myristate, palmitate, stearate, tallowate, cocoate.

Any counter cation, M, can be used on the anionic surfactant. Preferably, the counter cation is selected from the group consisting of sodium, potassium, ammonium, monoethanolamine, diethanolamine, and triethanolamine. More preferably, the counter cation is ammonium.

Nonionic Lathering Surfactants

Nonlimiting examples of nonionic lathering surfactants for use in the compositions of the present invention are disclosed in McCutcheon's, *Detergents and Emulsifiers,* North American edition (1986), published by allured Publishing Corporation; and McCutcheon's, *Functional Materials,* North American Edition (1992).

Nonionic lathering surfactants useful herein include those selected from the group consisting of alkyl glucosides, alkyl polyglucosides, polyhydroxy fatty acid amides, alkoxylated fatty acid esters, sucrose esters, amine oxides, and mixtures thereof.

Alkyl glucosides and alkyl polyglucosides are useful herein, and can be broadly defined as condensation products of long chain alcohols, e.g., C8–30 alcohols, with sugars or starches or sugar or starch polymers, i.e., glycosides or polyglycosides. These compounds can be represented by the formula $(S)_n$—O—R wherein S is a sugar moiety such as glucose, fructose, mannose, and galactose; n is an integer of from about 1 to about 1000, and R is a C8–30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a C8–20 alkyl group, and n is an integer of from about 1 to about 9. Commercially available examples of these surfactants include decyl polyglucoside (available as APG 325 CS from Henkel) and lauryl polyglucoside (available as APG 600CS and 625 CS from Henkel). Also useful are sucrose ester surfactants such as sucrose cocoate and sucrose laurate.

Other useful nonionic surfactants include polyhydroxy fatty acid amide surfactants, more specific examples of which include glucosamides, corresponding to the structural formula:

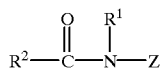

wherein:

$R^1$ is H, $C_1$–$C_4$ alkyl, 2-hydroxyethyl, 2-hydroxy-propyl, preferably $C_1$–$C_4$ alkyl, more preferably methyl or ethyl, most preferably methyl;

$R^2$ is $C_5$–$C_{31}$ alkyl or alkenyl, preferably $C_7$–$C_{19}$ alkyl or alkenyl, more preferably $C_9$–$C_{17}$ alkyl or alkenyl, most preferably $C_{11}$–$C_{15}$ alkyl or alkenyl; and Z is a polhydroxyhydrocarbyl moiety having a linear hydrocarbyl chain with a least 3 hydroxyls directly connected to the chain, or an alkoxylated derivative (preferably ethoxylated or propoxylated) thereof. Z preferably is a sugar moiety selected from the group consisting of glucose, fructose, maltose, lactose, galactose, mannose, xylose, and mixtures thereof.

An especially preferred surfactant corresponding to the above structure is coconut alkyl N-methyl glucoside amide (i.e., wherein the $R^2CO$— moiety is derived from coconut oil fatty acids). Processes for making compositions containing polyhydroxy fatty acid amides are disclosed, for example, in G.B. Patent Specification 809,060, published Feb. 18, 1959, by Thomas Hedley & Co., Ltd.; U.S. Pat. No. 2,965,576, to E. R. Wilson, issued Dec. 20, 1960; U.S. Pat. No. 2,703,798, to A. M. Schwartz, issued Mar. 8, 1955; and U.S. Pat. No. 1,985,424, to Piggott, issued Dec. 25, 1934.

Other examples of nonionic surfactants include amine oxides. Amine oxides correspond to the general formula $R_1R_2R_3N \rightarrow O$, wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyl-dodecylamine oxide, oleyldi(2-hydroxyethyl) amine oxide, dimethyloctylamine oxide, dimethyl-decylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyidi(3-hydroxypropyl) amine oxide, dimethylhexadecylamine oxide.

Nonlimiting examples of preferred nonionic surfactants for use herein are those selected form the group consisting of C8–C14 glucose amides, C8–C14 alkyl polyglucosides, sucrose cocoate, sucrose laurate, lauramine oxide, cocoamine oxide, and mixtures thereof.

Cationic Lathering Surfactants

Cationic lathering surfactants are also useful in the articles of the present invention. Suitable cationic lathering surfactants include, but are not limited to, fatty amines, di-fatty quaternary amines, tri-fatty quaternary amines, imidazolinium quaternary amines, and combinations thereof. Suitable fatty amines include monalkyl quaternary amines such as cetyltrimethylammonium bromide. A suitable quaternary amine is dialklamidoethyl hydroxyethylmonium methosulfate. The fatty amines, however, are preferred. It is preferred that a lather booster is used when the cationic lathering surfactant is the primary lathering surfactant of the cleansing component. Additionally, nonionic surfactants have been found to be particularly useful in combination with such cationic lathering surfactants.

Amphoteric Lathering Surfactants

The term "amphoteric lathering surfactant," as used herein, is also intended to encompass zwitterionic surfactants, which are well known to formulators skilled in the art as a subset of amphoteric surfactants.

A wide variety of amphoteric lathering surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Nonlimiting examples of amphoteric surfactants useful in the compositions of the present invention are disclosed in McCutcheon's, *Detergents and Emulsifiers,* North American edition (1986), published by allured Publishing Corporation; and McCutcheon's, *Functional Materials,* North American Edition (1992).

Nonlimiting examples of amphoteric or zwitterionic surfactants are those selected from the group consisting of betaines, sultaines, hydroxysultaines, alkyliminoacetates, iminodialkanoates, aminoalkanoates, and mixtures thereof.

Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, lauryl dimethyl sulfoethyl betaine, lauryl bis-(2-hydroxyethyl) sulfopropyl betaine, amidobetaines and amidosulfobetaines (wherein the $RCONH(CH_2)_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Examples of sultaines and hydroxysultaines include materials such as cocamidopropyl hydroxysultaine (available as Mirataine CBS from Rhone-Poulenc).

Preferred for use herein are amphoteric surfactants having the following structure:

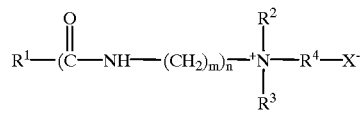

wherein $R^1$ is unsubstituted, saturated or unsaturated, straight or branched chain alkyl having from about 9 to about 22 carbon atoms. Preferred $R^1$ has from about 11 to about 18 carbon atoms; more preferably from about 12 to about 18 carbon atoms; more preferably still from about 14 to about 18 carbon atoms;

m is an integer from 1 to about 3, more preferably from about 2 to about 3, and more preferably about 3;

n is either 0 or 1, preferably 1;

$R^2$ and $R^3$ are independently selected from the group consisting of alkyl having from 1 to about 3 carbon atoms, unsubstituted or mono-substituted with hydroxy, preferred $R^2$ and $R^3$ are $CH_3$;

X is selected from the group consisting of $CO_2$, $SO_3$ and $SO_4$;

$R^4$ is selected from the group consisting of saturated or unsaturated, straight or branched chain alkyl, unsubstituted or monosubstituted with hydroxy, having from 1 to about 5 carbon atoms. When X is $CO_2$, $R^4$ preferably has 1 or 3 carbon atoms, more preferably 1 carbon atom. When X is $SO_3$ or $SO_4$, $R^4$ preferably has from about 2 to about 4 carbon atoms, more preferably 3 carbon atoms.

Examples of amphoteric surfactants of the present invention include the following compounds:

Cetyl dimethyl betaine (this material also has the CTFA designation cetyl betaine)

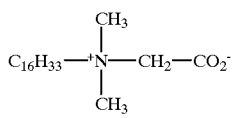

Cocamidopropylbetaine

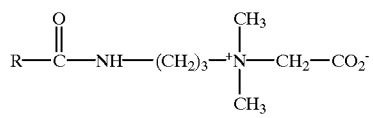

wherein R has from about 9 to about 13 carbon atoms
Cocamidopropyl hydroxy sultaine

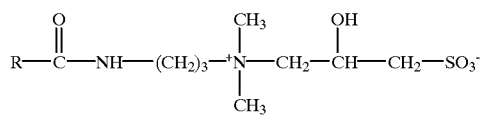

wherein R has from about 9 to about 13 carbon atoms.

Examples of other useful amphoteric surfactants are alkyliminoacetates, and iminodialkanoates and aminoalkanoates of the formulas $RN[(CH_2)_mCO_2M]_2$ and $RNH(CH_2)_mCO_2M$ wherein m is from 1 to 4, R is a $C_8$–$C_{22}$ alkyl or alkenyl, and M is H, alkali metal, alkaline earth metal ammonium, or alkanolammonium. Also included are imidazolinium and ammonium derivatives. Specific examples of suitable amphoteric surfactants include sodium 3-dodecyl-aminopropionate, sodium 3-dodecylaminopropane sulfonate, N-higher alkyl aspartic acids such as those produced according to the teaching of U.S. Pat. No. 2,438,091; and the products sold under the trade name "Miranol" and described in U.S. Pat. No. 2,528, 378. Other examples of useful amphoterics include amphoteric phosphates, such as coamidopropyl PG-dimonium chloride phosphate (commercially available as Monaquat PTC®, from Mona Corp.). Also useful are amphoacetates such as disodium lauroamphodiacetate, sodium lauroamphoacetate, and mixtures thereof.

Preferred lathering surfactants are selected from the group consisting of anionic lathering surfactants selected from the group consisting of ammonium lauroyl sarcosinate, sodium trideceth sulfate, sodium lauroyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isethionate, sodium cetyl sulfate, sodium monolauryl phospate, sodium cocoglyceryl ether sulfonate, sodium $C_9$–$C_{22}$ soap, and combinations thereof; nonionic lathering surfactants selected from the group consisting of lauramine oxide, cocoamine oxide, decyl polyglucose, lauryl polyglucose, sucrose cocoate, C12–14 glucosamides, sucrose laurate, and combinations thereof; cationic lathering surfactants selected from the group consisting of fatty amines, di-fatty quaternary amines, tri-fatty quaternary amines, imidazolinium quaternary amines, and combinations thereof; amphoteric lathering surfactants selected from the group consisting of disodium lauroamphodiacetate, sodium lauroamphoacetate, cetyl dimethyl betaine, cocoamidopropyl betaine, cocoamidopropyl hydroxy sultaine, and combinations thereof.

The cleansing component of the present articles may contain one or more lathering surfactant which have melting points greater than about 25° C. individually or when combined. The high polarity of such surfactants makes them well suited for dissolving other non-hotmelt surfactants and other water soluble actives. Suitable lathering 'hotmelt' surfactants include N-Methyl glucose Amide (GS Base), DEFI (Directly Esterified Fattty acid Isethionates from Lever Bros), Sodium Coco Isethionates, Alkyl Poly Glucosides (e.g. Plantaren 1200® from Cognis) Alkyl Glyceryl Sulfonates, Mono Alkyl Ether Phosphates (e.g. Inter 9502® from Rhodia)

A cleansing components may also be achieved by use of hotmelt carriers, solvents or structuring agents. Suitable are non-aqueous polar solvents/carriers into which surfactants and other water soluble components dissolve during processing at high temperatures. A solid phase is formed when cool, but whole composition melts due to content of meltable solvent. Suitable polar sovents include Polyethylene Glycols (Molecular weight 1000 and above, e.g. Polyox WSR N-3000, Union Carbide), Ethylene Oxide/Propylene Oxide block copolymers. Ethoxylated Alcohols or Propoxylated alcohols ($C_{10}$ or above), (e.g. Empilan KM50 from Allbright & Wilson). Fatty acid esters (e.g. Sodium Cocoyl Lactylate). PVPNA copolymer, Polyvinyl alcohol (e.g. Elvanol 51-05 from Dupont). Also useful are $C_4$–$C_{20}$ alkyl ethers of polypropylene glycols, C10–C20 carboxylic acid esters of polypropylene glycols, and di-C8–C30 alkyl ethers. Also useful are starches and their derivatives (e.g., maltodextrin), dextrins (e.g., Index from National Starch), and sugars such as glucose, sucrose, fructose, and maltose.

Other suitable carriers are non-aqueous low polarity carriers. The surfactant is dispersed in the carrier phase which has a low Hydrophylic/Lipophylic Balance and has partial or low water solubility or conversely the low polarity structurant can be dispersed in the surfactant. It melts at elevated temperature making formula hotmeltable. At room temperature surfactant diffuses out of carrier on contact with water in use. Suitable non-aqueous low polarity carriers are Polyethylene waxes, Paraffin waxes, Lanolin waxes. Also useful herein are alkyl modified siloxanes such as alkyl methicones and alkyl dimethicones wherein the alkyl chain contains 10 to 50 carbons. Such siloxanes are commercially available under the tradenames ABIL WAX 9810® ($C_{24}$–$C_{28}$ alkyl methicone) (sold by Goldschmidt) and SF1632 (cetearyl methicone made by General Electric Company). Also suitable are Ethylene Glycol Distearate, Glycerol esters (e.g, Trihydroxystearin), Fatty alcohols (e.g., Stearyl alcohol), Fatty acids (e.g., Stearic acid).

Other meltable polymeric materials into which the surfactants can be dispersed include, but are not limited to include Polvinylpirrolidone (PVP), Ethylene vinyl acetate (e.g., Elvax 40W® from Dupont).

Structurants/Binders

Another ingredient in the "hotmelt" cleansing component may be structurants and/or binders. Structurants do not have a melt point in the relevant temperature range but can be used in conjunction with a temperature sensitive surfactant phase. Structurants are well known in the art of bar soap making as fillers and may include but are not limited to: Also known in the art are Nylons (e.g., Orgasol 1002® from Elf Atochem), Talc, Kaolin, Bentonite Clay (e.g., Bentone EW from Rheox), and cellulose.

Other suitable fillers may include Aluminium, Magnesium or Calcium silicates, Aluminium Stearate, Distearate or Tristearate (e.g., Aluminium Stearate 132 from Witco) High Molecular weight Silicones and Silanes are also useful structuring agents, examples include Polymethylsilsesquioxane (Tospearl 145A® from Toshiba), Fumed Silica (e.g., Aerosil 200® from Degussa).

Properties of Personal Cleansing Articles

In certain embodiments of the present invention the first creped nonwoven layer of the articles of the present invention exhibits specific physical properties as defined by the Crepe Ratio. The creped nonwoven layer of the articles of the present invention is preferably characterized by having a Crepe Ratio of from about 4.5 to about 45, more preferably the lower Crepe Ratio limit is about 4.1, more preferably about 4.15, even more preferably about 4.2, and most preferably about 4.25. The upper limit for the Crepe Ratio is more preferably 20, even more preferably 15 and most preferably about 12. These lower and upper limits may be combined to give an optimum range.

In order to determine the Crepe Ratio of a particular substrate, the Loft-Soft Ratio must first be determined.

Loft-Soft Ratio Methodology

Loftiness of substrates and softness of substrates are related. Softness has several independent, contributing components. One component is a kind of "pillowy" softness. That is, when a force is applied by hand or finger pressure, the substrate easily compresses in much the same way a pillow compresses under pressure to support a body member resting thereon. This test measures parameters related to loftiness using the following pieces of equipment:

1. Instron Model 1122 Compression and Tensile tester (or equivalent thereof);
2. Instron Serial Number 445 (200 grams full scale) compression load cell (or equivalent thereof);
3. Flat top plate, attachable to load cell;
4. Flat base plate, under load cell;
5. 1.875 inch diameter punch; and
6. a hammer.

Substrate samples are cut using a 1.875 inch diameter punch and hammer. In instances where the punching process inelastically compresses edges of discs, the edges are carefully fluffed to restore original dimension. With the top plate in position, the Instron load cell is calibrated and is then run in compression mode at 0.50 inches/minute rate of descent. The Instron may be controlled manually or by computer as long as the final compression is greater than 30 grams/in$^2$ pressure and data is collected quickly enough (computer assisted recommended) to determine the height at various compression values during descent. The top plate is then moved down until it contacts the base plate at which point the height is set at zero. It is important that the top plate and base plate are parallel, making contact at all points simultaneously.

Once the apparatus is zeroed, the top plate is retracted to a position above the base plate allowing sufficient space to interpose a substrate sample disc. A substrate disc is then placed in the center of the base plate. The Instron is then set to compress each substrate sample once fully. Next, the Instron is turned on and the height and force of the top plate is continuous recorded. Once the compression of the sample is complete, the compression of the sample is repeated as many times as is needed to establish a reliable average. The average height above the base plate at compression values of 5 gms/in$^2$ and 30 gms/in$^2$ equals the thickness at 5 gms/in$^2$ and 30 gms/in$^2$, respectively. The Loft-Soft Ratio is then calculated as the ratio of the thickness at 5 gms/in$^2$ divided by the thickness at 30 gms/in$^2$.

Crepe Ratio Method

Creping produces substrates that have patterns of peaks and valleys. Creping can add value to substrates by providing bulk, softness, enhanced ability to remove dirt, enhanced transport of air and water necessary for lather, compressive resiliency, and visually pleasing appearance. Individual substrates can be creped and optionally combined with other substrates, creped or uncreped; also multi-layered articles can be creped. This method can be used to define amount of creping for individual substrates (and their layers) or finished articles. There are a number of different ways to measure the amount of creping. The objective of this method is to measure a bulky, thick dimension representative of the peak-to-nadir dimension of the substrate; and a thin dimension representative of "wall thickness" of the substrate. Preferably, the articles of the present invention comprise a water insoluble substrate comprising a creped nonwoven layer that exhibits a Crepe Ratio of from about 2.5 to about 45 and more preferably, from about 4.5 to about 45 pursuant to the method explained hereafter.

First, the thickness of the substrate to be tested is measured at a pressure of 5 grams/in$^2$ according to the Loft-Soft Method that is discussed above. Several representative pieces of the same substrate are then cut measuring a few square inches. Next, the Flat End Knife Probe (0.02 inches thick×7 mm wide) is attached to the top of an Instron Model 1122 Compression and Tensile tester (or equivalent thereof) in a vertical position. The knife end plane is defined by the 0.0200 inch×7 mm rectangular dimension being parallel to the base plate. An Instron Serial Number 445 load cell (with 100 gms full scale load setting) is calibrated with the top plate in position. The Instron tester is run in compression mode at 0.20 inches/minute rate of descent. The apparatus can be computer or manually controlled so long as the final compression reaches a minimum of 25 grams force and data is collected sufficiently rapidly (computer assisted recommended) to determine the height at various compression values during descent. The top plate is then moved down until the knife end establishes contact with the base plate and the zero point height is set. The knife flat end and base plate must be parallel, making contact at all points simultaneously. The knife probe is retracted to a position above the base plate allowing sufficient space to interpose a substrate. The substrate is then placed on the base plate so that the descending Flat End Knife Probe can descend for the longest possible time without contacting any portion of the substrate. The Instron is then run so as to compress this trough portion of the sample with the knife blade. The sample should be maneuvered during the slow descent of the knife blade to ensure the thinnest possible substrate dimension is being measured. This is the wall thickness. The Instron is then run until a force of about 50 grams is reached during which the height and force are being continuously recorded, preferably by computer print out. Additional substrate samples are similarly tested in order to establish a reliable average. The average height above the base plate at a compression value of 10 grams force is then recorded. The Crepe Ratio is then determined to be the ratio of the substrate thickness at 5 grams/in$^2$ measured by the Loft-Soft Ratio Method, divided by the thickness measured with the Flat End Knife Probe at 10 grams force.

Viscosity Methods

The log viscosity ratio value, i.e., log [(η @ 25° C.)/(η @ 60–200° C.)], that is used herein to characterize the "hot-melt" character of the cleansing component of the articles of the present invention is determined as follows. The individual viscosities, η, are determined at the respective temperatures using a viscometer (e.g., commercially available from TA Instruments, model number AR1000). The measurements are made with a parallel plate having a diameter of 40 mm and a gap of 1.25 mm. First, the cleansing component sample is loaded onto the rheometer plate with the plate set to the higher temperature of interest +20° C. (e.g. if interested in ratio between viscosities at 60° C. and 25° C., the plate would be set to 80° C.) and the measurement set to commence after 180 seconds equilibration. The viscosity is measured using a rotation at a constant stress of 50 Pa over a temperature sweep from the higher temperature of interest +20° C. down to 20° C. with the temperature changing at a rate of 1° C. every 10 seconds. The viscosities of interest can be read from the resultant temperature viscosity curve.

As would be apparent to a skilled artisan, if the viscometer stops during the cooling experiment due to the sample becoming too viscous, the highest viscosity recorded before the experiment stopped should be used for the lower temperature viscosity value in the ratio or the experiment should be repeated using a higher stress, smaller diameter plate or rheometer with higher torque capability.

The method used to determine the complex viscosity at 25° C. is as follows: The cleansing component sample should first be prepared by cooling it at a rate equivalent to that used when coating the component onto a substrate during production of finished articles to ensure that the sample is in a representative physical form. The complex viscosity of the sample is measured using a rheometer such as an AR1000 from TA instruments. The cleansing component is loaded onto the rheometer plate with the plate set to 25° C. The measurement is taken using a parallel plate of 40 mm diameter and a gap of 400 μm. The complex viscosity is measured under a constant 1 Pa stress oscillation at 2.5 Hz and the reading taken after 30 seconds equilibration. As is obvious to a skilled artisan, if the sample is too viscous to give a reading under these conditions, increasing stress should be used until a reading can be made and as long as the stress remains in the linear viscoelastic region.

THERAPEUTIC BENEFIT COMPONENT

In certain embodiments of the present invention, the articles essentially comprise a therapeutic benefit component. This benefit component is disposed adjacent to the water insoluble substrate and comprises from about 10% to about 1000%, more preferably, from about 10% to about 500%, and most preferably from about 10% to about 250%, by weight of the water insoluble substrate, of a therapeutic benefit agent. In particular, the therapeutic benefit component may be disposed adjacent to the first creped nonwoven layer or any additional layers of the water insoluble substrate. Preferably, the therapeutic benefit agent is selected from the group consisting of hydrophobic conditioning agents, hydrophilic conditioning agents, structured conditioning agents, and combinations thereof.

Hydrophobic Conditioning Agents

The articles of the present invention may comprise one or more hydrophobic conditioning agents which are useful for providing a conditioning benefit to the skin or hair during the use of the article. The articles of present invention preferably comprise from about 0.5% to about 1,000%, more preferably from about 1% to about 200%, and most preferably from about 10% to about 100%, by weight of the water insoluble substrate, of a hydrophobic conditioning agent.

The hydrophobic conditioning agent may be selected from one or more hydrophobic conditioning agents such that the weighted arithmetic mean solubility parameter of the hydrophobic conditioning agent is less than or equal to 10.5. It is recognized, based on this mathematical definition of solubility parameters, that it is possible, for example, to achieve the required weighted arithmetic mean solubility parameter, i.e., less than or equal to 10.5, for a hydrophobic conditioning agent comprising two or more compounds if one of the compounds has an individual solubility parameter greater than 10.5.

Solubility parameters are well known to the formulation chemist of ordinary skill in the art and are routinely used as a guide for determining compatibility's and solubilities of materials in the formulation process.

The solubility parameter of a chemical compound, δ, is defined as the square root of the cohesive energy density for that compound. Typically, a solubility parameter for a compound is calculated from tabulated values of the additive group contributions for the heat of vaporization and molar volume of the components of that compound, using the following equation:

$$\delta = \left[ \frac{\sum_i E_i}{\sum_i m_i} \right]^{1/2}$$

wherein $\Sigma_i E_i$=the sum of the heat of vaporization additive group contributions, and $\Sigma_i m_i$=the sum of the molar volume additive group contributions Standard tabulations of heat of vaporization and molar volume additive group contributions for a wide variety of atoms and groups of atoms are collected in Barton, A. F. M. *Handbook of Solubility Parameters*, CRC Press, Chapter 6, Table 3, pp. 64–66 (1985), which is incorporated by reference herein in its entirety. The above solubility parameter equation is described in Fedors, R. F., "A Method for Estimating Both the Solubility Parameters and Molar Volumes of Liquids", *Polymer Engineering and Science*, vol. 14, no. 2, pp. 147–154 (February 1974), which is incorporated by reference herein in its entirety.

Solubility parameters obey the law of mixtures such that the solubility parameter for a mixture of materials is given by the weighted arithmetic mean (i.e. the weighted average) of the solubility parameters for each component of that mixture. See, *Handbook of Chemistry and Physics*, 57th edition, CRC Press, p. C-726 (1976–1977).

Formulation chemists typically report and use solubility parameters in units of $(cal/cm^3)^{1/2}$. The tabulated values of additive group contributions for heat of vaporization in the *Handbook of Solubility Parameters* are reported in units of kJ/mol. However, these tabulated heat of vaporization values are readily converted to cal/mol using the following well-known relationships:

1 J/mol=0.239006 cal/mol and 1000 J=1 kJ.

See Gordon, A. J. et al., *The Chemist's Companion*, John Wiley & Sons, pp. 456–463, (1972).

Solubility parameters have also been tabulated for a wide variety of chemical materials. Tabulations of solubility parameters are found in the above-cited *Handbook of Solubility Parameters*. Also, see "Solubility Effects In Product, Package, Penetration, And Preservation", C. D. Vaughan, *Cosmetics and Toiletries*, vol. 103, October 1988, pp.47–69.

Nonlimiting examples of hydrophobic conditioning agents include those selected from the group consisting of mineral oil, petrolatum, lecithin, hydrogenated lecithin, lanolin, lanolin derivatives, C7–C40 branched chain hydrocarbons, C1–C30 alcohol esters of C1–C30 carboxylic acids, C1–C30 alcohol esters of C2–C30 dicarboxylic acids, monoglycerides of C1–C30 carboxylic acids, diglycerides of C1–C30 carboxylic acids, triglycerides of C1–C30 carboxylic acids, ethylene glycol monoesters of C1–C30 carboxylic acids, ethylene glycol diesters of C1–C30 carboxylic acids, propylene glycol monoesters of C1–C30 carboxylic acids, propylene glycol diesters of C1–C30 carboxylic acids, C1–C30 carboxylic acid monoesters and polyesters of sugars, polydialkylsiloxanes, polydiarylsiloxanes, polyalkarylsiloxanes, cylcomethicones having 3 to 9 silicon atoms, vegetable oils, hydrogenated vegetable oils, polypropylene glycol C4–C20 alkyl ethers, di C8–C30 alkyl ethers, and combinations thereof.

Mineral oil, which is also known as petrolatum liquid, is a mixture of liquid hydrocarbons obtained from petroleum. See The Merck Index, Tenth Edition, Entry 7048, p. 1033 (1983) and International Cosmetic Ingredient Dictionary, Fifth Edition, vol. 1, p.415–417(1993).

Petrolatum, which is also known as petroleum jelly, is a colloidal system of nonstraight-chain solid hydrocarbons and high-boiling liquid hydrocarbons, in which most of the liquid hydrocarbons are held inside the micelles. See The Merck Index, Tenth Edition, Entry 7047, p. 1033 (1983); Schindler, *Drug. Cosmet. Ind.*, 89, 36–37, 76, 78–80, 82 (1961); and International Cosmetic Ingredient Dictionary, Fifth Edition, vol. 1, p. 537 (1993).

Lecithin is also useful as a hydrophobic conditioning agent. It is a naturally occurring mixture of the diglycerides of certain fatty acids, linked to the choline ester of phosphoric acid.

Straight and branched chain hydrocarbons having from about 7 to about 40 carbon atoms are useful herein. Nonlimiting examples of these hydrocarbon materials include dodecane, isododecane, squalane, cholesterol, hydrogenated polyisobutylene, docosane (i.e. a $C_{22}$ hydrocarbon), hexadecane, isohexadecane (a commercially available hydrocarbon sold as Permethyl® 101A by Presperse, South Plainfield, N.J.). Also useful are the C7–C40 isoparaffins, which are C7–C40 branched hydrocarbons. Polydecene, a branched liquid hydrocarbon, is also useful herein and is commercially available under the tradenames Puresyn 100® and Puresyn 3000® from Mobile Chemical (Edison, N.J.).

Also useful are C1–C30 alcohol esters of C1–C30 carboxylic acids and of C2–C30 dicarboxylic acids, including straight and branched chain materials as well as aromatic derivatives. Also useful are esters such as monoglycerides of C1–C30 carboxylic acids, diglycerides of C1–C30 carboxylic acids, triglycerides of C1–C30 carboxylic acids, ethylene glycol monoesters of C1–C30 carboxylic acids, ethylene glycol diesters of C1–C30 carboxylic acids, propylene glycol monoesters of C1–C30 carboxylic acids, and propylene glycol diesters of C1–C30 carboxylic acids. Straight chain, branched chain and aryl carboxylic acids are included herein. Also useful are propoxylated and ethoxylated derivatives of these materials. Nonlimiting examples include diisopropyl sebacate, diisopropyl adipate, isopropyl myristate, isopropyl palmitate, myristyl propionate, ethylene glycol distearate, 2-ethylhexyl palmitate, isodecyl neopentanoate, di-2-ethylhexyl maleate, cetyl palmitate, myristyl myristate, stearyl stearate, cetyl stearate, behenyl behenrate, dioctyl maleate, dioctyl sebacate, diisopropyl adipate, cetyl octanoate, diisopropyl dilinoleate, carpylic/capric triglyceride, PEG-6 caprylic/capric triglyceride, PEG-8 caprylic/capric triglyceride, and combinations thereof.

Also useful are various C1–C30 monoesters and polyesters of sugars and related materials. These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. Examples of solid esters include: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio. A preferred solid material is sucrose polyester in which the degree of esterification is 7–8, and in which the fatty acid moieties are C18 mono- and/or di-unsaturated and behenic, in a molar ratio of unsaturates: behenic of 1:7 to 3:5. A particularly preferred solid sugar polyester is the octaester of sucrose in which there are about 7 behenic fatty acid moieties and about 1 oleic acid moiety in the molecule. Other materials include cottonseed oil or soybean oil fatty acid esters of sucrose. The ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985.

Nonvolatile silicones such as polydialkylsiloxanes, polydiarylsiloxanes, and polyalkarylsiloxanes are also useful oils. These silicones are disclosed in U.S. Pat. No. 5,069,897, to Orr, issued Dec. 3, 1991. The polyalkylsiloxanes correspond to the general chemical formula $R_3SiO[R_2SiO]_xSiR_3$ wherein R is an alkyl group (preferably R is methyl or ethyl, more preferably methyl) and x is an integer up to about 500, chosen to achieve the desired molecular weight. Commercially available polyalkylsiloxanes include the polydimethylsiloxanes, which are also known as dimethicones, nonlimiting examples of which include the Vicasil® series sold by General Electric Company and the Dow Corning® 200 series sold by Dow Corning Corporation. Specific examples of polydimethylsiloxanes useful herein include Dow Corning® 225 fluid having a viscosity of 10 centistokes and a boiling point greater than 200° C., and Dow Corning® 200 fluids having viscosities of 50, 350, and 12,500 centistokes, respectively, and boiling points greater than 200° C. Also useful are materials such as trimethylsiloxysilicate, which is a polymeric material corresponding to the general chemical formula [(CH$_2$)$_3$SiO$_{1/2}$]$_x$[SiO$_2$]y, wherein x is an integer from about 1 to about 500 and y is an integer from about 1 to about 500. A commercially available trimethylsiloxysilicate is sold as a mixture with dimethicone as Dow Corning® 593 fluid. Also useful herein are dimethiconols, which are hydroxy terminated dimethyl silicones. These materials can be represented by the general chemical formulas R$_3$SiO[R$_2$SiO]$_x$SiR$_2$OH and HOR$_2$SiO[R$_2$SiO]$_x$SiR$_2$OH wherein R is an alkyl group (preferably R is methyl or ethyl, more preferably methyl) and x is an integer up to about 500, chosen to achieve the desired molecular weight. Commercially available dimethiconols are typically sold as mixtures with dimethicone or cyclomethicone (e.g. Dow Corning® 1401, 1402, and 1403 fluids). Also useful herein are polyalkylaryl siloxanes, with polymethylphenyl siloxanes having viscosities from about 15 to about 65 centistokes at 25° C. being preferred. These materials are available, for example, as SF 1075 methylphenyl fluid (sold by General Electric Company) and 556 Cosmetic Grade phenyl trimethicone fluid (sold by Dow Corning Corporation). Alkylated silicones such as methyldecyl silicone and methyloctyl silicone are useful herein and are commercially available from General Electric Company. Also useful herein are alkyl modified siloxanes such as alkyl methicones and alkyl dimethicones wherein the alkyl chain contains 10 to 50 carbons. Such siloxanes are commercially available under the tradenames ABIL WAX 9810® (C$_{24}$–C$_{28}$ alkyl methicone) (sold by Goldschmidt) and SF1632 (cetearyl methicone)(sold by General Electric Company).

Vegetable oils and hydrogenated vegetable oils are also useful herein. Examples of vegetable oils and hydrogenated vegetable oils include safflower oil, castor oil, coconut oil, cottonseed oil, menhaden oil, palm kernel oil, palm oil, peanut oil, soybean oil, rapeseed oil, linseed oil, rice bran oil, pine oil, sesame oil, sunflower seed oil, hydrogenated safflower oil, hydrogenated castor oil, hydrogenated coconut oil, hydrogenated cottonseed oil, hydrogenated menhaden oil, hydrogenated palm kernel oil, hydrogenated palm oil, hydrogenated peanut oil, hydrogenated soybean oil, hydrogenated rapeseed oil, hydrogenated linseed oil, hydrogenated rice bran oil, hydrogenated sesame oil, hydrogenated sunflower seed oil, and mixtures thereof.

Also useful are C4–C20 alkyl ethers of polypropylene glycols, C1–C20 carboxylic acid esters of polypropylene glycols, and di-C8–C30 alkyl ethers. Nonlimiting examples of these materials include PPG-14 butyl ether, PPG-15 stearyl ether, dioctyl ether, dodecyl octyl ether, and mixtures thereof.

Hydrophobic chelating agents are also useful herein as hydrophobic conditioning agents. Suitable agents are described in U.S. Pat. No. 4,387,244, issued to Scanlon et al. on Jun. 7, 1983, and copending U.S. patent application Ser. Nos. 09/258,747 and 09/259,485, filed in the names of Schwartz et al. on Feb. 26, 1999.

Hydrophilic Conditioning Agents

The articles of the present invention may optionally comprise one or more hydrophilic conditioning agents. Nonlimiting examples of hydrophilic conditioning agents include those selected from the group consisting of polyhydric alcohols, polypropylene glycols, polyethylene glycols, ureas, pyrolidone carboxylic acids, ethoxylated and/or propoxylated C3–C6 diols and triols, alpha-hydroxy C2–C6 carboxylic acids, ethoxylated and/or propoxylated sugars, polyacrylic acid copolymers, sugars having up to about 12 carbons atoms, sugar alcohols having up to about 12 carbon atoms, and mixtures thereof. Specific examples of useful hydrophilic conditioning agents include materials such as urea; guanidine; glycolic acid and glycolate salts (e.g., ammonium and quaternary alkyl ammonium); lactic acid and lactate salts (e.g., ammonium and quaternary alkyl ammonium); sucrose, fructose, glucose, eruthrose, erythritol, sorbitol, mannitol, glycerol, hexanetriol, propylene glycol, butylene glycol, hexylene glycol, and the like; polyethylene glycols such as PEG-2, PEG-3, PEG-30, PEG-50, polypropylene glycols such as PPG-9, PPG-12, PPG-15, PPG-17, PPG-20, PPG-26, PPG-30, PPG-34; alkoxylated glucose; hyaluronic acid; cationic skin conditioning polymers (e.g., quaternary ammonium polymers such as Polyquaternium polymers); and mixtures thereof. Glycerol, in particular, is a preferred hydrophilic conditioning agent in the articles of the present invention. Also useful are materials such as aloe vera in any of its variety of forms (e.g., aloe vera gel), chitosan and chitosan derivatives, e.g., chitosan lactate, lactamide monoethanolamine; acetamide monoethanolamine; and mixtures thereof. Also useful are propoxylated glycerols as described in propoxylated glycerols described in U.S. Pat. No. 4,976,953, to Orr et al., issued Dec. 11, 1990.

The therapeutic benefit component may be made into a variety of forms. In one embodiment of the present invention, the therapeutic benefit component is in the form of an emulsion. For instance, oil-in-water, water-in-oil, water-in-oil-in-water, and oil-in-water-in-silicone emulsions are useful herein. As used in the context of emulsions, "water" may refer not only to water but also water soluble or water miscible agents like glycerin.

Preferred therapeutic benefit components comprise an emulsion, which further comprises an aqueous phase and an oil phase. As will be understood by the skilled artisan, a given component will distribute primarily into either the aqueous or oil phase, depending on the water solubility/ dispersibility of the therapeutic benefit agent in the component. In one embodiment, the oil phase comprises one or more hydrophobic conditioning agents. In another embodiment, the aqueous phase comprises one or more hydrophilic conditioning agents.

Therapeutic benefit components of the present invention, which are emulsion form, generally contain an aqueous phase and an oil or lipid phase. Suitable oils or lipids may be derived from animals, plants, or petroleum and may be natural or synthetic (i.e., man-made). Such oils are discussed above in the Hydrophobic Conditioning Agents section. Suitable aqueous phase components include the Hydrophilic Conditioning Agents, which are discussed above. Preferred emulsion forms include water-in-oil emulsions, water-in-silicone emulsions, and other inverse emulsions. Additionally, preferred emulsions also contain a hydrophilic conditioning agent such as glycerin such that a glycerin-in-oil emulsion results.

Therapeutic benefit components in emulsion form will preferably further contain from about 1% to about 10%, more preferably from about 2% to about 5%, of an emulsifier, based on the weight of therapeutic benefit component. Emulsifiers may be nonionic, anionic or cationic. Suitable emulsifiers are disclosed in, for example, U.S. Pat. No. 3,755,560, issued Aug. 28, 1973, Dickert et al.; U.S. Pat.

No. 4,421,769, issued Dec. 20, 1983, Dixon et al.; and McCutcheon's *Detergents and Emulsifiers,* North American Edition, pages 317–324 (1986). Therapeutic benefit components in emulsion form may also contain an anti-foaming agent to minimize foaming upon application to the skin. Anti-foaming agents include high molecular weight silicones and other materials well known in the art for such use.

The therapeutic benefit component may also be in the form of a microemulsion. As used herein, "microemulsion" refers to thermodynamic stable mixtures of two immiscible solvents (one apolar and the other polar) stabilized by an amphiphilic molecule, a surfactant. Preferred microemulsions include water-in-oil microemulsions.

Structured Conditioning Agents

The therapeutic benefit component may comprise structured conditioning agents. Suitable structured conditioning agents include, but are not limited to, vesicular structures such as ceramides, liposomes, and the like.

In another embodiment, the therapeutic benefit agents of the benefit component are comprised within a coacervate-forming composition. Preferably, the coacervate-forming composition comprises a cationic polymer, an anionic surfactant, and a dermatologically acceptable carrier for the polymer and surfactant. The cationic polymer may be selected from the group consisting of natural backbone quaternary ammonium polymers, synthetic backbone quaternary ammonium polymers, natural backbone amphoteric type polymers, synthetic backbone amphoteric type polymers, and combinations thereof.

More preferably, the cationic polymer is selected from the group consisting of natural backbone quaternary ammonium polymers selected from the group consisting of Polyquaternium-4, Polyquaternium-10, Polyquaternium-24, PG-hydroxyethylcellulose alkyldimonium chlorides, guar hydroxypropyltrimonium chloride, hydroxypropylguar hydroxypropyltrimonium chloride, and combinations thereof; synthetic backbone quaternary ammonium polymers selected from the group consisting of Polyquaternium-2, Polyquaternium-6, Polyquaternium-7, Polyquaternium-11, Polyquaternium-16, Polyquaternium-17, Polyquaternium-18, Polyquaternium-28, Polyquaternium-32, Polyquaternium-37, Polyquaternium-43, Polyquaternium-44, Polyquaternium-46, polymethacylamidopropyl trimonium chloride, acrylamidopropyl trimonium chloride/acrylamide copolymer, and combinations thereof; natural backbone amphoteric type polymers selected from the group consisting of chitosan, quaternized proteins, hydrolyzed proteins, and combinations thereof; synthetic backbone amphoteric type polymers selected from the group consisting of Polyquaternium-22, Polyquaternium-39, Polyquaternium-47, adipic acid/dimethylaminohydroxypropyl diethylenetriamine copolymer, polyvinylpyrrolidone/dimethylyaminoethyl methacyrlate copolymer, vinylcaprolactam/polyvinylpyrrolidone/dimethylaminoethylmethacrylate copolymer, vinaylcaprolactam/polyvinylpyrrolidone/dimethylaminopropylmethacrylamide terpolymer, polyvinylpyrrolidone/dimethylaminopropylmethacrylamide copolymer, polyamine, and combinations thereof; and combinations thereof. Even more preferably, the cationic polymer is a synthetic backbone amphoteric type polymer. Even still more preferably, the cationic polymer is a polyamine.

When the cationic polymer is a polyamine, it is preferred that the cationic polyamine polymer be selected from the group consisting of polyethyleneimines, polyvinylamines, polypropyleneimines, polylysines and combinations thereof. Even more preferably, the cationic polyamine polymer is a polyethyleneimine.

In certain embodiments in which the cationic polymer is a polyamine, the polyamine may be hydrophobically or hydrophilically modified. In this instance, the cationic polyamine polymer is selected from the group consisting of benzylated polyamines, ethoxylated polyamines, propoxylated polyamines, alkylated polyamines, amidated polyamines, esterified polyamines and combinations thereof. The coacervate-forming composition comprises from about 0.01% to about 20%, more preferably from about 0.05% to about 10%, and most preferably from about 0.1% to about 5%, by weight of the coacervate-forming composition, of the cationic polymer.

Suitable anionic surfactants include those discussed above as related to the "cleansing component." Preferably, for the coacervate-forming composition, the anionic surfactant is selected from the group consisting of sarcosinates, glutamates, sodium alkyl sulfates, ammonium alkyl sulfates, sodium alkyleth sulfates, ammonium alkyleth sulfates, ammonium laureth-n-sulfates, sodium laureth-n-sulfates, isethionates, glycerylether sulfonates, sulfosuccinates and combinations thereof. More preferably, the anionic surfactant is selected from the group consisting of sodium lauroyl sarcosinate, monosodium lauroyl glutamate, sodium alkyl sulfates, ammonium alkyl sulfates, sodium alkyleth sulfates, ammonium alkyleth sulfates, and combinations thereof.

Suitable coacervate-forming compositions are further described in copending U.S. patent applications Ser. Nos. 09/397,747, filed in the name of Schwartz et al.; 09/397,746, filed in the name of Heinrich et al.; 09/397,712, filed in the name of Schwartz et al.; 09/397,723, filed in the name of Heinrich et al.; and 09/397,722, filed in the name of Venkitaraman et al.; each of which were filed on Sep. 16, 1999.

Alternatively, the coacervate-forming composition may comprise an anionic polymer, a cationic surfactant, and a dermatologically acceptable carrier for the polymer and surfactant. The anionic polymer may be selected from the group consisting of polyacrylic acid polymers, polyacrylamide polymers, copolymers of acrylic acid, acrylamide, and other natural or synthetic polymers (e.g., polystyrene, polybutene, polyurethane, etc.), naturally derived gums, and combinations thereof. Suitable gums include alginates (e.g., propylene glycol alginate), pectins, chitosans (e.g., chitosan lactate), and modified gums (e.g., starch octenyl succinate), and combinations thereof. More preferably, the anionic polymer is selected from the group consisting of polyacrylic acid polymers, polyacrylamide polymers, pectins, chitosans, and combinations thereof. Preferred articles of the present invention comprise from about 0.01% to about 20%, more preferably from about 0.05% to about 10%, and most preferably from about 0.1% to about 5%, by weight of the coacervate-forming composition, of the anionic polymer. Suitable cationic surfactants include, but are not limited to, those discussed herein.

The therapeutic benefit component of the article is suitable for providing therapeutic or aesthetic skin or hair benefits by deposition onto such surfaces of not only conditioning agents but also various agents including, but not limited to, anti-acne actives, anti-wrinkle actives, anti-microbial actives, anti-fungal actives, anti-inflammatory actives, topical anesthetic actives, artificial tanning agents and accelerators, anti-viral agents, enzymes, sunscreen actives, anti-oxidants, skin exfoliating agents, and combinations thereof.

It should also be understood that the therapeutic benefit component may be contained within the cleansing component of the present invention or vice versa such that they form a unitary component with indistinguishable ingredients.

Surface to Saturation Ratio Methodology

When a therapeutic benefit component is included in the article, the articles have the therapeutic benefit component substantially on the surface of the substrate. By "substantially on the surface of the substrate" is meant that the surface to saturation ratio is greater than about 1.25, preferably greater than about 1.5, more preferably greater than about 2.0, even more preferably greater than about 2.25, and most preferably greater than 2.5. The surface to saturation ratio is a ratio of the measurement of benefit agent on the surface of the substrate. These measurements are obtained from Attenuated Total Reflectance (ATR) FT-IR Spectroscopy the use of which is well known to one skilled in the art of analytical chemistry.

Many conventional methods of application of conditioning agents to substrates employ processes and/or product rheologies unsuitable for the purposes of the present invention. For example, a process to dip the substrate web in a fluid bath of conditioning agent and then squeeze the substrate web through metering rolls, so called "dip and nip" processing, applies conditioning agent through the entire substrate and therefore does not afford opportunity for effective direct transfer of the composition off the cloth and onto another surface during use. Furthermore, many of the articles of the present invention utilize sufficient loadings of conditioning agent onto substrates to provide an effective whole body benefit, usually requiring about 100–200% loading rates based on the weight of the dry substrate. Known personal care implements that use these high loading levels essentially avoid dealing with aesthetic issues that can result from these high loadings by distributing the loading evenly throughout the substrate, including the substrate interior. Applicants have surprisingly found that high loadings of conditioning agent can be maintained on the surface of the article, thus advantageously affording opportunity for direct transfer of the benefit agents from the substrate to the surface to be treated during use, while delivering improved aesthetics by the compositions of the present invention.

The procedure to obtain the measurements is as follows:

Instrumental Setup:

A BioRad FTS-7 spectrometer, manufactured by Bio Rad Labs, Digital Laboratory Division, located in Cambridge, Mass., is used to collect the infrared spectra. Typically, the measurements consist of 100 scans at $4\ cm^{-1}$ resolution. The collection optics consist of a flat 60 deg ZnSe ATR crystal, manufactured by Graseby Specac, Inc., located in Fairfield, Conn. Data is collected at 25° C. and analyzed using Grams 386 software, distributed by Galactic Industries Corp., located in Salem, N.H. Prior to measurement the crystal is cleaned with a suitable solvent. The sample is placed onto the ATR crystal and held under constant 4 kilogram weight.

Experimental Procedure:

(1) Measure the reference (background) spectrum of the cleaned, air dried cell.

(2) First, select a substrate with no benefit agents applied to it, the substrate selected comprising the external surface of the article. Place substrate on top of the ATR crystal., external surface against the crystal. First lay the substrate flat on the measuring platform. Then place a 4 kg. weight on top of the substrate. Then, measure the spectrum (typically 100 scans at $4\ cm^{-1}$ resolution). The substrate acts as an internal standard because the absorbancy of the substrate alone is thus identified. Identify the main substrate peaks and wavenumbers.

(3) Repeat the procedure for the substrate of the article with benefit agent applied to it. Identify the primary benefit agent's peak heights, which are the highest observed peaks that either do not correspond to a substrate peak as observed previously; or which may correspond to a previously observed substrate peak but which exhibit the greatest percentage increase in absorbance due to presence of the conditioning agent. Record the wavenumber and absorbance of several benefit agent peaks.

(4) Select the substrate peak from the spectra determined in step 3 which occurs at a wavenumber determined in step 2, but which does not correspond to one of the primary benefit agent peaks selected in step 3. Record the wavenumber selected and the absorbance from the absorbance spectrum in step 3.

(5) Calculate the ratio of each benefit agent's peak height determined in step 3 to the substrate's peak height determined in step 4. The highest number of the group represents the surface to saturation ratio for the article.

The following contain some examples:

| Substrate* | Substrate Peak and Peak Ht. | Conditioner | Conditioner Peak Ht. | Ratio |
|---|---|---|---|---|
| Batting (blend of polyester heat bonded with 70% PET/PE bicomponent fiber) | 0.0865 (C=O) Peak at $1710\ cm^{-1}$ | Glycerin (C—O Peak at $1030\ cm^{-1}$) | 0.181 | 2.09 |
| Batting (blend of polyester heat bonded with 70% PET/PE bicomponent fiber) | 0.0865 (C=O) Peak at $1710\ cm^{-1}$ | Hydrocarbon (C—H Peak at $2923\ cm^{-1}$) | 0.160 | 1.85 |
| 70% Rayon/30% Polyester, hydroentangled | 0.0333 (C=O) Peak at $1710\ cm^{-1}$ | Glycerin (C—O Peak at $1030\ cm^{-1}$) | 0.0684 | 2.05 |

*Substrates of these types are readily available, for example from PGI Nonwovens, Benson, NC Moisture Retention Methodology As described above, the articles of the present invention are considered to be "substantially dry". As used herein, "substantially dry" means that the articles of the present invention exhibit a Moisture Retention of less than about 0.95 gms, preferably less than about 0.75 gms, even more preferably, less than about 0.5 gms, even more preferably less than about 0.25 gms, even still more preferably less than about 0.15 gms, and most preferably, less than about 0.1 gms. The Moisture Retention is indicative of the dry feel that users perceive upon touching the articles of the present invention as opposed to the feel of "wet" wipes.

In order to determine the Moisture Retention of the present articles and other disposable substrate-based products, the following equipment and materials are needed.

| | |
|---|---|
| Bounty White Paper Towel | Procter & Gamble SKU 37000 63037 Basis Weight = 42.14 gsm |
| Balance | Accurate to 0.0 g |
| Lexan | 0.5" thickness |

-continued

| | |
|---|---|
| | large enough to cover samples completely and weighs 1000 g |
| Weight | A 2000 g weight or combination to equal 2000 g |

Next, weigh two paper towels separately and record each weight. Place one paper towel on flat surface (e.g., lab bench). Place the sample article on top of that towel. Place the other paper towel on top of sample article. Next, place the Lexan and then the 2000 g weight(s) on top of the sandwiched sample article. Wait 1 minute. After the minute, remove weight(s) and Lexan. Weigh the top and bottom paper towel and record the weight.

Calculate the Moisture Retention by subtracting the initial paper towel weight from the final weight (after 1 minute) for both the top and bottom paper towels. Add the weight differences obtained for the top and bottom paper towels. Assuming multiple articles are tested, average the total weight differences to obtain the Moisture Retention.

MULTIPLE ARTICLE EMBODIMENT

The articles of the present invention may also be packaged individually or with additional articles suitable for providing separate benefits not provided by the primary article, e.g., aesthetic, therapeutic, functional, or otherwise, thereby forming a personal care kit. The additional article of this personal care kit preferably comprises a water insoluble substrate comprising at least one layer and either a cleansing component containing a lathering surfactant or a therapeutic benefit component disposed onto or impregnated into that layer of the substrate of the additional article.

The additional article of the present invention may also serve a functional benefit in addition to or in lieu of a therapeutic or aesthetic benefit. For instance, the additional article may be useful as a drying implement suitable for use to aid in the removal of water from the skin or hair upon completion of a showering or bathing experience.

MULTIPLE CHAMBERED EMBODIMENT

The articles of the present invention may also comprise one or more chambers. Such chambers or compartments result from the connection (e.g., bonding) of the substrate layers to one another at various loci to define enclosed areas. These chambers are useful, e.g., for separating various article components from one another, e.g., the surfactant-containing cleansing component from a conditioning agent. The separated article components which provide a therapeutic or aesthetic or cleansing benefit may be released from the chambers in a variety of ways including, but not limited to, solubilization, emulsification, mechanical transfer, puncturing, popping, bursting, squeezing of the chamber or even peeling away a substrate layer which composes a portion of the chamber.

OPTIONAL COMPONENTS

The articles of the present invention may contain a variety of other components such as are conventionally used in a given product type provided that they do not unacceptably alter the benefits of the invention. These optional components should be suitable for application to human skin and hair, that is, when incorporated into the article they are suitable for use in contact with human skin without undue toxicity, incompatibility, instability, allergic response, and the like, within the scope of sound medical or formulator's judgment. The CTFA Cosmetic Ingredient Handbook, Second Edition (1992) describes a wide variety of nonlimiting cosmetic and pharmaceutical ingredients commonly used in the skin care industry, which are suitable for use in the articles of the present invention. Examples of these ingredient classes include: enzymes, abrasives, skin exfoliating agents, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents (e.g., resorcinol, sulfur, salicylic acid, erythromycin, zinc, etc.), anti-caking agents, antifoaming agents, additional antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), humectants, opacifying agents, pH adjusters, propellants, reducing agents, sequestrants, skin bleaching agents (or lightening agents) (e.g., hydroquinone, kojic acid, ascorbic acid, magnesium ascorbyl phosphate, ascorbyl glucosamine), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, including agents for preventing, retarding, arresting, and/or reversing skin wrinkles (e.g., alpha-hydroxy acids such as lactic acid and glycolic acid and beta-hydroxy acids such as salicylic acid), thickeners, hydrocolloids, particular zeolites, and vitamins and derivatives thereof (e.g. tocopherol, tocopherol acetate, beta carotene, retinoic acid, retinol, retinoids, retinyl palmitate, niacin, niacinamide, and the like). The articles of the present invention may include carrier components such as are known in the art. Such carriers can include one or more compatible liquid or solid filler diluents or vehicles which are suitable for application to skin or hair.

The articles of the present invention may optionally contain one or more of such optional components. Preferred articles optionally contain a safe and effective amount of therapeutic benefit component comprising a therapeutic benefit agent selected from the group consisting of vitamin compounds, skin treating agents, anti-acne actives, anti-wrinkle actives, anti-skin atrophy actives, anti-inflammatory actives, topical anesthetics, artificial tanning actives and accelerators, anti-microbial actives, anti-fungal actives, sunscreen actives, anti-oxidants, skin exfoliating agents, and combinations thereof. As used herein, "a safe and effective amount" means an amount of a compound or component sufficient to significantly induce a positive effect or benefit, but low enough to avoid serious side effects, (e.g., undue toxicity or allergic reaction), i.e., to provide a reasonable benefit to risk ratio, within the scope of sound medical judgment.

The optional components useful herein can be categorized by their therapeutic or aesthetic benefit or their postulated mode of action. However, it is to be understood that the optional components useful herein can in some instances provide more than one therapeutic or aesthetic benefit or operate via more than one mode of action. Therefore, classifications herein are made for the sake of convenience and are not intended to limit the component to that particular application or applications listed. Also, when applicable, the pharmaceutically-acceptable salts of the components are useful herein.

Vitamin Compounds

The present articles may comprise vitamin compounds, precursors, and derivatives thereof. These vitamin compounds may be in either natural or synthetic form. Suitable vitamin compounds include, but are not limited to, Vitamin A (e.g., beta carotene, retinoic acid, retinol, retinoids, retinyl palmitate, retinyl proprionate, etc.), Vitamin B (e.g., niacin, niacinamide, riboflavin, pantothenic acid, etc.), Vitamin C (e.g., ascorbic acid, etc.), Vitamin D (e.g., ergosterol, ergocalciferol, cholecalciferol, etc.), Vitamin E (e.g., tocopherol acetate, etc.), and Vitamin K (e.g., phytonadione, menadione, phthiocol, etc.) compounds.

In particular, the articles of the present invention may comprise a safe and effective amount of a vitamin $B_3$ compound. Vitamin $B_3$ compounds are particularly useful for regulating skin condition as described in co-pending U.S. application Ser. No. 08/834,010, filed Apr. 11, 1997 (corresponding to international publication WO 97139733 A1, published Oct. 30, 1997) which is incorporated by reference herein in its entirety. The therapeutic component of the present invention preferably comprise from about 0.01% to about 50%, more preferably from about 0.1% to about 10%, even more preferably from about 0.5% to about 10%, and still more preferably from about 1% to about 5%, most preferably from about 2% to about 5%, of the vitamin $B_3$ compound.

As used herein, "vitamin $B_3$ compound" means a compound having the formula:

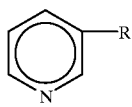

wherein R is —$CONH_2$ (i.e., niacinamide), —COOH (i.e., nicotinic acid) or —$CH_2OH$ (i.e., nicotinyl alcohol); derivatives thereof; and salts of any of the foregoing.

Exemplary derivatives of the foregoing vitamin $B_3$ compounds include nicotinic acid esters, including non-vasodilating esters of nicotinic acid, nicotinyl amino acids, nicotinyl alcohol esters of carboxylic acids, nicotinic acid N-oxide and niacinamide N-oxide.

Examples of suitable vitamin $B_3$ compounds are well known in the art and are commercially available from a number of sources, e.g., the Sigma Chemical Company (St. Louis, Mo.); ICN Biomedicals, Inc. (Irvin, Calif.) and Aldrich Chemical Company (Milwaukee, Wis.).

The vitamin compounds may be included as the substantially pure material, or as an extract obtained by suitable physical and/or chemical isolation from natural (e.g., plant) sources.

Skin Treating Agents

The articles of the present invention may contain one or more skin treating agents. Suitable skin treating agents include those effective for preventing, retarding, arresting, and/or reversing skin wrinkles. Examples of suitable skin treating agents include, but are not limited to, alpha-hydroxy acids such as lactic acid and glycolic acid and beta-hydroxy acids such as salicylic acid.

Anti-Acne Actives

Examples of useful anti-acne actives for the articles of the present invention include, but are not limited to, the keratolytics such as salicylic acid (o-hydroxybenzoic acid), derivatives of salicylic acid such as 5-octanoyl salicylic acid, and resorcinol; retinoids such as retinoic acid and its derivatives (e.g., cis and trans); sulfur-containing D and L amino acids and their derivatives and salts, particularly their N-acetyl derivatives, a preferred example of which is N-acetyl-L-cysteine; lipoic acid; antibiotics and antimicrobials such as benzoyl peroxide, octopirox, tetracycline, 2,4,4'-trichloro-2'-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; sebostats such as flavonoids; and bile salts such as scymnol sulfate and its derivatives, deoxycholate, and cholate.

Anti-Wrinkle and Anti-Skin Atrophy Actives

Examples of anti-wrinkle and anti-skin atrophy actives useful for the articles of the present invention include, but are not limited to, retinoic acid and its derivatives (e.g., cis and trans); retinol; retinyl esters; niacinamide, salicylic acid and derivatives thereof; sulfur-containing D and L amino acids and their derivatives and salts, particularly the N-acetyl derivatives, a preferred example of which is N-acetyl-L-cysteine; thiols, e.g., ethane thiol; hydroxy acids, phytic acid, lipoic acid; lysophosphatidic acid, and skin peel agents (e.g., phenol and the like).

Non-Steroidal Anti-Inflammatory Actives (NSAIDS)

Examples of NSAIDS useful for the articles of the present invention include, but are not limited to, the following categories: propionic acid derivatives; acetic acid derivatives; fenamic acid derivatives; biphenylcarboxylic acid derivatives; and oxicams. All of these NSAIDS are fully described in U.S. Pat. No. 4,985,459 to Sunshine et al., issued Jan. 15, 1991. Examples of useful NSAIDS include acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Also useful are the steroidal anti-inflammatory drugs including hydrocortisone and the like.

Topical Anesthetics

Examples of topical anesthetic drugs useful for the articles of the present invention include, but are not limited to, benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

Artificial Tanning Actives and Accelerators

Examples of artificial tanning actives and accelerators useful for the articles of the present invention include, but are not limited to, dihydroxyacetaone, tyrosine, tyrosine esters such as ethyl tyrosinate, and phospho-DOPA.

Antimicrobial and Antifungal Actives

Examples of antimicrobial and antifungal actives useful for the articles of the present invention include, but are not limited to, β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorocarbanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xylenol, nystatin, tolnaftate, zinc pyrithione and clotrimazole.

Anti-viral Agents

The articles of the present invention may further comprise one or more anti-viral agents. Suitable anti-viral agents include, but are not limited to, metal salts (e.g., silver nitrate, copper sulfate, iron chloride, etc.) and organic acids (e.g., malic acid, salicylic acid, succinic acid, benzoic acid, etc.). In particular compositions which contain additional suitable anti-viral agents include those described in copending U.S. patent applications Ser. Nos. 09/421,084 (Beerse et al.); 09/421,131 (Biedermann et al.); 09/420,646 (Morgan et al.); and 09/421,179 (Page et al.), which were each filed on Oct. 19, 1999.

Enzymes

The article of the present invention may optionally include one or more enzymes. Preferably, such enzymes are dermatologically acceptable. Suitable enzymes include, but are not limited to, keratinase, protease, amylase, subtilisin, etc.

Sunscreen Actives

Also useful herein are sunscreening actives. A wide variety of sunscreening agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of *Cosmetics Science and Technology*. Nonlimiting examples of sunscreens which are useful in the compositions of the present invention are those selected from the group consisting of 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof. Still other useful sunscreens are those disclosed in U.S. Pat. No. 4,937,370, to Sabatelli, issued Jun. 26, 1990; and U.S. Pat. No. 4,999,186, to Sabatelli et al., issued Mar. 12, 1991. Especially preferred examples of these sunscreens include those selected from the group consisting of 4-N,N-(2-ethylhexyl) methylaminobenzoic acid ester of 2,4-dihydroxybenzophenone, 4-N,N-(2-ethylhexyl) methylaminobenzoic acid ester with 4-hydroxydibenzoylmethane, 4-N,N-(2-ethylhexyl)-methylaminobenzoic acid ester of 2-hydroxy-4-(2-hydroxyethoxy)benzophenone, 4-N,N-(2-ethylhexyl)-methylaminobenzoic acid ester of 4-(2-hydroxyethoxy) dibenzoylmethane, and mixtures thereof. Exact amounts of sunscreens which can be employed will vary depending upon the sunscreen chosen and the desired Sun Protection Factor (SPF) to be achieved. SPF is a commonly used measure of photoprotection of a sunscreen against erythema. See *Federal Register*, Vol. 43, No. 166, pp. 38206–38269, Aug. 25, 1978.

Hydrocolloids

Hydrocolloids may also be optionally included in the articles of the present invention. Hydrocolloids are well known in the art and are helpful in extending the useful life of the surfactants contained in the cleansing component of the present invention such that the articles may last throughout at least one entire showering or bathing experience. Suitable hydrocolloids include, but are not limited to, xanthan gum, carboxymethyl cellulose, hydroxyethyl cellulose, hydroxylpropyl cellulose, methyl and ethyl cellulose, natural gums, gudras guar gum, bean gum, natural starches, deionized starches (e.g., starch octenyl succinate) and the like.

Exothermic Zeolites

Zeolites and other compounds which react exothermically when combined with water may also be optionally included in the articles of the present invention.

Hydrogel Forming Polymeric Gelling Agents

In certain embodiments of the present invention, the articles may optionally comprise an aqueous gel, i.e., a "hydrogel", formed from a hydrogel forming polymeric gelling agent and water. More specifically, the hydrogel is contained within the cleansing component or the therapeutic benefit component of the article. When an aqueous gel is present, the articles preferably comprise from about 0.1% to about 100%, by weight of the water insoluble substrate, more preferably from about 3% to about 50%, and most preferably from about 5% to about 35%, of a hydrogel forming polymeric gelling agent, calculated based on the dry weight of the hydrogel forming polymeric gelling agent.

In general, the hydrogel forming polymeric gelling agent materials of the present invention are at least partially crosslinked polymers prepared from polymerizable, unsaturated acid-containing monomers which are water-soluble or become water-soluble upon hydrolysis. These include monoethylenically unsaturated compounds having at least one hydrophilic radical, including (but not limited to) olefinically unsaturated acids and anhydrides which contain at least one carbon—carbon olefinic double bond. With respect to these monomers, water-soluble means that the monomer is soluble in deionized water at 25° C. at a level of at least 0.2%, preferably at least 1.0%.

Upon polymerization, monomeric units as described above will generally constitute from about 25 mole percent to 99.99 mole percent, more preferably from about 50 mole percent to 99.99 mole percent, most preferably at least about 75 mole percent of the polymeric gelling agent material (dry polymer weight basis), of acid-containing monomers.

The hydrogel forming polymeric gelling agent herein is partially crosslinked to a sufficient degree preferably that is high enough such that the resulting polymer does not exhibit a glass transition temperature (Tg) below about 140° C., and accordingly, the term "hydrogel forming polymeric gelling agent," as used herein, shall mean polymers meeting this parameter. Preferably the hydrogel forming polymeric gelling agent does not have a Tg below about 180° C., and more preferably does not have a Tg prior to decomposition of the polymer, at temperatures of about 300° C. or higher. The Tg can be determined by differential scanning calorimetry (DSC) conducted at a heating rate of 20.0 C°/minute with 5 mg or smaller samples. The Tg is calculated as the midpoint between the onset and endset of heat flow change corresponding to the glass transition on the DSC heat capacity heating curve. The use of DSC to determine Tg is well known in the art, and is described by B. Cassel and M. P. DiVito in "Use of DSC To Obtain Accurate Thermodynamic and Kinetic Data", American Laboratory, January 1994, pp 14–19, and by B. Wunderlich in *Thermal Analysis*, Academic Press, Inc., 1990.

The hydrogel forming polymeric material is characterized as highly absorbent and able to retain water in its absorbed or "gel" state. Preferred hydrogel forming polymeric gelling agent hereof will be able to absorb at least about 40 g water (deionized) per gram of gelling agent, preferably at least about 60 g/g, more preferably at least about 80 g/g. These values, referred to as "Absorptive Capacity" herein can be determined according to the procedure in the Absorptive Capacity "Tea Bag" test described above.

The hydrogel forming polymeric gelling agent hereof will, in general, be at least partially crosslinked. Suitable cross-linking agents are well know in the art and include, for example, (1) compounds having at least two polymerizable double bonds; (2) compounds having at least one polymerizable double bond and at least one functional group reactive with the acid-containing monomer material; (3) compounds having at least two functional groups reactive with the acid-containing monomer material; and (4) polyvalent metal compounds which can form ionic cross-linkages.

Cross-linking agents having at least two polymerizable double bonds include (i) di- or polyvinyl compounds such as divinylbenzene and divinyltoluene; (ii) di- or poly-esters of unsaturated mono- or poly-carboxylic acids with polyols including, for example, di- or triacrylic acid esters of polyols such as ethylene glycol, trimethylol propane, glycerine, or polyoxyethylene glycols; (iii) bisacrylamides such as N,N-methylenebisacrylamide; (iv) carbamyl esters that can be obtained by reacting polyisocyanates with hydroxyl group-containing monomers; (v) di- or poly-allyl ethers of polyols; (vi) di- or poly-allyl esters of polycarboxylic acids such as diallyl phthalate, diallyl adipate, and the like; (vii) esters of unsaturated mono- or poly-carboxylic acids with mono-allyl esters of polyols such as acrylic acid ester of polyethylene glycol monoallyl ether; and (viii) di- or tri-allyl amine.

Cross-linking agents having at least one polymerizable double bond and at least one functional group reactive with the acid-containing monomer material include N-methylol acrylamide, glycidyl acrylate, and the like. Suitable cross-linking agents having at least two functional groups reactive with the acid-containing monomer material include glyoxal; polyols such as ethylene glycol and glycerol; polyamines such as alkylene diamines (e.g., ethylene diamine), poly-alkylene polyamines, polyepoxides, di- or polyglycidyl ethers and the like. Suitable polyvalent metal cross-linking agents which can form ionic cross-linkages include oxides, hydroxides and weak acid salts (e.g., carbonate, acetate and the like) of alkaline earth metals (e.g., calcium, magnesium) and zinc, including, for example, calcium oxide and zinc diacetate.

Cross-linking agents of many of the foregoing types are described in greater detail in Masuda et al., U.S. Pat. No. 4,076,663, issued Feb. 28, 1978, and Allen et al., U.S. Pat. No. 4,861,539, issued Aug. 29, 1989. Preferred cross-linking agents include the di- or polyesters of unsaturated mono- or polycarboxylic acids mono-allyl esters of polyols, the bisacrylamides, and the di- or tri-allyl amines. Specific examples of especially preferred cross-linking agents include N,N'-methylenebisacrylamide and trimethylol propane triacrylate.

The cross-linking agent will generally constitute from about 0.001 mole percent to 5 mole percent of the resulting hydrogel-forming polymeric material. More generally, the cross-linking agent will constitute from about 0.01 mole percent to 3 mole percent of the hydrogel-forming polymeric gelling agent used herein.

The hydrogel forming polymeric gelling agents hereof may be employed in their partially neutralized form. For purposes of this invention, such materials are considered partially neutralized when at least 25 mole percent, and preferably at least 50 mole percent of monomers used to form the polymer are acid group-containing monomers which have been neutralized with a base. Suitable neutralizing bases cations include hydroxides of alkali and alkaline earth metal (e.g. KOH, NaOH), ammonium, substituted ammonium, and amines such as amino alcohols (e.g., 2-amino-2-methyl-1,3-propanediol, diethanolamine, and 2-amino-2-methyl-1-propanol. This percentage of the total monomers utilized which are neutralized acid group-containing monomers is referred to herein as the "degree of neutralization." The degree of neutralization will preferably not exceed 98%.

Hydrogel forming polymeric gelling agents suitable for use herein are well known in the art, and are described, for example, in U.S. Pat. No. 4,076,663, Masuda et al., issued Feb. 28, 1978; U.S. Pat. No. 4,062,817, Westerman, issued Dec. 13, 1977; U.S. Pat. No. 4,286,082, Tsubakimoto et al., issued Aug. 25, 1981; U.S. Pat. No. 5,061,259, Goldman et al., issued Oct. 29, 1991, and U.S. Pat. No. 4,654,039, Brandt et al., issued Mar. 31, 1987.

Hydrogel forming polymeric gelling agents suitable for use herein are also described in U.S. Pat. No. 4,731,067, Le-Khac, issued Mar. 15, 1988, U.S. Pat. No. 4,743,244, Le-Khac, issued May 10, 1988, U.S. Pat. No. 4,813,945, Le-Khac, issued Mar. 21, 1989, U.S. Pat. No. 4,880,868, Le-Khac, issued Nov. 14, 1989, U.S. Pat. No. 4,892,533, Le-Khac, issued Jan. 9, 1990, U.S. Pat. No. 5,026,784, Le-Khac, issued Jun. 25, 1991, U.S. Pat. No. 5,079,306, Le-Khac, issued Jan. 7, 1992, U.S. Pat. No. 5,151,465, Le-Khac, issued Sep. 29, 1992, U.S. Pat. No. 4,861,539, Allen, Farrer, and Flesher, issued Aug. 29, 1989, and U.S. Pat. No. 4,962,172, Allen, Farrer, and Flesher, issued Oct. 9, 1990.

Suitable hydrogel forming polymeric gelling agents in the form of particles are commercially available from Hoechst Celanese Corporation, Portsmouth, Va., USA (Sanwet™ Superabsorbent Polymers) Nippon Shokubai, Japan (Aqualic™, e.g., L-75, L-76) and Dow Chemical Company, Midland, Mich., USA (Dry Tech™).

Hydrogel forming polymeric gelling agents in the form of fibers are commercially available from Camelot Technologies Inc., Leominster, Mass., USA (Fibersorb™, e.g., SA 7200H, SA 7200M, SA 7000L, SA 7000, and SA 7300).

The articles of the present invention may also contain other hydrophilic gelling agents. These include carboxylic acid-containing polymers as otherwise described above, except which have relatively lower degrees of crosslinking, such that they exhibit a Tg below 140° C., as well as a variety of other water soluble or colloidally water soluble polymers, such as cellulose ethers (e.g. hydroxyethyl cellulose, methyl cellulose, hydroxy propylmethyl cellulose), polyvinylpyrrolidone, polyvinylalcohol, guar gum, hydroxypropyl guar gum and xanthan gum. Preferred among these additional hydrophilic gelling agents are the acid-containing polymers, particularly carboxylic acid-containing polymers. Especially preferred are those that comprise water-soluble polymer of acrylic acid crosslinked with a polyalkenyl polyether of a polyhydric alcohol, and optionally an acrylate ester or a polyfunctional vinylidene monomer.

Preferred copolymers useful in the present invention are polymers of a monomeric mixture containing 95 to 99 weight percent of an olefinically unsaturated carboxylic monomer selected from the group consisting of acrylic, methacrylic and ethacrylic acids; about 1 to about 3.5 weight percent of an acrylate ester of the formula:

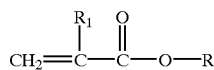

wherein R is an alkyl radical containing 10 to 30 carbon atoms and $R_1$ is hydrogen, methyl or ethyl; and 0.1 to 0.6 weight percent of a polymerizable cross-linking polyalkenyl polyether of a polyhydric alcohol containing more than one alkenyl ether group per molecule wherein the parent polyhydric alcohol contains at least 3 carbon atoms and at least 3 hydroxyl groups.

Preferably, these polymers contain from about 96 to about 97.9 weight percent of acrylic acid and from about 2.5 to about 3.5 weight percent of acrylic esters wherein the alkyl group contains 12 to 22 carbon atoms, and $R_1$ is methyl, most preferably the acrylate ester is stearyl methacrylate. Preferably, the amount of crosslinking polyalkenyl polyether monomer is from about 0.2 to 0.4 weight percent. The preferred crosslinking polyalkenyl polyether monomers are allyl pentaerythritol, trimethylolpropane diallylether or allyl sucrose. These polymers are fully described in U.S. Pat. No. 4,509,949, to Huang et al., issued Apr. 5, 1985.

Other preferred copolymers useful in the present invention are the polymers which contain at least two monomeric ingredients, one being a monomeric olefinically-unsaturated carboxylic acid, and the other being a polyalkenyl, polyether of a polyhydric alcohol. Additional monomeric materials may be present in the monomeric mixture if desired, even in predominant proportion.

The first monomeric ingredient useful in the production of these carboxylic polymers are the olefinically-unsaturated carboxylic acids containing at least one activated carbon-to-carbon olefinic double bond, and at least one carboxyl group. The preferred carboxylic monomers are the acrylic acids having the general structure

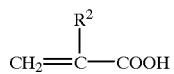

wherein $R^2$ is a substituent selected from the class consisting of hydrogen, halogen, and the cyanogen (—C≡N) groups, monovalent alkyl radicals, monovalent alkaryl radicals and monovalent cycloaliphatic radicals. Of this class, acrylic, methacrylic, and ethacrylic acid are most preferred. Another useful carboxylic monomer is maleic anhydride or the acid. The amount of acid used will be from about 95.5 to about 98.9 weight percent.

The second monomeric ingredient useful in the production of these carboxylic polymers are the polyalkenyl polyethers having more than one alkenyl ether grouping per molecule, such as alkenyl groups in which an olefinic double bond is present attached to a terminal methylene grouping, $CH_2=C<$.

The additional monomeric materials which may be present in the polymers include polyfunctional vinylidene monomers containing at least two terminal $CH_2<$ groups, including for example, butadiene, isoprene, divinyl benzene, divinyl naphthlene, allyl acrylates, and the like. These polymers are fully described in U.S. Pat. No. 2,798,053, to Brown, issued Jul. 2, 1957.

Examples of carboxylic acid copolymers useful in the present invention include Carbomer 934®, Carbomer 941®, Carbomer 950®, Carbomer 951®, Carbomer 954®, Carbomer 980®, Carbomer 981®, Carbomer 1342®, acrylates/C10–30 alkyl acrylate cross polymer (available as Carbopol 934®, Carbopol 941®, Carbopol 950®, Carbopol 951®, Carbopol 954®, Carbopol 980®, Carbopol 981®, Carbopol 1342®, and the Pemulen® series, respectively, from B. F. Goodrich).

Other carboxylic acid copolymers useful in the present invention include sodium salts of acrylic acid/acrylamide copolymers sold by the Hoechst Celanese Corporation under the trademark of Hostaceren PN73®. Also included are the hydrogel polymers sold by Lipo Chemicals Inc. under the trademark of HYPAN® hydrogels. These hydrogels consist of crystalline plicks of nitrates on a C—C backbone with various other pendant groups such as carboxyls, amides, and amidines. An example would include HYPAN SA 100 H®, a polymer powder available from Lipo Chemical.

Neutralizing agents for use in neutralizing the acidic groups of these polymers include those previously described.

Cationic Surfactants

Cationic surfactants are typically categorized as non-lathering surfactants but may be used in the articles of the present invention provided they do not negatively impact the desired benefits of the articles.

Nonlimiting examples of cationic surfactants useful herein are disclosed in McCutcheon's, *Detergents and Emulsifiers*, North American edition (1986), published by allured Publishing Corporation; and McCutcheon's, *Functional Materials*, North American Edition (1992).

Nonlimiting examples of cationic surfactants useful herein include cationic alkyl ammonium salts such as those having the formula:

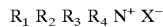

wherein $R_1$, is selected from an alkyl group having from about 12 to about 18 carbon atoms, or aromatic, aryl or alkaryl groups having from about 12 to about 18 carbon atoms; $R_2$, $R_3$, and $R_4$ are independently selected from hydrogen, an alkyl group having from about 1 to about 18 carbon atoms, or aromatic, aryl or alkaryl groups having from about 12 to about 18 carbon atoms; and X is an anion selected from chloride, bromide, iodide, acetate, phosphate, nitrate, sulfate, methyl sulfate, ethyl sulfate, tosylate, lactate, citrate, glycolate, and mixtures thereof. Additionally, the alkyl groups can also contain ether linkages, or hydroxy or amino group substituents (e.g., the alkyl groups can contain polyethylene glycol and polypropylene glycol moieties).

More preferably, $R_1$ is an alkyl group having from about 12 to about 18 carbon atoms; $R_2$ is selected from H or an alkyl group having from about 1 to about 18 carbon atoms; $R_3$ and $R_4$ are independently selected from H or an alkyl group having from about 1 to about 3 carbon atoms; and X is as described in the previous paragraph.

Most preferably, $R_1$ is an alkyl group having from about 12 to about 18 carbon atoms; $R_2$, $R_3$, and $R_4$ are selected from H or an alkyl group having from about 1 to about 3 carbon atoms; and X is as described previously.

Alternatively, other useful cationic surfactants include amino-amides, wherein in the above structure $R_1$ is alternatively $R_5CO-(CH_2)_n-$, wherein $R_5$ is an alkyl group having from about 12 to about 22 carbon atoms, and n is an integer from about 2 to about 6, more preferably from about 2 to about 4, and most preferably from about 2 to about 3. Nonlimiting examples of these cationic emulsifiers include stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Nonlimiting examples of quaternary ammonium salt cationic surfactants include those selected from the group consisting of cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl dimethyl ammonium chloride, distearyl methyl ammonium bromide, and mixtures thereof. Additional quaternary ammonium salts include those wherein the C12 to C22 alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the C16 to C18 range. The term "coconut" refers to an alkyl group derived from a coconut fatty acid, which generally have mixtures of alkyl chains in the C12 to C14 range. Examples of quaternary ammonium salts derived from these tallow and coconut sources include ditallow dimethyl ammonium chloride, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-dimonium chloride phosphate, stearamidopropyl ethyidimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Preferred cationic surfactants useful herein include those selected from the group consisting of dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, and mixtures thereof.

Chelators

The articles of the present invention may also comprise a safe and effective amount of a chelator or chelating agent. As used herein, "chelator" or "chelating agent" means an active agent capable of removing a metal ion from a system by forming a complex so that the metal ion cannot readily participate in or catalyze chemical reactions. The inclusion of a chelating agent is especially useful for providing protection against UV radiation that can contribute to excessive scaling or skin texture changes and against other environmental agents, which can cause skin damage.

A safe and effective amount of a chelating agent may be added to the compositions of the subject invention, preferably from about 0.1% to about 10%, more preferably from about 1% to about 5%, of the composition. Exemplary chelators that are useful herein are disclosed in U.S. Pat. No. 5,487,884, issued Jan. 30, 1996 to Bissett et al.; U.S. Pat. No. 5,462,963, issued Oct. 31, 1995 to Bush et al., U.S. Pat. No. 5,364,617, issued Nov. 15, 1994 to Bush et al. Preferred chelators useful in compositions of the subject invention are furildioxime and derivatives thereof.

Flavonoids

The articles of the present invention may optionally comprise a flavonoid compound. Flavonoids are broadly disclosed in U.S. Pat. Nos. 5,686,082 and 5,686,367, both of which are herein incorporated by reference. Flavonoids suitable for use in the present invention are flavanones selected from the group consisting of unsubstituted flavanones, mono-substituted flavanones, and mixtures thereof; chalcones selected from the group consisting of unsubstituted chalcones, mono-substituted chalcones, di-substituted chalcones, tri-substituted chalcones, and mixtures thereof; flavones selected from the group consisting of unsubstituted flavones, mono-substituted flavones, di-substituted flavones, and mixtures thereof; one or more isoflavones; coumarins selected from the group consisting of unsubstituted coumarins, mono-substituted coumarins, di-substituted coumarins, and mixtures thereof; chromones selected from the group consisting of unsubstituted chromones, mono-substituted chromones, di-substituted chromones, and mixtures thereof; one or more dicoumarols; one or more chromanones; one or more chromanols; isomers (e.g., cis/trans isomers) thereof; and mixtures thereof. By the term "substituted" as used herein means flavonoids wherein one or more hydrogen atom of the flavonoid has been independently replaced with hydroxyl, C1–C8 alkyl, C1–C4 alkoxyl, O-glycoside, and the like or a mixture of these substituents.

Examples of suitable flavonoids include, but are not limited to, unsubstituted flavanone, mono-hydroxy flavanones (e.g., 2'-hydroxy flavanone, 6-hydroxy flavanone, 7-hydroxy flavanone, etc.), mono-alkoxy flavanones (e.g., 5-methoxy flavanone, 6-methoxy flavanone, 7-methoxy flavanone, 4'-methoxy flavanone, etc.), unsubstituted chalcone (especially unsubstituted trans-chalcone), monohydroxy chalcones (e.g., 2'-hydroxy chalcone, 4'-hydroxy chalcone, etc.), di-hydroxy chalcones (e.g., 2',4-dihydroxy chalcone, 2',4'-dihydroxy chalcone, 2,2'-dihydroxy chalcone, 2',3-dihydroxy chalcone, 2',5'-dihydroxy chalcone, etc.), and tri-hydroxy chalcones (e.g., 2',3',4'-trihydroxy chalcone, 4,2',4'-trihydroxy chalcone, 2,2',4'-trihydroxy chalcone, etc.), unsubstituted flavone, 7,2'-dihydroxy flavone, 3',4'-dihydroxy naphthoflavone, 4'-hydroxy flavone, 5,6-benzoflavone, and 7,8-benzoflavone, unsubstituted isoflavone, daidzein (7,4'-dihydroxy isoflavone), 5,7-dihydroxy-4'-methoxy isoflavone, soy isoflavones (a mixture extracted from soy), unsubstituted coumarin, 4-hydroxy coumarin, 7-hydroxy coumarin, 6-hydroxy-4-methyl coumarin, unsubstituted chromone, 3-formyl chromone, 3-formyl-6-isopropyl chromone, unsubstituted dicoumarol, unsubstituted chromanone, unsubstituted chromanol, and mixtures thereof.

Preferred for use herein are unsubstituted flavanone, methoxy flavanones, unsubstituted chalcone, 2',4-dihydroxy chalcone, and mixtures thereof. Most preferred are unsubstituted flavanone, unsubstituted chalcone (especially the trans isomer), and mixtures thereof.

They can be synthetic materials or obtained as extracts from natural sources (e.g., plants). The naturally sourced material can also further be derivatized (e.g., a glycoside, an ester or an ether derivative prepared following extraction from a natural source). Flavonoid compounds useful herein are commercially available from a number of sources, e.g., Indofine Chemical Company, Inc. (Somerville, N.J.), Steraloids, Inc. (Wilton, N.H.), and Aldrich Chemical Company, Inc. (Milwaukee, Wis.).

Mixtures of the above flavonoid compounds may also be used.

The herein described flavonoid compounds are preferably present in the instant invention at concentrations of from about 0.01% to about 20%, more preferably from about 0.1% to about 10%, and most preferably from about 0.5% to about 5%.

Sterols

The articles of the present invention may comprise a safe and effective amount of one or more sterol compounds. Examples of useful sterol compounds include sitosterol, stigmasterol, campesterol, brassicasterol, lanosterol, 7-dehydrocholesterol, and mixtures thereof. These can be synthetic in origin or from natural sources, e.g., blends extracted from plant sources (e.g., phytosterols).

Anti-Cellulite Agents

The articles of the present invention may also comprise a safe and effective amount of an anti-cellulite agent. Suitable agents may include, but are not limited to, xanthine compounds (e.g., caffeine, theophylline, theobromine, and aminophylline).

Skin Lightening Agents

The articles of the present invention may comprise a skin lightening agent. When used, the compositions preferably comprise from about 0.1% to about 10%, more preferably from about 0.2% to about 5%, also preferably from about 0.5% to about 2%, by weight of the composition, of a skin lightening agent. Suitable skin lightening agents include those known in the art, including kojic acid, arbutin, ascorbic acid and derivatives thereof, e.g., magnesium ascorbyl phosphate or sodium ascorbyl phosphate or other salts of ascorbyl phosphate. Skin lightening agents suitable for use herein also include those described in U.S. Ser. No. 08/479,935, filed on Jun. 7, 1995 in the name of Hillebrand, corresponding to PCT Application No. U.S. 95/07432, filed Jun. 12, 1995; and U.S. Pat. No. 6,068,836, issued May 30, 2000 to Kvalnes et al.

Binders

The articles of the present invention may optionally comprise binders. Binders or binding materials are useful for sealing the various layers of the present articles to one another thereby maintaining the integrity of the article. The binders may be in a variety of forms including, but not limited to, spray on, webs, separate layers, binding fibers, etc. Suitable binders may comprise latexes, polyamides, polyesters, polyolefins and combinations thereof.

Additional Layers

In another embodiment, the article of the present invention may comprise one or more additional layers which one having ordinary skill in the art would recognize as separate and distinct from the creped nonwoven layer yet which are attached to creped nonwoven layer at some point. The additional layers are suitable for enhancing the overall grippability of the side of the article closest to the hand or other means for exerting mechanical action on the surface to be cleansed and/or therapeutically treated. Also, the additional layers are suitable for enhancing the soft feel of the side of the article which contacts the area to be cleansed and/or therapeutically treated. In any instance, these additional layers may also be referred to as consecutively numbered layers in addition to the two essential layers of the articles of the present invention, e.g., third layer, fourth layer, etc.

Suitable additional layers may be macroscopically expanded. As used herein, "macroscopically expanded, refers to webs, ribbons, and films which have been caused to conform to the surface of a three-dimensional forming structure so that both surfaces thereof exhibit a three-dimensional forming pattern of surface aberrations corresponding to the macroscopic cross-section of the forming structure, wherein the surface aberrations comprising the pattern are individually discernible to the normal naked eye (i.e., normal naked eye having 20/20 vision) when the perpendicular distance between the viewer's eye and the plane of the web is about 12 inches.

As used herein, "embossed" it is meant that the forming structure of the material exhibits a pattern comprised primarily of male projections. On the other hand, "debossed" refers to when the forming structure of the material exhibits a pattern comprised primarily of female capillary networks.

Preferred macroscopically expanded films comprise formed films that are structural elastic-like films. These films are described in U.S. Pat. No. 5,554,145, issued Sep. 10, 1996, to Roe et al..

Materials suitable for use in the additional layer having a thickness of at least one millimeter include, but are not limited to, those web materials disclosed in U.S. Pat. No. 5,518,801, issued to Chappell et al. on May 21, 1996.

METHODS OF MANUFACTURE

The personal care articles of the present invention are manufactured by adding the "hotmelt" cleansing component and optionally, the therapeutic benefit component, to the appropriate sheet of the creped nonwoven layer via a conventional method which may include, but is not limited to, sprinkling, simple extrusion, dip coating, spraying, slot coating, roll transfer (e.g., pressure roll or kiss roll), gravure printing, and a dipping & nipping application.

When more than on substrate layer is employed for the articles of the present invention then a sheet of the second layer is then placed on the sheet of the first layer, preferably, but not always, over the cleansing component and/or therapeutic benefit component. The sheets are sealed together by a conventional sealing method that may include, but is not limited to, heat, pressure, glue, ultrasound, etc. Heat sealing devices vary in design, and where a seal may not be able to be effected an interposing layer of a low-melting heat-sealable fibrous web such as the polyamide fibrous web known as Wonder Under (manufactured by Pellon, available from H. Levinson & Co., Chicago, Ill.) may be used between layers for this and other examples without changing the effect or utility of the articles. The sealed sheets are then partitioned into units for the consumer's use. Optional manufacturing steps may include calendaring to flatten the article, drying, creping, shrinking, stretching, or otherwise mechanically deforming.

METHODS OF CLEANSING AND DELIVERING A THERAPEUTIC OR AESTHETIC BENEFIT AGENT TO THE SKIN OR HAIR

The present invention also relates to a method of cleansing the skin or hair with a personal care article of the present invention. These methods comprise the steps of: a) wetting with water substantially dry, disposable personal care comprising: a water insoluble substrate; and a cleansing component disposed adjacent to said creped nonwoven layer, wherein said component comprises from about 10% to about 1000%, by weight of the water insoluble substrate, of a lathering surfactant and wherein the cleansing component exhibits a log $[(\eta\ @\ 25°\ C.)/(\eta\ @\ 200°\ C.)]$ greater than about 0.45 and/or a complex viscosity measured under an oscillation stress of 1 Pa of greater than 100 Pa·s at 25° C.; and b) contacting the skin or hair with the wetted article. In additional embodiments, such methods may also comprise the use of creped nonwoven layers having more the preferred Crepe Ratios, log viscosity ratio values, and complex viscosities at 25° C. as described herein.

The articles of the present invention are water-activated and are therefore intended to be wetted with water prior to use. As used herein, "water-activated" means that the present invention is presented to the consumer in dry form to be used after wetting with water. It is found that when the articles of the present invention include a lathering surfactant they produce lather or are "activated" upon contact with water and further agitation. Accordingly, the article is wetted by immersion in water or by placing it under a stream of water. When the articles of the present invention comprise a lathering surfactant in the cleansing component, lather may be generated from the article by mechanically agitating and/or deforming the article either prior to or during contact of the article with the skin or hair. The resulting lather is useful for cleansing the skin or hair. During the cleansing process and subsequent rinsing with water, any therapeutic or aesthetic benefit agents are deposited onto the skin or hair. Deposition of the therapeutic or aesthetic benefit agents are enhanced by the physical contact of the substrate with the skin or hair as well by the inclusion of one or more deposition aids.

EXAMPLES

The following examples further describe and demonstrate embodiments within the scope of the present invention. In the following examples, all ingredients are listed at an active level. The examples are given solely for the purpose of illustration and are not to be construed as limitations of the present invention, as many variations thereof are possible without departing from the spirit and scope of the invention. Where not specifically mentioned, the ingredients are mixed in a manner consistent with that method of mixing practiced by one skilled in the art.

Ingredients are identified by chemical or CTFA name.

I. Cleansing Components

Example 1

Shave a 53.0 gms of a bar soap which includes the following components:

| Ingredient | Wt % |
|---|---|
| Sodium Cocyl Isethionate | 27.77 |
| Paraffin | 16.72 |
| Sodium Alkyl Glycerol Sulfonate (AGS) | 14.90 |
| Soaps | 11.41 |
| Glycerine | 8.57 |
| Water | 5.50 |
| Stearic Acid | 5.74 |
| Sodium Isethionate | 3.04 |
| NaCl | 1.41 |
| EDTA | 0.10 |
| Etidronic Acid | 0.10 |
| Polyox | 0.03 |
| Perfume | 0.70 |
| Miscellaneous (including pigments) | 4.01 |
| Total | 100 |

Mix the bar soap shavings with 37.0 gms glycerin (99.7%), 9.5 gms water, and 0.5 gms perfume. Heat mixture to 200° F. while stirring continuously. Cold-mill mixture on a standard 3-roll mill and store cleansing component in a suitable sealed container.

Example 2

Shave 40.0 gms of a bar soap which includes the following components:

| Ingredient | Wt % |
|---|---|
| Sodium Soap | 52.40 |
| Sodium Alkyl Glycerol Sulfonate (AGS) | 16.50 |
| Magnesium Soap | 13.40 |
| Glycerine | 0.19 |
| Water | 5.50 |
| Stearic Acid | 1.60 |
| Sodium Isethionate | 3.00 |
| NaCl | 3.89 |
| EDTA | 0.10 |
| Etidronic Acid | 0.10 |
| Perfume | 0.70 |
| Miscellaneous (including pigments) | 2.62 |
| Total | 100 |

Mix the bar soap shavings with 45.0 gms glycerin (99.7%), 4.5 gms water, and 0.5 gms perfume. Heat mixture to 200° F. while stirring continuously. Cold-mill mixture on a standard 3-roll mill and store cleansing component in a suitable sealed container.

Example 3

Shave 40.0 gms of a bar soap which includes the following components:

| Ingredient | Wt % |
| --- | --- |
| Soap (Magnesium and Sodium) | 80.16 |
| Water | 11.50 |
| Stearic Acid | 5.70 |
| NaCl | 1.10 |
| EDTA | 0.25 |
| Perfume | 1.15 |
| Miscellaneous (including pigments) | 0.14 |
| Total | 100 |

Store the bar soap flakes in a suitable sealed container.

Example 4

Shave 40.0 gms of a bar soap which includes the following components:

| Ingredient | Wt % |
| --- | --- |
| Soap (Magnesium and Sodium) | 80.16 |
| Water | 11.50 |
| Stearic Acid | 5.70 |
| NaCl | 1.10 |
| EDTA | 0.25 |
| Perfume | 1.15 |
| Miscellaneous (including pigments) | 0.14 |
| Total | 100 |

Blend the bar soap flakes with sodium bicarbonate in a 90:10 weight ratio. Mill the mixture twice in a standard 3-roll mill. Collect the flakes and store in a suitable sealed container.

Example 5

| Ingredient | Wt % |
| --- | --- |
| Sodium Myristate* | 20.00 |
| Water | 28.07 |
| Coco amidopropyl betaine | 6.00 |
| Sodium Lauryl Sarcosinate | 8.00 |
| Stearyl Dimethyl Benzyl Ammonium Chloride (SDBAC) | 3.00 |
| Gycerine | 15.00 |
| Petrolatum | 15.00 |
| Perfume | 0.50 |
| Miscellaneous minors | 1.43 |
| Sodium Chloride | 3.00 |
| Total | 100 |

*Formed in-situ from Sodium Hydroxide + Myristic acid.

Melt Myristic acid at 65° C. Separately heat water, sodium hydroxide and sodium chloride at 80° C. When at temperature, add to Myristic acid to form sodium Myristate, mix gently until reacted. Add surfactants (Cocoamidopropyl Betaine and Sodium Lauryl Sarcosinate) and mix until dissolved. Add glycerine and SDBAC & mix for 10 minutes. Add petrolatum and mix at low speed to avoid shearing into small particle size. Allow to cool & set. Re-melt temperature is around 70° C.

Example 6

| Ingredient | Wt % | Wt % | Wt % |
| --- | --- | --- | --- |
| Water | 50.13 | 49.33 | 47.75 |
| Stearic acid | 3.25 | 3.20 | 3.10 |
| Palmitic acid | 2.70 | 2.66 | 2.58 |
| Myristic acid | 3.76 | 3.71 | 3.59 |
| Lauric acid | 1.52 | 1.49 | 1.45 |
| Glycerin | 14.77 | 16.49 | 15.98 |
| In situ Potassium soap | 16.74 | 14.55 | 14.10 |
| Pentasodium Pentate | 0.10 | 0.10 | 0.10 |
| Tetrasodium Etidrionate | 0.10 | 0.10 | 0.10 |
| Polyquaternium-10 | 0.49 | 0.49 | 0.49 |
| Sodium Lauroyl Sarcosinate | 3.94 | 3.88 | 3.76 |
| Petrolatum* | 1.50 | 3.00 | 6.00 |
| Perfume | 1.00 | 1.00 | 1.00 |
| Total | 100 | 100 | 100 |

*Suitable grades include Snow White Petrolatum USP and Super White Protopet from Witco Melt Stearic, Palmitic, Myristic, and Lauric Acids at 70° C. Separately heat Water, Polyquaternium-10, Preservatives, Potassium hydroxide at 80° C. At that temperature, add to Fatty Acids acid to form Potassium soap, mix gently until reacted. Add Sodium Lauroyl Sarcosinate and mix until dissolved. Add glycerine and mix for 10 minutes. Add Petrolatum and mix at low speed to avoid over-shearing into small particle size. Allow to cool & set. Re-melt temperature is around 70° C.

Example 7

| Ingredient | Wt % |
| --- | --- |
| PEG 6000 | 30–40% |
| PEG 8000 | 30–40% |
| Sodium Olefin Sulfonate | 13% |
| Sodium Lauroyl Sarcosinate | 3.5% |
| Coconut Imidazoline | 6% |
| Lauryl Dimethyl Betaine | 3% |
| Perfume | 1% |

Heat the Polyethylene glycols to 70° C., add Sarcosinate, Sulfonate, Imidazoline and Betaine and mix until homogeneous. Add the remaining ingredients except perfume and continue mixing. Cool to 60° C., add perfume, mix for 10 minutes and leave to set. Re-melting range is 40–50° C. for coating on articles.

Example 8

| Ingredient | Wt % |
| --- | --- |
| PEG 6000 | 30–40% |
| PEG 8000 | 30–40% |
| Lauryl ether sulfate* | 26% |
| Ethoxylated alcohol | 2.0% |
| Lauryl Dimethyl Betaine | 2.7% |
| Coconut Monoethanolamide (CMEA)† | 0–3% |
| Perfume | 1% |

*Na or Mg salt
†Can also be Coconut Diethanolamide

Heat the Polyethylene glycols to 70° C., add Lauryl Ether Sulfate, CMEA, and Ethoxylated Alcohol, and Betaine and mix. Add the remaining ingredients except perfume and continue mixing. Cool to 60° C. and add perfume, leave to set. Re-melting range is 40–50° C. for coating on articles.

Example 9

Heat 3 lbs of soap shavings of Example 2 with ¾ cup of isopropyl alcohol (99%) until the soap is melted. When the soap has melted, add the remaining alcohol. Add 10 oz. table sugar dissolved in as little water as possible. Blend about 4 tsp. of a dye into 8 oz. glycerin. Add the glycerin (99.7%). Stir. Continue to heat until consistency changes from a thin liquid to rope-like ribbons falling off the stirring implement and an aliquot of material hardens when dropped on a cold surface. Pour the mixture into a suitable container to harden. The mixture has the advantage of being remeltable upon heating that allows easy processing to prepare articles.

Examples 10–13

| Ingredient | Wt % | Wt % | Wt % | Wt % |
|---|---|---|---|---|
| Sodium Cocoyl Isethionate | 28 | 34 | 21 | — |
| Sodium Lauryl Sulfosuccinate | — | — | 28 | — |
| Sodium lauryl Sulfoacetate | — | — | — | 25 |
| Sodium Dodecyl Benzene Sulfonate | 5 | — | — | — |
| Filler ($^1$) | 53 | 38 | 15 | 40 |
| Hotmelt solvent/carrier ($^2$) | 9 | 10 | 25 | 10 |
| Perfume | 1 | 1 | 1 | 1 |
| Water ($^3$) | 4 | 17 | 10 | 24 |

($^1$) Non limiting examples of Fillers include: Dextrose, Dextrin, Colloidal Oatmeal, Corn Starch
($^2$) Non limiting examples of hotmelt solvents/carriers include Lauric acid, EGDS, Wax, Fatty alcohol, Paraffin, Sorbitol, PEG14M, Cellulose gum
($^3$) Can also be liquid polar solvent e.g. Glycerine, Propylene glycol, Low Molecular Weight PEG or mixtures thereof.

Melt hotmelt solvent/carrier with water or solvent at 60–70° C. in vessel & mix until homogeneous, add anionic surfactants whilst mixing. Add filler & mix further using high shear until equally dispersed, cool to 50° C. & add perfume, mix for an additional 10 minutes, allow to cool & set. Re-melt at 60–70° C. for coating onto articles.

Examples 14–15

| Ingredient | Wt % | Wt % |
|---|---|---|
| Sodium Laureth 3 sulfate | 10 | 10 |
| DEFI* | 17 | 30 |
| Cocoamidopropyl Betaine | 1 | 4.5 |
| PEG 4000 | 30–35 | 20–25 |
| PEG 100,000 | 3–5 | 3–4 |
| Stearic acid | 20 | 11 |
| Sodium Stearate | 4 | 3.5 |
| Perfume | 1 | 1 |
| Water | 9 | 11 |

*Directly Esterified Fatty acid Istehionate (available from Lever Bros.)

Heat PEG and water to 80° C. Add surfactants & mix until dissolved. Add Stearic acid and Sodium stearate. Mix until homogeneous, cool to 60° C. and add perfume, mix for 10 minutes. Allow to cool & set. Re melt-range for application is 60–80° C.

Example 16–18

| Ingredient | Wt % | Wt % | Wt % |
|---|---|---|---|
| Sodium Cocoyl Isethionate | 27.00 | 27.00 | 27.00 |
| Cocoamidopropyl Betaine | 4.36 | 4.36 | 4.36 |
| Sodium Isethionate | 2.10 | 2.10 | 2.10 |
| Sodium stearate | 8.00 | 6.00 | 6.00 |
| Stearic acid | 20.00 | 17.00 | 17.00 |
| PEG 8000 | 25.90 | — | 10.00 |
| PEG 4000 | — | — | 7.00 |
| PEG 3350 | — | 21.00 | — |
| PEG 1450 | 2.95 | 2.95 | 8.00 |
| PEG 300 | 2.05 | 2.05 | 2.00 |
| Maltodextrin | 10.00 | 10.00 | 10.00 |
| Perfume | 1.00 | 1.00 | 1.00 |
| NaCl | 0.88 | 0.88 | 0.88 |
| TiO2 | 0.70 | 0.70 | 0.70 |
| EDTA | 0.03 | 0.03 | 0.03 |
| EHDP | 0.03 | 0.03 | 0.03 |
| Water | 5.00 | 5.00 | 5.00 |

Heat PEGs and water to 60–70° C. Add Isethionates and Betaine and mix until dissolved. Add Stearic acid and Sodium stearate. Mix until homogeneous, cool to 60° C. and add perfume, mix for 10 minutes. Allow to cool and to set until required. Remelt range is 60–80° C.

Example 19

| Ingredient | Wt % |
|---|---|
| SEFA* Cottonate | 57.5 |
| Citric acid | 0.30 |
| Cocoamidopropyl betaine | 3.5 |
| Sodium lauroyl sarcosinate | 10.7 |
| Ethylene vinyl acetate polymer (Elvax 40W) | 8.0 |
| Polymethylsilsesquioxane powder (Tospearl 145A) | 20.0 |

*SEFA is an acronym for sucrose esters of fatty acids

Melt the ethylene vinyl acetate polymer into the SEFA cottonate at 90° C. and high shear mix. Add the surfactant powders and citric acid and mix. Add the Polymethylsilsesquioxane powder, mix, and cool to set. The composition is remeltable and easy impregnates into or coat onto substrates.

Example 20

| Ingredient | Wt % |
|---|---|
| Sodium laureth-10 carboxylate (Empicol CB5S*) | 50.0 |
| C12–14, 12EO Alcohol Ethoxylate (Empilan KB12*) | 50.0 |

*available from Albright & Wilson

Melt the alcohol ethoxylate, blend in the carboxylate until homogeneous, cool to solidify until ready for use. The composition is remeltable and easy impregnate into or coat onto substrates.

Example 21–28

| Ingredient | Wt % | Wt % | Wt % | Wt % | Wt % | Wt % | Wt % | Wt % |
|---|---|---|---|---|---|---|---|---|
| Sodium Laureth-3 sulfate | 27 | 14 | 27 | 14 | 27 | 14 | 27 | 14 |
| Aerosol OT† | 4 | 2 | — | — | — | — | — | — |
| DEFI* | — | — | — | — | 4 | 2 | — | — |
| Cocoamidopropyl Betaine | — | — | — | — | — | — | 4 | 2 |
| Tallow 20EO | — | — | 4 | 2 | — | — | — | — |
| PEG 4000 | 38 | 52 | 38 | 52 | 38 | 52 | 38 | 52 |
| Stearic acid | 19 | 26 | 19 | 26 | 19 | 26 | 19 | 26 |
| Perfume | 1 | 1 | 1 | 1 | 1 | 1 | 1 | 1 |
| Water | 11 | 5 | 11 | 5 | 11 | 5 | 11 | 5 |

†Dioctyl Sulfosuccinate
*Directly Esterified Fatty acid Istehionate (available from Lever Bros.)

Heat PEG4000, stearic acid and water to 70° C. Add Sodium Laureth-3 sulfate amd co-surfactants (Aerosol TO, Betaine, DEFI, or Tallow 20EO) and mix until dissolved. Cool to 60° C. and add perfume, mix for 10 minutes. Allow to cool & set until required. Remelt range is 60–80° C.

Example 29A

In this embodiment of the cleansing component an in situ reaction of an Butenedioic acid ester and Alkali metal Sulfite takes place to form an Alkyl sulfosuccinate. Additonally, mild co-surfactants are added to boost lathering.

| Ingredient | Wt % |
|---|---|
| HTFA (Hydrogenated Tallow Fatty acid/stearic acid) | 15% |
| Paraffin | 10% |
| C12–C14 Sodium alkene sulfonate* | 8% |
| Zinc stearate | 5% |
| Water | 10% |
| Lauryl maleate | 31.5% |
| Disodium sulfite (Na2SO3) | 13.5% |
| PEG 14,000 | 5% |
| Perfume | 1% |

*Other suitable surfactants may include Acyl Isethionates, Sulfates, Sulfonates, Sulfoacetates or mixtures thereof.

Melt HTFA and Paraffin at 75° C., Add Sodium Alkane Sulfonate and Zinc stearate and Water & mix until homogeneous. Add Lauryl Maleate, ensure it is fully dissolved, slowly add Disodium Sulfite over 30 minutes to react. Increase heat to 85° C. & mix under vacuum for 1 hour. When reaction is complete add PEG14,000, blend and cool to 60° C., quickly add perfume & leave to set. Re-melt range is 70–80° C.

Examples 29B–E

| Ingredient | Wt % | Wt % | Wt % | Wt % |
|---|---|---|---|---|
| Na Alkyl Glyceryl Ether Sulfonate | 29.00 | 29.00 | 29.00 | 29.00 |
| Na Cocoyl Isethionate | 20.0 | 30.0 | — | — |
| Coco Betaine | 10.0 | — | 10.0 | — |
| Na Lauroyl Sarcosinate | — | — | 20.0 | 30.0 |
| Alkyl Polyglucoside | 20.0 | 20.0 | 20.0 | 20.0 |
| Propylene Glycol | 19.8 | 19.8 | 19.8 | 19.8 |
| Fragrance | 1.0 | 1.0 | 1.0 | 1.0 |
| Citric acid | 0.2 | 0.2 | 0.2 | 0.2 |

Heat the propylene glycol to 90° C., add the co-surfactants (Isethionate, Betaine or Sarcosinate), mix until dissolved. Add the Sodium Alkyl Glyceryl Sulfonate & high shear mix until homogeneous. Add the Alkyl Polyglucoside, continue mixing until dissolved. Add the citric acid, drop the temperature to 50–60° C., add the perfume mix for 10 minutes, and allow to cool. Coating temperature is 40–50° C.

Example 30–32

| Ingredient | Wt % | Wt % | Wt % |
|---|---|---|---|
| 12-Hydroxy Stearic acid* | 14.5 | 18.8 | 14.6 |
| Na Lauroyl Isethionate | 34.5 | 32.3 | — |
| Na Cocoyl Isethionate | — | — | 34.8 |
| Na Alkyl Glyceryl Ether Sulfonate | — | 2.7 | 3.0 |
| Na Lauroyl Sarcosinate | 4.0 | 3.6 | 4.0 |
| Coco Betaine | 3.0 | 3.1 | — |
| Altowhite clay | 14.0 | 3.4 | 4.0 |
| Sodium Chloride | 0.6 | — | 0.1 |
| Fragrance | 0.6 | — | 0.5 |
| Miscellaneous Minors | 4.0 | 5.6 | 6.0 |
| Water | 34.8 | 30.5 | 33.0 |

Can also be: *Palmitic Acid, Stearic Acid, Behenic Acid, 12-Hydroxystearic Acid

Add Water, 12-Hydroxy Stearic acid, & sodium chloride (where applicable) and mix & heat to 70° C. Other ingredients are then added, Coco betaine, Na Lauroyl Sarcosinates, Na Alkyl Glyceryl Ether Sulfonates and/or, Isethionates mixed until dissolved. Kaolin clay & Miscellaneous minors are then added and sheared until homogeneous. Perfume is added last before cooling to room temperature. Re-melt at 60–70° C. for coating.

Example 33–36

| Ingredient | Wt % | Wt % | Wt % | Wt % |
|---|---|---|---|---|
| 12-Hydroxy Stearic acid | 14.0 | 4.0 | 10.0 | 9.0 |
| Myristic acid | — | 14.0 | — | 9.0 |
| Sodium Lauroyl Isethionate | — | — | 34.0 | — |
| Sodium Cocoyl Isethionate | 30.0 | 44.0 | — | 44.0 |
| Sodium Linear Alkyl Benzene Sulfonate | 2.0 | 2.5 | 0.65 | 2.5 |
| Sodium Lauroyl Sarcosinate | — | — | 4.0 | — |
| Coco Betaine | — | — | 8.0 | — |
| Propylene glycol | 14.0 | 5.0 | — | 5.0 |
| Paraffin wax | — | — | 9.0 | — |
| Sodium Chloride | 2.0 | 2.0 | 5.7 | 2.0 |
| Miscellaneous minors | 1.9 | 4.9 | 4.6 | 6.9 |
| Water | 36.1 | 23.6 | 24.05 | 21.6 |

Add Water, Propylene glycol, 12-Hydroxy Stearic acid (& Myristic acid where applicable), and sodium chloride; mix & heat to at 70° C. Other ingredients are then added, Coco betaine, Na Alkyl Glyceryl Ether Sulfonates and Na Lauroyl Sarcosinates or Isethionates & mixed until dissolved. Paraffin wax & miscellaneous minors are then added and mixed under low shear until well dispersed. Perfume is added last before cooling to room temperature. Re-melt at 60–70° C. for coating.

Example 37–39

| Ingredient | Wt % | Wt % | Wt % |
|---|---|---|---|
| Myristic Acid | 20.0 | — | — |
| Stearic Acid | — | 20.0 | — |
| Behenic Acid | — | — | 21.0 |
| Sodium Lauroyl Isethionate | 6.2 | — | 25.0 |
| Sodium Cocoyl Isethionate | 18.5 | 35.0 | — |
| Sodium Linear Alkyl Benzene Sulfonate | 0.5 | 0.7 | 0.6 |
| Sodium Lauroyl Sarcosinate | — | — | 3.0 |
| Sodium Paraffin Sulfonate | — | 3.0 | — |
| Sodium Lauryl Methyl Ester Sulfonate | — | 2.0 | — |
| CocoBetaine | — | — | 8.0 |
| Corn Starch | 10.0 | — | 4.0 |
| Dextrin | — | — | 4.0 |
| Altowhite clay | 3.6 | — | — |
| Paraffin wax | 8.1 | — | — |
| Sodium Isethionate | 3.1 | 3.4 | 1.3 |
| Sodium Chloride | 0.3 | 0.3 | 6.6 |
| DMDM Hydantoin | 0.2 | — | — |
| Miscellaneous minors | 4.0 | 5.1 | 2.1 |
| Water | 25.5 | 30.5 | 24.4 |

Add Water, Free fatty acids, Propylene Glycol, sodium chloride and mix & heat to 85° C. Other ingredients are then added, Coco betaine, Anionic surfactants (sulfonates and/or Sarcosinates, Isethionates), Kaolin clay; and Paraffin wax. Miscellaneous minors, & starches are then added & sheared until homogeneous. Perfume & DMDM Hydantoin (where applicable) is added last before cooling to room temperature. Re-melt at 70–80° C. for coating.

Example 40–43

| Ingredient | Wt % | Wt % | Wt % | Wt % |
|---|---|---|---|---|
| Myristic Acid | 35.0 | 35.0 | 35.0 | 35.0 |
| Sodium Cocoyl Isethionate | 25.0 | — | — | — |
| N-Methyl Glucose Amide | — | 25.0 | — | — |
| Sodium Laureth-3 Sulfate | — | — | 25.0 | — |
| Sodium Alkyl Ether Glyceryl Sulfonate | — | — | — | 25.0 |
| Propylene glycol | 5.0 | 5.0 | 5.0 | 5.0 |
| Miscellaneous minors | 1.6 | — | 1.1 | 2.4 |
| Water | 33.4 | 35.0 | 34.0 | 32.6 |

Add Water, Myristic acid, Propylene Glycol and mix & heat to at 80° C. Add surfactants (Na Ether Glyceryl Sulfonate or Na Laureth-3 Sulfate or Na Cocoyl Isethionate or N-Methyl Glucose Amide) and homogeneously mix. Add Perfume & miscellaneous minors (where applicable) last before cooling to room temperature. Re-melt at 70–80° C. for coating.

Example 44–47

| Ingredient | Wt % | Wt % | Wt % | Wt % |
|---|---|---|---|---|
| DEFI* | 27.8 | 27.0 | 27.0 | 27.8 |
| Cocoamidopropyl Betaine | 5.2 | 5.0 | 5.0 | 5.2 |
| PEG 8000 | 32.1 | 29.5 | 35.0 | 45.1 |
| PEG 4000 | 3.1 | — | — | — |
| Stearic/Palmitic acid | 11.6 | 8.6 | 9.0 | 11.6 |
| Maltodextrin | 10.3 | 10.0 | — | 4.4 |
| POE (23) Cetyl ether | 4.0 | 5.0 | 10.0 | — |
| POE (20) Cetyl ether | — | 5.0 | — | — |
| Perfume | — | 0.3 | 0.3 | — |
| Sodium stearate | — | — | 5.0 | — |
| TiO2 | — | — | 0.5 | — |
| EHDP | — | 0.1 | 0.1 | — |
| EDTA | — | 0.1 | 0.1 | — |
| Misc. Salts | — | 2.9 | 2.9 | — |
| Water | 5.9 | 6.5 | 5.1 | 5.9 |

*Directly Esterified Fatty acid Isethionate (Available from Lever Bros.)

Melt PEG's, Stearic/Palmitic acid+water in a vessel at 70° C. Add DEFI and (where applicable) Sodium Stearate, Betaine, POE Cetyl Ethers, Maltodextrin, preservatives, TiO2, Salts & continue mixing until homogeneous. Cool to 60° C., add perfume, allow to set. Remelts in the range 50–70° C.

Example 48–50

| Ingredient | Wt % | Wt % | Wt % |
|---|---|---|---|
| Sodium Lauroyl Sarcosinate | 15.0 | 0.0 | 27.0 |
| Sodium Laureth-3 Sulfate | 5.0 | 5.0 | 5.0 |
| Betaine | 5.0 | 20.0 | 0.0 |
| Stearic-Palmitic acid | 5.0 | 5.0 | 5.0 |
| PEG 8000 | 25.0 | 44.0 | 39.0 |
| PEG 6000 | 27.0 | 8.0 | 5.0 |
| POE (40) Cetyl Ether | 10.0 | 10.0 | 10.0 |
| Paraffin wax | 2.0 | 2.0 | 3.0 |
| Perfume | 1.0 | 1.0 | 1.0 |
| Water | 5.0 | 5.0 | 5.0 |

Melt PEG 6000+8000, Stearic Palmitic acid+water in a vessel at 70° C. Add Sarcosinate (where applicable), Betaine, POE (40) Cetyl Ether & continue mixing. Add paraffin wax and mix under low shear. Cool to 60° C., add perfume, and allow to set. Remelts in the range 50–70° C.

Examples 51–54

| Ingredient | Wt % | Wt % | Wt % | Wt % |
|---|---|---|---|---|
| PEG 8000 | 34.0 | 32.0 | 30.0 | 25.0 |
| Urea | 1.0 | 3.0 | 5.0 | 10.0 |
| Sodium Cocoyl Isethionate | 27.0 | 27.0 | 27.0 | 27.0 |
| Palmitic-Stearic acid | 12.0 | 12.0 | 12.0 | 12.0 |
| Cocoamidopropyl Betaine | 5.0 | 5.0 | 5.0 | 5.0 |
| Maltodextrin | 10.0 | 10.0 | 10.0 | 10.0 |
| *Na Stearate | 5.0 | 5.0 | 5.0 | 5.0 |
| EHDP | 0.02 | 0.02 | 0.02 | 0.02 |
| EDTA | 0.5 | 0.5 | 0.5 | 0.5 |
| Titanium Dioxide | 0.5 | 0.5 | 0.5 | 0.5 |
| Perfume | 0.25 | 0.25 | 0.25 | 0.25 |
| Misc. Salts | 1.96 | 1.96 | 1.96 | 1.96 |
| Water | 6.25 | 6.25 | 6.25 | 6.25 |

*(formed in-situ from Na OH + Stearic acid)

Melt PEG 8000+Stearic Palmitic acid in a vessel at 80° C., mix & add 50% NaOH solution to form Na Stearate.

Once reacted add Urea, Istehionate, Betaine, & misc. salts & continue mixing. Add maltodextrin and TiO$_2$ & preservatives and mix under high shear until homogeneous. Add all remaining ingredients except perfume & mix for 30 minutes. Add perfume & quickly cool to set. Re-melt range is 70–80° C.

Examples 55–60

| Ingredient | Wt % | Wt % | Wt % | Wt % | Wt % | Wt % |
|---|---|---|---|---|---|---|
| Linear Dodecyl Benzene Sulfonic Acid | 35.1 | 24.6 | 24.6 | 35.1 | 24.6 | 24.6 |
| Glutaric Acid | 35.1 | 10.0 | 15.0 | — | — | — |
| Oxalic Acid | — | 4.2 | 7.3 | 35.1 | — | — |
| Organic Acid* | — | — | — | — | 22.3 | 22.3 |
| Sodium carbonate** | 16.2 | 12.5 | 16.0 | 16.0 | 9.4 | 16.0 |
| Sodium sulfate | 10.8 | 47.7 | 36.1 | 10.8 | 42.7 | 36.1 |
| Sodium stearate | 1.8 | — | — | 1.4 | — | — |
| Perfume | 1.0 | 1.0 | 1.0 | 1.0 | 1.0 | 1.0 |

*Organic Acid can comprise Citric Acid, DBA, Succinic Acid, Tartaric Acid
**Can also be Sodium Bicarbonate, Sodium Hydroxide Made by reaction—in a non-aqueous environment—of linear alkyl aryl sulfonic acid with a solid particulate neutralising agent. Melt acid ingredients above 70° C., slowly add neutralising agent over 30 minutes, mix for 10–180 minutes. Perfume and other aesthetic agents may be added at the last stage of the mixing process before cooling.

Example 61

| Ingredient | Wt % |
|---|---|
| Water | 19.00% |
| Propylene glycol | 10.00% |
| Cocoamidopropyl Betaine (80%) | 20.00% |
| Alkyl Polyglucoside (50%) | 30.00% |
| Kettle soap (Sodium Tallowate/Palm Kernelate)* (75%) | 20.00% |
| Perfume | 1.00% |

*Conventional unmilled toilet Soap (e.g. 80% Tallow; 20% Palm Kernel Oil stock superfatted soap).
Alternative crystallising agents can be:
Semi or fully synthetic finished soaps as described in examples 1, 2, 3, 4
Cetyl/Stearyl/Behenyl alcohol or mixtures thereof
Palmitic/Stearic/Behenic/12-hydroxystearic Acid or mixtures thereof Heat all ingredients except perfume to 70–80° C. whilst stirring with overhead stirrer. Take care not to aerate batch. Stir until all crystalline material has dissolved and a clear homogenous mix is observed, cool to 50° C. & add perfume, mix for a further 10 minutes.

Example 62

| Ingredient | Wt % |
|---|---|
| Water | 19% |
| Propylene glycol | 10% |
| Cocoamidopropyl Betaine* (80%) | 5% |
| Sodium Laureth Sulfate (3EO)** (30%) | 45% |
| Kettle soap (Sodium Tallowate/Palm Kernelate)* (75%) | 20% |
| Perfume | 1% |

*or other Zwitterionic surfactant well known in the art
**or other alkali earth metal salts of anionic surfactant well know in the art Heat all ingredients except perfume to 70–80° C. whilst stirring with overhead stirrer. Take care not to aerate batch. Stir until all crystalline material has dissolved and a homogenous mix is observed, cool to 50° C. & add perfume, mix for a further 10 minutes.

Example 63

| Ingredient | Wt % |
|---|---|
| Water | 29.46% |
| Propylene glycol | 10.00% |
| Cocoamidopropyl Betaine (80%) | 18.75% |
| Sodium Lauroyl Sarcosinate (95%) | 15.79% |
| Cocamide MEA* (99%) | 5.00% |
| Kettle soap (Sodium Tallowate/Palm Kernelate)* (75%) | 20.00% |
| Perfume | 1.00% |

*Can be replaced by suitable non-ionic surfactant such as Cocamide DEA, Cocamide MIPA or mixtures thereof, Alkyl Polyglucoside, Ethoxylated alcohols Heat all ingredients except perfume to 70–80° C. whilst stirring with overhead stirrer. Take care not to aerate batch. Stir until all crystalline material has dissolved and a homogenous mix is observed, cool to 50° C. & add perfume, mix for a further 10 minutes.

Example 64

| Ingredient | Wt % |
|---|---|
| Water | 14% |
| Propylene glycol | 10% |
| Cocoamidopropyl Betaine (80%) | 5% |
| Sodium Laureth Sulfate (3EO) (30%) | 45% |
| Kettle soap (Sodium Tallowate/Palm Kernelate)* (75%) | 20% |
| Crystal sugar* | 5% |
| Perfume | 1% |

*It is well know in the art of hotmelt soaps bars that some chemicals can be used to control clarity, melt point and softness of soap by preventing crystals forming leading to an amourphous type of solid. Melt point, molten viscosity, hardness and aesthetics can thus be controlled. Examples include sugars and their families: Glucose (Dextrose), Fructose, Sucrose, Sorbitol.

Heat all ingredients except perfume to 70–80° C. whilst stirring with overhead stirrer. Take care not to aerate batch. Stir until all crystalline material has dissolved and a homogenous mix is observed, cool to 50° C. & add perfume, mix for a further 10 minutes.

Example 64A

In this embodiment petrolatum is used as a structurant to give room temperature viscosity.

| Ingredient | Wt % | Wt % | Wt % |
|---|---|---|---|
| Sodium Cocoyl Istehionate | — | 10 | 20.00 |
| Sodium Lauryl sulfate | 20.00 | 10 | — |
| Glycerine | 49.00 | 49.00 | 49.00 |
| Petrolatum | 30.00 | 30.00 | 30.00 |
| Perfume | 1.00 | 1.00 | 1.00 |

Heat glycerine to 80° C., add surfactants (Sodium Cocoyl Isethionate & Sodium Lauryl Sulfate) & mix until dissolved. Add Petrolatum slowly & stir. Cool to 60° C. and add perfume, stir until homogeneous and allow to cool.

Example 64B

In another embodiment, alternative lipids are used as hotmelt carriers.

| Ingredient | Wt % | Wt % | Wt % |
|---|---|---|---|
| Sodium Cocoyl Istehionate | 45.90 | 45.90 | 45.90 |
| Cocoamidopropyl Betaine | 17.00 | 17.00 | 17.00 |
| Glycerine | 5.00 | 5.00 | 5.00 |
| Titanium Dioxide | 1.00 | 1.00 | 1.00 |
| Petrolatum | 30.00 | — | — |
| Cocoa Butter | — | 30.00 | — |
| Coronet Lanolin | — | — | 30.00 |
| Citric acid anhydrous | 0.10 | 0.10 | 0.10 |
| Perfume | 1.00 | 1.00 | 1.00 |

Heat glycerine to 80° C., add surfactants (Sodium Cocoyl Isethionate & Sodium Lauryl Sulfate) & mix until dissolved. Add Lipid slowly & stir. Cool to 60° C. and add perfume, stir until homogeneous. Allow to cool

Example 65

| Ingredient | Wt % |
|---|---|
| Alkyl polyglucoside | 38.42 |
| Sodium Lauroyl Sarcosinate | 20.23 |
| Cocoamidopropyl Betaine | 24.03 |
| *Alcohol Ethoxylate | 15.00 |
| Perfume | 1.50 |
| Citric acid anhydrous | 0.30 |

Melt all ingredients except perfume at 70–80° C. & mix under shear until all powders are dissolved. Cool to 50° C. add perfume & mix for a further 10 minutes.

Example 66

| Ingredient | Wt % |
|---|---|
| Alcohol Ethoxylate | 21.53 |
| Sodium Lauroyl Sarcosinate | 25.00 |
| Cocoamidopropyl Betaine | 30.30 |
| MEA Laureth-3 sulfate | 21.05 |
| Perfume | 0.12 |
| Citric acid anhydrous | 2.00 |

Melt all ingredients except perfume at 70–80° C. & mix under shear until all powders are dissolved. Cool to 50° C. add perfume & mix for a further 10 minutes.

Example 67

| Ingredient | Wt % |
|---|---|
| MEA Laureth sulfate | 48.70 |
| Cocoamidopropyl Betaine | 40.00 |
| PEG 10,000* | 10.00 |
| Perfume | 1.00 |
| Citric acid anhydrous | 0.30 |

*Or other suitable molecular weights of PEG suitable from 1,000 upwards
Other suitable crystalline solvent are EO/PO copolymers.

Melt all ingredients except perfume at 70–80° C. & mix under shear until all powders are dissolved. Cool to 50° C. add perfume & mix for a further 10 minutes.

Example 68

| Ingredient | Wt % |
|---|---|
| Alcohol Ethoxylate | 48.70 |
| Sodium Lauroyl Sarcosinate* | 25.00 |
| Propylene glycol** | 25.00 |
| Perfume | 1.00 |
| Citric acid anhydrous | 0.30 |

*can be replaced by other suitable anionic anhydrous surfactants, for examples Acyl glutamate (Amisoft CS11, LS11), Sodium Laureth sulfate (Empicol ESB70), Sodium Cocoyl Isethionate (Hostapon SCI)
**can be replaced with other suitable polar solvents such as low Mw PEG (200, 400 etc), Glycerine, Melt all ingredients except perfume at 70–80° C. & mix under shear until all powders are dissolved. Cool to 50° C. add perfume & mix for a further 10 minutes.

Example 69

| Ingredient | Wt % |
|---|---|
| PEG 1500 | 30.00 |
| Cocoamidopropyl Betaine | 6.25 |
| MEA Laureth-3 sulfate | 37.88 |
| Alcohol Ethoxylate | 20.00 |
| Perfume | 1.00 |
| Urea extra pure | 5.00 |

Melt all ingredients except perfume at 70–80° C. & mix under shear until all powders are dissolved. Cool to 50° C. add perfume & mix for a further 10 minutes. Because system is anhydrous, Urea does not break down into ammonia at high temp and/or low pH, it gives both skin benefits and helps homogeneity of mix.

Example 70

| Ingredient | Wt % |
|---|---|
| Mono Alkyl Phosphate (acid form) | 20.00 |
| Triethanol amine 99% | 13.75 |
| Cocoamidopropyl Betaine | 12.50 |
| MEA Laureth-3 sulfate | 15.15 |
| Alcohol Ethoxylate | 19.00 |

-continued

| Ingredient | Wt % |
|---|---|
| Glycerine | 13.60 |
| Perfume | 1.00 |

Melt Mono alkyl phosphate+Glycerine to 70° C., add TEA slowly whilst mixing, once neutralised add remaining ingredients except perfume. Mix until a homogeneous phase is obtained. Cool to 60° C. and add perfume, mix for 10 minutes & allow to cool. Re-melt at 70–80° C. for application.

Example 71

| Ingredient | Wt % |
|---|---|
| Alcohol Ethoxylate | 24.77 |
| Cocoamidopropyl Betaine | 31.25 |
| MEA Laureth-3 sulfate | 37.88 |
| Polyquaternium-10 | 2.00 |
| Titanium Dioxide | 1.00 |
| Perfume | 3.00 |
| Citric acid anhydrous | 0.10 |

Heat MEA AE3S With Alcohol Ethoxylate to 70° C., add Betaine, TiO2 and Polyquaternium-10 and mix under high shear until well dispersed (high shear can be achieved by means of a conventional rotor/stator mixer or using ultrasonic energy to disperse powders). Cool to 60° C., add Citric acid & perfume. Mix for a further 10 minutes. Allow to set. Re-melt range is 50–60° C.

Example 72

| Ingredient | Wt % |
|---|---|
| Water | 6.53 |
| Sodium Laureth 3 Sulfate | 52.45 |
| Fumed silica | 5.00 |
| Cocoamidopropyl Betaine | 34.64 |
| Kathon CG* | 0.03 |
| Disodium EDTA | 0.10 |
| Sodium Benzoate | 0.25 |
| Perfume | 1.00 |

*Methilchloroisothiazolinone (and) Methylisothiazolinone

In a vessel, add the water (or propylene glycol), anionic surfactants and nonioinic surfactants (a vacuum vessel is preferred to avoid aeration, heat to 60° C. Mix until homogeneous, add all other ingredients except binder (Fumed Silica) and mix until dissolved. Add Binder and mix until well dispersed, sudden thickening of the batch occurs at this stage and powerful mixing is desired. Allow to cool and set. Re-melt is preffered at above 60° C.

Example 73

| Ingredient | Wt % |
|---|---|
| Water | 6.53 |
| Sodium Laureth 3 Sulfate | 52.45 |
| Bentonite clay | 5.00 |
| Cocoamidopropyl Betaine | 34.64 |
| Kathon CG* | 0.03 |
| Disodium EDTA | 0.10 |
| Sodium Benzoate | 0.25 |
| Perfume | 1.00 |

*Methilchloroisothiazolinone (and) Methylisothiazolinone

In a vessel add the water (or propylene glycol), anionic surfactants and nonioinic surfactants (a vacuum vessel is preferred to avoid aeration, heat to 60° C. Mix until homogeneous, add all other ingredients except binder (Bentonite clay) and mix until dissolved. Add Binder and mix until well dispersed, sudden thickening of the batch occurs at this stage and powerful mixing is desired. Allow to cool and set. Re-melt is preffered at above 60° C.

Example 74

| Ingredient | Wt % |
|---|---|
| Propylene Glycol | 4.00 |
| Cocoamidopropyl Betaine | 14.01 |
| Sodium Decyl Sulfate | 12.69 |
| Sodium Lauryl Sulfate | 16.89 |
| Mono alkyl Phosphate (acid form) | 22.43 |
| Potassium Hydroxide | 11.46 |
| Coco monoethanolamide | 11.89 |
| Bentonite clay | 5.00 |
| Kathon CG* | 0.03 |
| Disodium EDTA | 0.10 |
| Sodium Benzoate | 0.25 |
| Perfume | 1.26 |

*Methilchloroisothiazolinone (and) Methylisothiazolinone

Add Mono alkyl phosphate acid+Propylene glycol, heat to 80° C., slowly add the Potassium hydroxide whilst mixing. When neutralised add the water, anionic surfactants and nonioinic surfactants, mix until homogeneous, add all other ingredients except Bentonite clay and mix until dissolved. Add Bentonite clay and mix until well dispersed, sudden thickening of the batch occurs at this stage and powerful mixing is desired. Allow to cool and set. Re-melt is preffered at above 60° C.

II. Therapeutic Benefit Components

Examples 75–80

| Ingredient | Wt % | Wt % | Wt % | Wt % | Wt % |
|---|---|---|---|---|---|
| SEFA* Cottonate | 48.0 | 75.0 | 33.5 | 40.0 | — |
| SEFA* Behenate | 12.0 | 25.0 | 8.4 | 10.0 | — |
| Petrolatum | 10.0 | — | 7.0 | — | 24.0 |
| Cetearyl Methicone | | | | | 10.0 |
| C24-28 Methicone | | | | | 5.0 |

| Ingredient | Wt % | Wt % | Wt % | Wt % | Wt % |
|---|---|---|---|---|---|
| Glyceryl Tribehenate | 5.0 | — | 3.5 | — | — |
| Stearyl Alcohol | — | — | — | 5.0 | — |
| Paraffin | — | — | — | 15.0 | — |
| Cholesterol Ester | 25.0 | — | 17.5 | — | — |
| Lanolin | — | — | — | — | 61.0 |
| Glycerin | — | — | 28.0 | — | — |
| Triglyceryl monostearate | — | — | 1.9 | — | — |
| Decaglyceryl dipalmitate | — | — | 0.2 | — | — |
| Nonylphenol polyglycine ether[1] | — | — | — | 30.0 | — |

*SEFA is an acronym for sucrose esters of fatty acids
[1]Hamplex TNP, Hampshire Chemical Co.

Examples 81–85

| Ingredient | Wt % | Wt % | Wt % | Wt % | Wt % |
|---|---|---|---|---|---|
| Petrolatum (white) | 35.87 | 35.87 | — | — | 34.0 |
| Mineral oil | 11.0 | 13.0 | — | — | 10.0 |
| Jojoba oil | — | — | — | 4.5 | — |
| Castor oil | 10.0 | 9.0 | — | — | — |
| Cocoa butter | — | — | — | — | 5.0 |
| Diisostearyl trimethylpopane siloxy silicate | 20.0 | 20.0 | — | — | — |
| Polydimethylsiloxane, 500 cSt fluid | — | — | 0.7 | 1.5 | — |
| Decamethylcyclopentasiloxane | — | — | — | 16.5 | — |
| Octamethylcyclotetrasiloxane | — | — | — | 10.0 | — |
| Polydimethylsiloxane, gum | — | — | 5.9 | 7.5 | — |
| Stearyl methicone wax | — | — | — | 3.0 | — |
| Polybutene | — | — | — | 4.5 | — |
| Candelilla wax | 4.6 | 4.6 | — | — | 6.0 |
| Paraffin wax | — | — | — | 15.0 | 2.0 |
| Microcrystalline wax | — | — | — | 6.0 | 4.0 |
| Beeswax | 3.0 | 3.0 | — | — | 4.0 |
| Ozokerite wax | 6.0 | 6.0 | — | — | — |
| Carnauba wax | 3.0 | 3.0 | — | — | — |
| Hydrogenated castor oil | 0.50 | 0.50 | 4.0 | — | — |
| Silica | — | — | — | 4.5 | — |
| Sodium magnesium silicate | — | — | — | 1.5 | — |
| Tocopherol | 0.03 | 0.03 | — | — | — |
| Cyclomethicone | — | — | 59.0 | — | — |
| Stearyl alcohol | — | — | 25.5 | — | 9.0 |
| Cetyl alcohol | — | — | — | — | 9.0 |
| Glyceryl stearate | — | — | 2.6 | — | — |
| Acetylated monoglyceride | — | — | — | — | 15.0 |
| Diisostearyl maleate[1] | — | — | — | 6.0 | — |
| Glyceryl distearate | — | — | — | 9.5 | — |
| Glycerin | — | — | — | 6.0 | — |
| Water | — | — | — | 3.0 | — |
| Nonylphenol polyglycine ether[2] | — | — | 5.0 | — | — |
| Micronized titanium dioxide | — | 5.0 | — | — | — |
| Octyl methoxycinnamate | 5.0 | — | — | — | — |
| Fragrance & misc. | 1.0 | 1.0 | 1.0 | 1.0 | 2.0 |

[1]Available as Myvacet 7-07, about half acetylated, from Eastman Chemical Co.
[2]Available as Hamplex TNP, Hampshire Chemical Co.

Example 86

| Ingredient | Wt % |
|---|---|
| Polydecene[1] | 53.3 |
| Stearyl Alcohol | 7.7 |
| 12-Hydroxystearic acid | 13.5 |
| Nonylphenol polyglycine ether | 25.0 |
| Octyl methoxycinnamate | 1.5 |

[1]Puresyn 3000, Mobil Chemical Co.

Examples 87–89

| Ingredient | Wt % | Wt % | Wt % |
|---|---|---|---|
| Glycerin | 95.0 | 95.0 | 94.0 |
| Decaglyceryl dipalmitate[1] | 5.0 | 1.0 | 5.0 |
| Deceglyceryl dibehenate | — | 4.0 | — |
| Tribehenin | — | — | 1.0 |

[1]Available as Polyaldo 10-2-P from Lonza

Examples 90–94

| Ingredient | Wt % | Wt % | Wt % | Wt % | Wt % |
|---|---|---|---|---|---|
| Hydrophobic Phase: | | | | | |
| SEFA* cottonate | 4.65 | 4.65 | 15.5 | 15.5 | — |
| SEFA* behenate | 0.35 | 0.35 | 8.0 | 8.0 | — |
| Tribehenin | — | — | 6.0 | 6.0 | — |
| Petrolatum | — | — | 4.0 | 4.0 | 4.4 |
| Cocoa butter | — | — | — | — | 15.5 |
| C10–C30 Cholesterol/Lanosterol esters | — | — | 13.0 | 13.0 | — |
| Polyglyceryl-4 isostearate (and) Cetyl dimethicone (and) Hexyl laurate[2] | 5.0 | 5.0 | — | — | — |
| PEG 30 dipolyhydroxystearate[3] | — | — | 3.0 | — | — |
| Tetraglyceryl monostearate | — | — | — | 2.1 | — |
| Decaglyceryl dipalmitate | — | — | — | 0.90 | — |
| Ceresin wax | — | — | — | — | 5.5 |
| Beeswax | — | — | — | — | 7.0 |
| Lecithin, purified | — | — | — | — | 10.0 |
| 1-Monostearin | — | — | — | — | 10.0 |
| Hydrophilic Phase: | | | | | |
| Glycerin | 70.0 | 66.5 | 42.30 | 42.30 | 40.0 |
| Water | — | 3.5 | — | — | 5.0 |
| PVM/MA decadiene crosspolymer[4] | — | — | 0.25 | 0.25 | — |
| Sodium hydroxide (10% solution) | — | — | 0.25 | 0.25 | — |
| Gelatin | — | — | — | — | 2.6 |

-continued

| Ingredient | Wt % | Wt % | Wt % | Wt % | Wt % |
|---|---|---|---|---|---|
| Active skin care ingredients: | | | | | |
| Panthenol | 20.0 | 10.0 | 2.50 | — | — |
| Nicotinamide | — | 5.0 | 2.50 | 3.0 | — |
| Urea | — | 5.0 | 2.50 | 2.50 | — |
| Allantoin | — | — | 0.20 | 0.20 | — |
| Acetamidopropyl trimonium chloride | — | — | — | 2.0 | — |

*SEFA is an acronym for sucrose esters of fatty acids
[2]Available as Abil WE-09 from Goldschmidt
[3]Available as Arlacel P135 from ICI
[4]Available as Stabileze 06 from ISP Process for all emulsions:

Heat the hydrophobic phase to 70° C., add the hydrophobic active skin care ingredients, and stir until homogenous. Premix the hydrophilic phase ingredients with the hydrophilic active skin care ingredients, heating gently if necessary to dissolve or disperse them. Add these slowly to the hydrophobic phase, continuing to stir. Homogenize (high shear mixer; ultrasonic homogenizer; or high pressure homogenizer such as Microfluidizer from Microfluidics Corp.). Apply immediately to substrate surface or cool rapidly to below room temperature in ice or ice water. Store in controlled environment, under nitrogen if needed for chemical stability.

Examples 95–99

| Ingredient | Wt % | Wt % | Wt % | Wt % | Wt % |
|---|---|---|---|---|---|
| Hydrophobic Phase: | | | | | |
| SEFA* cottonate | — | — | 15.0 | 16.0 | — |
| SEFA* behenate | — | — | 7.5 | 4.0 | — |
| Tribehenin | — | — | 6.0 | — | — |
| Petrolatum | — | — | 4.0 | 4.0 | 4.4 |
| Cocoa butter | — | — | — | — | 15.5 |
| Polydecene[1] | 50.0 | 46.5 | — | — | — |
| C10–C30 Cholesterol/Lanosterol esters | — | — | 13.0 | 10.5 | — |
| PEG 30 dipolyhydroxystearate | — | — | 3.0 | 3.0 | — |
| Ceresin wax | — | — | — | — | 5.5 |
| Beeswax | — | — | — | — | 7.0 |
| Aluminum/magnesium hydroxystearate in mineral oil[2] | — | — | — | 7.5 | — |
| C30–38 Olefin/isopropyl maleate copolymer[3] | — | — | — | 2.5 | — |
| Polyethylene wax[4] | — | — | — | 1.0 | — |
| Lecithin, purified | — | — | — | — | 10.0 |
| Fragrance and misc. | — | — | 1.0 | — | — |
| 1-Monostearin | — | — | — | — | 10.0 |
| Hydrophlic Phase: | | | | | |
| Glycerin | 30.0 | 25.0 | 34.80 | 20.0 | 38.0 |
| Water | 8.0 | 8.0 | — | — | 5.0 |
| PEG 2000 | — | — | — | 17.0 | — |

| Ingredient | Wt % | Wt % | Wt % | Wt % | Wt % |
|---|---|---|---|---|---|
| PVM/MA decadiene crosspolymer | — | — | 0.25 | — | — |
| Sodium hydroxide (10% solution) | — | — | 0.25 | — | — |
| Gelatin | 9.50 | 9.50 | — | — | 2.6 |
| Active skin care ingredients: | | | | | |
| Nicotinamide | — | — | 2.50 | — | — |
| Menthol in 50% beta cyclodextrin | — | 2.50 | — | — | — |
| Ascorbic acid (natural) | — | 2.50 | — | — | — |
| Tocopherol (natural) | — | 1.00 | — | 2.50 | — |
| Sorbitol | — | — | 2.50 | — | — |
| Lactic acid | 2.5 | — | — | — | — |
| Urea | — | — | 2.50 | — | — |
| Allantoin | — | — | 0.20 | — | — |
| Triclosan | — | — | — | — | 1.50 |
| Chlorhexidine | — | — | — | — | 0.50 |
| Benzoyl peroxide | — | — | 5.0 | — | — |
| 15% Salicylic acid in PPG 14 butyl ether | — | — | — | 12.0 | — |
| Salicylic acid | — | — | 2.5 | — | — |

[1]Available as Puresyn 3000 from Mobil
[2]Available as Gilugel Min from Giulini Chemie
[3]Available as Performa 1608 from New Phase Technologies
[4]Available as Performalene 400 from New Phase Technologies Examples 100–104

Prepare as described in Examples 90–94.

| Ingredient | Wt % | Wt % | Wt % | Wt % | Wt % |
|---|---|---|---|---|---|
| Hydrophobic Phase: | | | | | |
| SEFA* cottonate | 20.5 | 15.5 | — | — | 16.0 |
| Mineral oil | — | — | 7.50 | — | — |
| SEFA* behenate | 8.0 | 8.0 | — | — | 8.0 |
| Tribehenin | 9.5 | 6.0 | — | — | 6.0 |
| Petrolatum (white or superwhite) | 4.0 | 4.0 | 22.6 | 3.0 | 4.0 |
| Candelilla wax | — | — | 4.50 | — | — |
| Paraffin wax | — | — | 3.00 | 14.0 | — |
| Microcrystalline wax | — | — | 1.50 | — | — |
| Beeswax | — | — | 3.00 | — | — |
| C10–C30 Cholesterol/Lanosterol esters | 18.0 | 13.0 | — | — | 13.0 |
| Laurylmethicone copolyol[1] | — | — | — | 5.0 | — |
| Acetylated monoglyceride[2] | — | — | 11.3 | — | — |
| Stearyl alcohol | — | — | 6.8 | — | — |
| Cetyl alcohol | — | — | 6.8 | — | — |
| Stearic acid | — | — | — | — | — |
| PEG 30 dipolyhydroxystearate | 4.5 | 3.0 | — | — | — |
| Decaglyceryl dipalmitate[3] | — | — | — | — | 0.90 |
| Tetraglyceryl monostearate | — | — | — | — | 2.10 |
| Fragrance, misc. | 1.0 | — | 3.0 | 2.0 | — |

-continued

| Ingredient | Wt % | Wt % | Wt % | Wt % | Wt % |
|---|---|---|---|---|---|
| Hydrophilic Phase: | | | | | |
| Glycerin | 22.8 | 27.5 | 25.0 | 38.0 | 41.0 |
| Decaglyceryl dipalmitate[3] | 2.5 | — | — | — | — |
| Calcium silicate microspheres[4] | — | 15.0 | — | — | — |
| Active skin care ingredients: | | | | | |
| Guar hydroxypropyl-trimonium chloride | 1.00 | — | — | — | — |
| Chitosan glycolate | — | 2.50 | — | — | — |
| Nicotinamide | 1.50 | 2.50 | 2.50 | — | — |
| 0.2% Carbopol 940 aqueous solution, pH 6.0 | — | — | — | 38.0 | — |
| Retinol | — | — | — | — | 2.50 |
| Phytantriol[5] | 1.00 | — | — | — | — |
| Urea | 2.50 | 3.0 | 2.50 | — | — |
| Vitamin C | — | — | — | — | 2.50 |
| Borage oil | — | — | — | — | 2.50 |
| Ascorbyl palmitate | — | — | — | — | 1.50 |
| Acetamidopropyl trimonium chloride[6] | 2.50 | — | — | — | — |

[1]Available as Dow Q2-5200, Dow Corning
[2]Available as Myvacet 7-07, about half acetylated, from Eastman Chemical Co.
[3]Available as Polyaldo 10-2-P from Lonza
[4]Available as Celite C from Celite Co.
[5]Available as Hydagen CMF from Henkel
[6]Available as Incromectant AQ from Croda Example 101: Glycerin incorporated into microspheres, then blended into molten lipid phase and cooled for storage or applied to substrate.

Examples 105–110

Prepare as described in Examples 90–94.

| Ingredient | Wt % | Wt % | Wt % | Wt % | Wt % | Wt % |
|---|---|---|---|---|---|---|
| Hydrophobic Phase: | | | | | | |
| SEFA* cottonate | 16.0 | 16.0 | 16.0 | 16.0 | 16.0 | 16.0 |
| SEFA* behenate | | 8.0 | 8.0 | 8.0 | 8.0 | 8.0 |
| Tribehenin | 6.0 | 6.0 | 6.0 | 6.0 | 6.0 | 6.0 |
| Petrolatum (white or superwhite) | 4.0 | 4.0 | 4.0 | 4.0 | 4.0 | 4.0 |
| C10–C30 Cholesterol/Lanosterol esters | 13.0 | 13.0 | 13.0 | 13.0 | 13.0 | 13.0 |
| Stearyl dimethicone | 2.0 | — | — | — | — | — |
| Dimethicone hydroxystearate | 4.0 | — | — | — | — | — |
| Dimethicone copolyol behenate | 2.0 | — | — | — | — | — |
| PEG 30 dipolyhydroxy stearate | — | — | 3.00 | — | 3.00 | — |
| Sodium lauroyl glutamate | — | — | — | 2.00 | — | — |
| Sodium stearoyl lactylate | — | — | — | 2.00 | — | — |
| Calcium stearate | — | — | — | — | — | 5.0 |
| Decaglyceryl dipalmitate | 0.90 | 0.90 | — | 0.90 | — | 0.90 |
| Tetraglyceryl monostearate | 2.10 | 2.10 | — | 2.10 | — | 2.10 |
| Fragrance, misc. | 1.00 | 1.00 | 1.00 | 1.00 | 1.00 | 1.00 |
| Hydrophilic Phase: | | | | | | |
| Glycerin | 44.5 | 42.5 | 35.5 | 35.5 | 25.0 | 43.0 |
| 75% Polyethyleneimine[1] in water, pH 6.5 | — | — | 4.50 | 4.50 | — | — |
| Water | — | — | — | — | — | 2.0 |
| Decaglyceryl dipalmitate | — | — | 2.50 | 2.50 | — | — |
| Fumed silica | — | — | — | — | 20.0 | — |
| Propylene glycol alginate[2] | — | — | — | — | — | 2.0 |
| Active skin care ingredients: | | | | | | |
| Nicotinamide | — | 2.00 | — | — | 2.00 | — |
| Chitosan | — | 1.50 | — | — | — | — |
| Green tea extract | 4.50 | — | — | — | — | — |
| Aloe vera gel | — | 3.0 | — | — | — | — |
| Vitamin C | — | — | 2.50 | — | — | — |
| Ascorbyl palmitate | — | — | 2.00 | 2.50 | — | — |
| Acetamidopropyl trimonium chloride | — | — | 2.00 | — | 2.00 | — |

[1]Available as Epomin SP-018 from Nippon Shokubai Co.
[2]Available as Kelcoloid HVF from Kelco Examples 111–113

| Ingredient | Wt % | Wt % | Wt % |
|---|---|---|---|
| Hydrophobic Phase: | | | |
| Lecithin, purified[1] | 15.4 | 10.3 | 10.8 |
| Decane | 28.6 | 19.2 | 15.0 |
| Mineral Oil | — | — | 5.0 |
| Tricontanyl PVP[2] | — | — | 26.0 |
| Stearyl alcohol | — | 13.0 | — |
| 12-hydroxystearic acid | — | 19.4 | — |
| Hydrophilic Phase: | | | |
| Glycerin | 28.0 | 18.8 | 19.6 |
| Propylene glycol | 28.0 | 18.8 | 19.6 |
| Active skin care ingredients: | | | |
| Triclosan | — | 0.20 | — |
| Salicylic acid | — | 0.40 | — |
| Nicotinamide | — | — | 4.0 |

[1]Available as Epikuron 200 from Lucas Meyer
[2]Available as Ganex WP-660 from ISP Stir all ingredients together until microemulsion forms. Add skin care ingredients first to the phase which most closely matches their solubility parameter. When adding waxes, heat slowly just to the wax melting point, disperse by stirring, and add to substrate or cool to room temperature and store.

Examples 114–116

| Ingredient | Wt % | Wt % | Wt % |
|---|---|---|---|
| Hydrophobic Phase: | | | |
| Isohexadecane | 42.29 | 43.0 | 28.3 |
| Sodium diocytl sulfosuccinate[2] | 10.62 | 7.0 | 7.1 |
| Hydrophilic Phase: | | | |
| Glycerin | 35.17 | 19.0 | 23.6 |
| Water | 11.72 | 19.0 | 7.8 |
| Carnauba wax | — | — | 29.0 |
| Gelatin | — | 6.0 | — |
| Active skin care ingredients: | | | |
| Triclosan | 0.20 | — | — |
| Titanium dioxide, cosmetic | — | — | 4.2 |
| Titanium dioxide, micronized | — | 4.2 | — |
| Salicylic acid | — | 1.8 | — |

[1]Available as Epikuron 200 from Lucas Meyer
[2]Available as Aerosol OT from Pfaltz and Bauer Add skin care ingredients first to the phase which most closely matches their solubility parameter. Then, stir all ingredients together until microemulsion forms. Coat onto substrate surface.

Examples 117–122

| | Wt % | Wt % | Wt % | Wt % | Wt % | Wt % |
|---|---|---|---|---|---|---|
| Part A | | | | | | |
| Sodium lauroyl ether sulfate (SLES, add as 27% active) | 15.0 | 6.51 | 6.20 | — | — | 5.9 |
| Cocamidopropyl betaine[1] | 13.5 | 5.85 | 5.57 | 5.82 | 5.19 | 5.3 |
| Sodium lauroyl sarcosinate[2] | 1.35 | 0.60 | 0.57 | 6.01 | 5.36 | 0.54 |
| Decylpolyglucose[3] | — | — | — | 5.80 | 5.18 | — |
| Lauryl alcohol | 1.31 | 0.56 | 0.54 | — | — | 0.54 |
| Polyethyleneimine[4] | 7.87 | 3.38 | 3.22 | 2.64 | 2.36 | 3.2 |
| Citric acid (add as 50% aqueous solution) | 0.32 | 0.11 | 0.11 | — | — | 0.09 |
| Tetrasodium EDTA | 0.28 | — | — | — | — | — |
| Sulfuric acid | 5.4 | 2.37 | 2.25 | — | — | 2.2 |
| Preservative, fragrance | 0.62 | 0.45 | 0.43 | 2.86 | 2.55 | 0.3 |
| Sodium sulfate | 7.9 | 3.47 | 3.21 | — | — | 3.0 |
| Glycerin | 26.45 | 56.7 | 46.4 | 44.1 | 39.36 | 44.8 |
| Sorbitol | — | — | 5.0 | — | — | — |
| SEFA* cottonate | — | — | — | — | 12.8 | — |
| SEFA* behenate | — | — | — | — | 8.0 | — |
| Part B - Polymer gelling agents | | | | | | |
| Gelatin | — | — | — | — | 4.2 | — |
| Polyacrylamide and isoparaffin[5] | — | — | — | 7.5 | — | — |
| Polyurethane latex in 50% isopropanol[6] | — | — | — | — | — | 34.1 |
| Polyacrylate copolymer[7] | — | — | — | 7.5 | — | — |
| Polystyrene sulfonates copolymer[8] | — | — | 1.1 | — | — | — |
| Chitosan lactate | — | — | 5.4 | — | — | — |
| Part C - Physical gelling agents | | | | | | |
| 12-Hydroxystearic acid | 10.0 | — | — | 10.66 | — | — |
| Stearyl alcohol | 10.0 | 20.0 | 20.0 | 7.11 | 15.0 | — |

*SEFA is an acronym for sucrose esters of fatty acids
[1]Available as Tegobetaine F from Goldschmidt
[2]Available as Hamposyl L-30 (type 721) from Hampshire Chemical, 31% active
[3]Available as Plantaren 2000NP from Henkel
[4]Available as Epomin SP-018, molecular weight about 1800, from Nippon Shokubai Co.
[5]Available as Carbopol Ultrez from B.F. Goodrich
[6]Available as Sancure 2710 from B.F. Goodrich, prepared as premix comprising about 20% polymer, 30% water, 50% IPA
[6]Available as Sepigel 305 from Seppic Corp.
[7]Available as AQ38S from Eastman Chemical Blend the surfactants and fatty alcohol while heating to 65° C. with a low speed impeller mixer. Remove from heat, allow to cool to 65° C. while continuing to mix. Add the cationic polymer and stir until homogeneous. Slowly add remaining Part A ingredients while stirring. Homogenize to disperse the SEFA as an emulsion. Titrate with concentrated sulfuric acid until a pH of about 6.5 is reached. Prepare a dried mixture by spreading the Part A composition in trays and drying in a suitable (vacuum or convection) oven at a temperature not exceeding 65° C. until essentially no water remains. Blend the dried Part A ingredients with the polymeric gelling agents from Part B, heat to dissolve or disperse. Blend the resulting composition with the physical gelling agents. Heat to melt and dissolve gelling agents into the composition. Apply to substrate surface(s) or cool to room temperature and store.

Examples 123–128

Prepare as described in Examples 117–122.

| | Wt % | Wt % | Wt % | Wt % | Wt % | Wt % |
|---|---|---|---|---|---|---|
| Part A | | | | | | |
| Sodium lauroyl sarcosinate[1] | 8.87 | — | — | 11.4 | 10.8 | 10.8 |
| Polyethyleneimine[2] | 7.39 | 7.50 | 7.50 | 9.5 | 9.0 | 9.0 |
| Water | 4.43 | 3.00 | 3.00 | 5.7 | 5.4 | 5.4 |
| Sulfuric acid | 6.36 | QS | QS | 8.1 | 7.7 | 7.7 |
| Glycerin | 34.45 | 52.5 | 45.0 | 41.3 | 39.25 | 34.25 |
| Propylene glycol | 2.50 | | | | | |
| Urea | — | 2.50 | 2.50 | 2.0 | 1.9 | 1.9 |
| Panthenol | — | — | — | 2.0 | 1.9 | 1.9 |
| Nicotinamide | — | 2.50 | 2.50 | 2.0 | 1.9 | 1.9 |
| Polymethyl- | — | — | — | — | 4.20 | 4.20 |

-continued

|  | Wt % | Wt % | Wt % | Wt % | Wt % | Wt % |
|---|---|---|---|---|---|---|
| silsesquioxane³ | | | | | | |
| Mica, pearlescent | — | — | — | — | 3.85 | 3.85 |
| Stearylmethicone wax | — | — | — | — | — | 5.0 |
| SEFA cottonate | — | — | 5.0 | — | — | — |
| Petrolatum | — | — | 5.0 | — | — | — |
| Part B - Polymer gelling agents | | | | | | |
| Gelatin | — | — | — | — | — | 0.1 |
| Polyacrylamide and isoparaffin⁴ | 16.0 | 12.0 | 12.0 | — | — | — |
| Part C - Physical gelling agents | | | | | | |
| 12-Hydroxystearic acid | 12.0 | 12.0 | 10.5 | — | — | — |
| Carnauba wax | — | — | — | 18.0 | 14.1 | 14.1 |
| Stearyl alcohol | 8.0 | 8.0 | 7.0 | — | — | — |

[1]Available as Hamposyl L-95 from Hampshire Chemical, dry
[2]Available as Epomin SP-018, molecular weight about 1800, from Nippon Shokubai Co.
[3]Available as Tospearl 145A from Kobo, Inc.
[4]Available as Sepigel 305 from Seppic Corp.

Examples 129–132

| Component | Wt % | Wt % | Wt % | Wt % |
|---|---|---|---|---|
| SEFA* Cottonate | — | 62.0 | 52.0 | — |
| Petrolatum | — | — | 4.5 | — |
| Stearyl Alcohol | 4.0 | — | — | — |
| Stearic Acid | 3.0 | — | — | — |
| Lanolin | — | 20.0 | 13.0 | — |
| Ethylene vinyl acetate polymer¹ | — | 10.0 | 10.0 | — |
| Polydecene² | — | — | 2.0 | 2.0 |
| Sodium lauroyl sarcosinate³ | 25.0 | 3.00 | 3.0 | — |
| Lauryl betaine⁴ | — | 1.50 | 2.0 | — |
| Lauroamphoacetate⁵ | — | — | — | 5.25 |
| Sodium laureth-3 sulfate⁶ | — | — | — | 10.5 |
| Cocamide MEA⁷ | — | — | — | 2.80 |
| Sulfuric acid | QS | — | — | — |
| Guar hydroxypropyltrimonium chloride | 0.50 | — | 0.50 | — |
| Cholesterol⁸ | 9.0 | 1.0 | — | — |
| Nonylphenol polyglycine ether⁹ | — | — | 5.0 | — |
| Micronized titanium dioxide | — | — | 4.0 | — |
| Octyl methoxycinnamate | — | — | 4.0 | — |
| Nicotinamide | — | 2.5 | — | — |
| Glycerin | 10.0 | — | — | 3.00 |
| Water | 48.5 | — | — | 55.95 |
| PEG 6 caprylic/capric glycerides | — | — | — | 3.40 |
| Maleated soybean oil | — | — | — | 1.50 |
| Soybean oil (deodorized) | — | — | — | 8.0 |
| Palm kernel fatty acids | — | — | — | 2.60 |
| Polyquaternium-10 | — | — | — | 0.40 |
| Fragrance, preservative, misc. | — | — | — | 4.60 |

-continued

| Component | Wt % | Wt % | Wt % | Wt % |
|---|---|---|---|---|

*SEFA is an acronym for sucrose esters of fatty acids
[1]Available Elvax 40W from DuPont
[2]Available as Puresyn 3000 from Mobil
[3]Available as Hamposyl L95 (solid) or L30 (30% active in water) from Hampshire Chemical, e.g.
[4]Available as Empigen BS98 from Albright & Wilson (80% betaine, 20% salt)
[5]Available Empigen CDL60 from Albright & Wilson
[6]Available as Empicol ESC3 from Albright & Wilson
[7]Available as Empilan CME/G from Albright & Wilson
[8]Available as Super Hartolan from Croda
[9]Hamplex TNP, Hampshire Chemical Co.

Melt the lipid components, add the water (if applicable) and humectant(s), add the surfactant and continue to heat and stir until homogeneous. Cool to room temperature and add the skin care active(s) and deposition agent(s). Adjust pH to about 7.0 with sulfuric acid. Spray, roll, dip or otherwise apply to substrate and dry (if water containing) before packaging.

III. Laminate Webs

The laminate webs in Table 1 below are intended to exemplify the various configurations envisioned as suitable for the articles of the present invention. Because the choice of outer and inner layers and combinations is virtually infinite, the examples shown are meant to be illustrative of possible structures of the laminate web, and are not meant to be limiting to any particular material or structure. In the various configurations shown, the layers are numbered in order of structural proximity from one outer layer to the other of the laminate web. Therefore, layer 1 is always an outer layer, and the last numbered layer is likewise an outer layer.

Clopay formed films were obtained from Clopay, Cincinnati, Ohio. As used herein, "formed film" means a macroscopically-expanded three-dimensional plastic web comprising a continuum of capillary networks originating in and extending from one surface of the web and terminating in the form of apertures in the opposite surface thereof.

Elastomeric formed films are obtained from Tredegar Film Products, Terre Haute, Ind. Such films are an improvement in the aforementioned Radel et al. web as disclosed in the above-mentioned commonly assigned, copending U.S. patent application Ser. No. 08/816,106 entitled Tear Resistant Porous Extensible Web, filed Mar. 14, 1997 in the name of Curro et al. The Curro '106 application discloses elasticized polymeric webs generally in accordance with U.S. Pat. No. 4,342,314 that may be produced from elastomeric materials known in the art, and may be laminates of polymeric materials. Laminates of this type can be prepared by coextrusion of elastomeric materials and less elastic skin layers and may be used in the body hugging portions of absorbent garments, such as the waistband portions and leg cuffs.

High internal phase emulsion open cell foam materials can be made generally in accordance with the teachings of the above mentioned U.S. Pat. No. 5,260,345 and U.S. Pat. No. 5,268,224.

BBA and Corovin/BBA nonwovens were obtained form BBA, Greenville, S.C.

BOUNTY® paper towels were obtained from The Procter & Gamble Co., Cincinnati, Ohio.

For the materials shown below, the basis weight is expressed in grams per square meter (gsm). Low density polyethylene is denoted "LDPE"; polypropylene is denoted as "PP"; and polyethylene is denoted as "PE". Spunbond is denoted as "SB".

TABLE 1

Examples of Laminate Webs Suitable for Use in the Articles of the Present Invention. As used in the articles of the presentation the laminated webs would be apertured by formation firstly of narrow bond sites using a heated calendaring roll and secondly by stretching of the web causing breakage of the narrow bond sites using a ring-rolling process as described in copending U.S. application Ser. No. 09/467,938, which was filed on Dec. 21, 1999.

| Example No. | Layer 1 | Layer 2 | Layer 3 | Layer 4 | Layer 5 |
|---|---|---|---|---|---|
| 132 | 30 gsm LDPE SB nonwoven from Corovin/BBA | 42 gsm BOUNTY ® Paper Towel | 30 gsm LDPE SB nonwoven from Corovin/BBA | | |
| 133 | 30 gsm LDPE SB nonwoven from Corovin/BBA | 42 gsm BOUNTY ® Paper Towel | 42 gsm BOUNTY ® Paper Towel | 30 gsm LDPE SB nonwoven from Corovin/BBA | |
| 134 | 80/20 (PE/PP) 30 gsm SB nonwoven from BBA | 42 gsm BOUNTY ® Paper Towel | 80/20 (PE/PP) 30 gsm SB nonwoven from BBA | | |
| 135 | 80/20 (PE/PP) 30 gsm SB nonwoven from BBA | 42 gsm BOUNTY ® Paper Towel | 23 gsm PE formed film from Clopay | 50/50 (PE/PP) 30 gsm SB nonwoven from BBA | |
| 136 | 30 gsm LDPE SB nonwoven from Corovin/BBA | 88 gsm elastomeric formed film from Tredegar | 42 gsm BOUNTY ® Paper Towel | 30 gsm LDPE SB nonwoven from Corovin/BBA | |
| 137 | 30 gsm LDPE SB nonwoven from Corovin/BBA | Spray hot melt adhesive from Ato-Findley approx. 12 gsm | 62 gsm High Internal Phase Emulsion open cell foam | Spray hot melt adhesive from Ato-Findley approx. 12 gsm | 30 gsm LDPE SB nonwoven from Corovin/BBA |
| 138 | 27 gsm high elongation carded PP nonwoven from BBA | 42 gsm BOUNTY ® Paper Towel | 60 gsm laminate of 80/20 50/50 (PE/PP) nonwoven from BBA | | |
| 139 | 50/50 (PE/PP) 15 gsm SB nonwoven from BBA | 21 gsm BOUNTY ® Paper Towel | 25 gsm formed film from Tredegar | 21 gsm BOUNTY ® Paper Towel | 50/50 (PE/PP) 15 gsm SB nonwoven from BBA |

IV. Personal Care Articles

Example 140

Prepare a representative skin cleansing article in the following manner.

Four grams of the cleansing component of any one of Examples 1–74 is applied to one side of a web of polyester batting substrate by heating the composition to its recommended remelt temperature in a hotmelt tank such as a Meltex hotmelt tank as available from Nordson Engineering GmbH, feeding it to a heated slot coating die and applying in four stripes each 1 cm wide and 2 cms apart. The coated web then passes through a cooling tunnel to solidify the coated formula. Products of 16 cm×12 cm are then cut out.

Example 141

The article of example 140 where the coated batting web is combined with any apertured laminated web of examples 132–139. Finished articles comprising rectangles of 160 mm×120 mm with rounded corners are cut out.

Example 142

Prepare a representative skin cleansing article in the following manner.

The cleansing component of any one of Examples 1–74 is applied to one side of a first substrate by extruding it through a coating head continuously in four lines separated by a distance of 20 mm, 40 mm, and 20 mm respectively, measuring widthwise across the web, making a pair of parallel lines on each side of the web. The cleansing component is extruded at a rate to yield 4.4 grams of cleansing component per finished article. The substrate is an airlaid, lofty, low density batting. The batting comprises a blend of 30% 15 denier PET fibers, 35% 3 denier bicomponent fibers with PET core and PE sheath, and 35% 10 denier bicomponent fibers of the same core-sheath composition, and has a basis weight of about 100 grams per square meter (gsm). A second web which is a spunlace blend of 70% rayon and 30% PET fibers, bonded with a styrene-butadiene adhesive is hydroapertured to form holes about 2 mm in diameter and has a basis weight of about 70 gsm,iand s continuously fed over the first substrate placing it in contact with the surfactant-70 gsm,iand s continuously fed over the first substrate placing it in contact with the surfactant-containing layer. The webs are continuously fed to an ultrasonic sealer which seals a dot pattern comprising a grid of 4 mm diameter sealing points spaced evenly across the web. The web is cut into individual articles measuring about 120 mm×160 mm rectangles with rounded corners, which has a total of about 51 sealing points per article.

Example 143

Prepare a representative skin cleansing and conditioning article in the following manner.

One gram of the skin conditioning composition of any one of Examples 75–131 is applied to the apertured nonwoven side of the finished article of Example 142. The composition is applied by slot coating the composition as a hot liquid (60–70° C.) to the article surfaces in two stripes.

Example 144

Prepare a representative skin cleansing and conditioning article in the following manner.

3.6 grams of any one of the cleansing components of examples 1–74 is heated in a hotmelt tank, fed to a heated die and slot coated onto a moving web of batting in 2 pairs of 2 stripes of 8 mm width at 16 mm center to center spacing with a gap of 64 mm between the 2 pairs of stripes. 0.8 g of any one of the skin conditioning compositons of examples 75–131 is applied, by hotmelt coating, in 2 stripes between the stripes of cleansing component. The batting comprises a blend of 30% 15 denier PET fibers, 35% 3 denier bicomponent fibers with PET core and PE sheath, and 35% 10 denier bicomponent fibers of the same core-sheath composition, and has a basis weight of about 90 grams per square meter (gsm). A second substrate is then combined with the batting such that it contacts the coated side of the batting. The second substrate is any apertured laminated web of examples 132–139. The combined webs are ultrasonically bonded together in a pattern of 3 mm diameter dots evenly spaced at 16 mm centre to centre spacings. Finished articles in the form of 120 mm×160 mm rectangles with rounded corners are cut out using a rotary die cutter.

Example 145

Prepare a representative skin cleansing article in the following manner.

The cleansing component of any one of Examples 1–74 is applied to one side of a first substrate by melting the composition in a feedtank, feeding it to a spray coating head and spraying evenly over the surface of the substrate. The cleansing component is applied at a rate to yield 3 grams of cleansing component per finished article. The coated web is allowed to cool such that the cleansing component solidifies on the web. The substrate is an airlaid, lofty, low density batting which comprises a blend of 30% 15 denier PET fibers, 35% 3 denier bicomponent fibers with PET core and PE sheath, and 35% 10 denier bicomponent fibers of the same core-sheath composition, and has a basis weight of about 100 grams per square meter (gsm). A second substrate web which is a spunlace blend of 70% rayon and 30% PET fibers, bonded with a styrene-butadiene adhesive, which is hydroapertured to form holes about 2 mm in diameter and having a basis weight of about 70 gsm is continuously fed over the first substrate placng it in contact with the surfactant layer. The webs are continuously fed to an ultrasonic sealer which seals a dot pattern comprising a grid of 4 mm diameter sealing points spaced evenly across the web. The web is cut into individual articles measuring about 120 mm×160 mm rectangles with rounded corners.

Examples 146

Prepare representative skin cleansing articles with the cleansing components of any one of Examples 1–74 in the following manner.

The cleansing component is melted in a feed tray and is applied to a first batting substrate by gravure printing. The cleansing component is applied at a rate to yield 3.6 grams per finished article in a diamond pattern. The batting comprises a blend of 30% 15 denier PET fibers, 35% 3 denier bicomponent fibers with PET core and PE sheath, and 35% 10 denier bicomponent fibers of the same core-sheath composition, and has a basis weight of about 90 grams per square meter (gsm).

The coated batting is combined with a second non-woven substrate comprising an apertured spunbond PE/PP nonwoven. The webs are continuously fed to an ultrasonic sealer which seals a dot pattern comprising a grid of 4 mm diameter sealing points spaced evenly across the web. The web is cut into individual articles measuring about 120 mm×160 mm rectangles with rounded corners.

Examples 147

Prepare representative skin cleansing and conditioning articles with the cleansing components of any one of Examples 1–74 and any one of the skin conditioning compositions of Examples 75–131 in the following manner.

Four stripes of the liquid cleansing component are hotmelt coated continuously on a moving first web which is an airlaid, lofty, low density batting. The batting comprises a blend of 30% 15 denier PET fibers, 35% 3 denier bicomponent fibers with PET core and PE sheath, and 35% 10 denier bicomponent fibers of the same core-sheath composition, and has a basis weight of about 100 grams per square meter (gsm), and is airlaid and heat bonded with no adhesive. The cleansing component is heated to melting point and held in a reservoir at about 65° C. and fed by pump to an extrusion head which continuously meters 4 stripes onto the web at an even spacing across the web, to achieve a final add-on rate of about 4 grams of composition per finished article. . . . The skin conditioning composition is slot coated in stripes between the stripes of the cleansing compostion onto the exposed batting surface at a rate of 1 gram of composition per finished article while hot, cooling on the article surface to solidify. A second web which is an apertured spunbond PE/PP nonwoven is continuously fed onto the first web. The webs are continuously sealed and cut into 120 mm by 160 mm rectangles with rounded corners. The articles are packaged until ready for use.

Example 148

Prepare representative skin cleansing and conditioning articles in the following manner, utilizing the skin conditioning compositions of any one of Examples 75–131.

The cleansing component of any one of Examples 1–74 is heated until molten or semi-molten in a tray. A continuous web of batting is fed through the tray such that it becomes impregnated with the molten cleansing component. The batting is then nipped between two rollers to remove excess coating and leave a coat weight equivalent to 2.5 grams of cleansing component per finished article. The coated batting is cooled to solidify the coated cleansing component and the skin conditioning composition is slot coated while hot (60–70° C.) in two stripes onto the exposed batting surface at a rate of 1 gram of composition per finished article, cooling on the article surface to solidify. The coated batting is then combined with a second apertured non-woven layer. The combined webs are ultrasonically bonded together in a pattern of wavy lines about 1 cm long and spaced 1 cm apart. Finished articles of 12 cm×16 cm are then cut out.

Example 149

Prepare representative skin cleansing and conditioning articles in the following manner, utilizing the skin conditioning compositions of any one of Examples 75–131.

Three grams of the cleansing component of any one of Examples 1–74 is applied evenly to a lofty batting by kiss coating. The formula is heated in a tray until molten or semimolten, a roller rotates through the tray picking up a coating of the cleansing component. It then contacts the lofty batting web transferring the coating to the web. The batting is an airlaid, lofty, low density batting comprising a blend of 30% 15 denier PET fibers, 35% 3 denier bicomponent fibers with PET core and PE sheath, and 35% 10 denier bicomponent fibers of the same core-sheath composition, and has a basis weight of about 100 grams per square meter (gsm). A layer of fibrous nonwoven which is a hydroentangled blend of 55% cellulose and 45% polyester having a basis weight of about 65 gsm (available as Technicloth II from The Texwipe Company, Saddle River, N.J.) is placed over the cleansing component coated side of the batting. The layers are sealed together using interlocking sealing plates using an unheated plate having inverted thimble-shaped reservoirs spaced evenly in a hexagonal grid pattern. The thimble shaped reservoirs are about 1.2 cm diameter at the base and are spaced about 2 cm apart, center-to-center. The land area between the dimples on the unheated plate is concave inwards by several mm, forming an interconnected trough. The heated plate has an external ridge which fit precisely into the trough on the land area of the unheated plate. The heated plate contacts the cellulose/polyester substrate and a heat seal is effected using pressure-platen heat sealing device such as a Sentinel Model 808 heat sealer available from Sencorp, Hyannis, Mass. The resulting unfinished article has pronounced thimble shapes rising up on the batting side, and shorter dimples or 'buttons' rising up on the cellulose/polyester substrate side of the article, making both sides easy to grip. The article is cut into a rectangle about 120 mm by 160 mm. Two grams of skin conditioning composition per article is bead coated into the trough area while the composition is hot, and allowed to cool and solidify. The article is packaged until ready for use.

Example 150

Prepare a representative skin cleansing and conditioning article in the following manner.

Two grams of the cleansing component of any of Examples 1–74 is heated until molten and screen printed in a logo onto a lofty batting web. The batting is an 80gsm Polyester batting, comprising 60% 12 denier hollow PET fibres and 40% 4 denier bicomponent PET fibres which are thru-air bonded.

A skin conditioning inverse emulsion paste is prepared for use with the article, as follows:

| Ingredient | WT % |
|---|---|
| PEG 30-dipolyhydroxystearate | 3.0 |
| SEFA cottonate | 20.0 |
| Petrolatum | 4.0 |
| Tribehenin | 5.0 |
| C10–C30 Cholesterol/Lanosterol Esters | 13.0 |
| SEFA behenate | 5.0 |
| Glycerin | 50.0 |

The lipid soluble ingredients are heated to 70° C. while stirring. Glycerin is slowly added with vigorous stirring. The composition is homogenized. Two grams of the skin conditioning inverse emulsion paste is slot coated hot in two stripes onto the uncoated areas of the batting. The composition quickly cools to a semi-solid paste. The coated batting is combined with an apertured PE/PP spunbond non-woven and the webs bonded together ultrasonically using a bond pattern consisting of wavy line about 1 cm long and at 1 cm spacings. Finished articels of 12 cm×16 cm are cut out and packaged ready for use.

Example 151

Prepare representative skin cleansing and conditioning kits in the following manner.

A skin cleansing article is prepared. The cleansing component of any of Examples 1–74 is applied to one side of a first substrate by hotmelt coating through a heated die head continuously in four lines separated by a distance of 20 mm, 40 mm, and 20 mm respectively, measuring widthwise across the web, making a pair of parallel lines on each side of the web. The cleansing component is coated at a rate to yield 4.4 grams of cleansing component per finished article. The substrate is an airlaid, lofty, low density batting. The batting comprises a blend of 30% 15 denier PET fibers, 35% 3 denier bicomponent fibers with PET core and PE sheath, and 35% 10 denier bicomponent fibers of the same core-sheath composition, and has a basis weight of about 100 grams per square meter (gsm). A second web which is a spunlace blend of 70% rayon and 30% PET fibers, bonded with a styrene-butadiene adhesive, which is hydroapertured to form holes about 2 mm in diameter and having a basis weight of about 70 gsm is continuously fed over the first substrate placing it in contact with the surfactant-containing layer. The webs are continuously fed to an ultrasonic sealer which seals a dot pattern comprising a grid of 4 mm diameter sealing points spaced evenly across the web. The web is cut into individual articles measuring about 120 mm×200 mm rectangles with rounded corners.

A skin conditioning article is prepared. The conditioning composition of any one of Examples 75–131 is applied to one side of a first substrate by extruding it through a coating head continuously in four strips, each 5 mm wide, separated by a distance of 20 mm, 40 mm, and 20 mm respectively, measuring widthwise across the web, making a pair of parallel lines on each side of the web. The composition is extruded at a rate to yield 3 grams of composition per finished article. The substrate is a spunlace blend of 70% rayon and 30% PET fibers, bonded with a styrene-butadiene adhesive, which is hydroapertured to form holes about 2 mm in diameter and having a basis weight of about 70 gsm. A second web which is an airlaid, lofty, low density batting is continuously fed over the first substrate placing it in contact with the first substrate on the side containing no skin conditioning composition. The batting comprises a blend of 30% 15 denier PET fibers, 35% 3 denier bicomponent fibers with PET core and PE sheath, and 35% 10 denier bicomponent fibers of the same core-sheath composition, and has a basis weight of about 100 grams per square meter (gsm). The webs are continuously fed to an ultrasonic sealer which seals a dot pattern comprising a grid of 4 mm diameter sealing points spaced evenly across the web. The web is cut into individual articles measuring about 120 mm×160 mm rectangles with rounded corners, which has a total of about 51 sealing points per article.

The skin cleansing article and the skin conditioning article are packaged together in a single package.

Example 152

Prepare representative skin cleansing and conditioning articles with the hotmelt cleansing compositions of any one of Examples 1–74 in the following manner.

A substrate is prepared which is a hydroentangled blend of fibers, having softer, finer denier fibers on one side and coarser fibers on the second side. The substrate is prepared by airlaying two webs comprising 10 denier polyester (PET) fibers, one web on top of the other, each having a basis weight of about 20 gsm. A web of polypropylene scrim having a diameter about 100 microns, laced at about 0.8 cm intervals is fed over the fibrous webs continuously as a third web. Fourth and fifth webs comprising 3 denier polyester fibers are airlaid at about 20 gsm each on top of the web. The webs are hydroentangled and to fix them into a single web unit, and dried on drying cans until moisture free and about 20% shrinkage due to relaxation of the scrim has occurred.

An intermediate $T_g$ (about 15° C.) waterborne acrylic copolymer is added to the coarse fiber side of the web by kiss roll application at a rate of about 5 gsm wet add-on rate, and dried. Surfactant is continuously added to the web by slot coating the composition evenly across the web coarse fiber side at a rate of about 80 gsm. The skin conditioning composition of any one of Examples 75–131 is continuously added to the web by slot coating the composition evenly across the web soft fiber side at a rate of about 50 gsm. The substrate web is cut into individual articles measuring about 120 mm×480 mm rectangles with rounded corners using a hot cutting roll causing the scrim fibers to shrink back slightly from the edge of the article as they are cut.

Example 153

Prepare a representative skin cleansing and conditioning article in the following manner.

The cleansing component of any one of Examples 1–74 is blended with any one of the therapuetic benefits compositions of examples 75–131 in the ratio 4:1 cleansing component:therapeutic benefit component. The compositions are blended above their melt point using high shear mixing and then allowed to solidify. The resultant cleansing and conditioning coposition is applied to one side of a first substrate by extruding it through a coating head continuously in four lines separated by a distance of 20 mm, 40 mm, and 20 mm respectively, measuring widthwise across the web, making a pair of parallel lines on each side of the web. The cleansing and conditioning composition is extruded at a rate to yield 6.0 grams of conposition per finished article. The substrate is an airlaid, lofty, low density batting. The batting comprises a blend of 30% 15 denier PET fibers, 35% 3 denier bicomponent fibers with PET core and PE sheath, and 35% 10 denier bicomponent fibers of the same core-sheath composition, and has a basis weight of about 100 grams per square meter (gsm). The coated batting web is combined with any apertured laminated web of examples 132–139 and the two are bonded together ultrasonically. Finished articles comprising rectangles of 160 mm×120 mm with rounded corners are cut out.

Example 154

Prepare representative skin cleansing and conditioning articles in the following manner The cleansing component of any one of Examples 1–74 isheated until molten or semi-molten. The skin conditioning composition of any one of examples 75–131 is also heated until molten. The two compositions are then blended together in a ratio of 9:1 cleansing:conditioning composition using an overhead stirrer and then allowed to cool and solidify. The resultant cleansing+conditioning composition is then heated until molten in a tray. A continuous web of batting is fed through the tray such that it becomes impregnated with the molten cleansing+conditioning component. The batting is then nipped between two rollers to remove excess coating and leave a coat weight equivalent to 5.0 grams of cleansing+conditioning component per finished article. The coated batting is cooled to solidify the coated cleansing+conditioning component. The coated batting is then combined with a second apertured non-woven layer. The combined webs are ultrasonically bonded together in a pattern of wavy lines about 1 cm long and spaced 1 cm apart. Finished articles of 12 cm×16 cm are then cut out

What is claimed is:

1. A substantially dry, disposable personal care article suitable for cleansing, said article comprising:
   a) a water insoluble substrate comprising a first creped nonwoven layer; and
   b) a cleansing component disposed adjacent to said water insoluble substrate, wherein said component comprises from about 10% to about 1000%, by weight of the water insoluble substrate, of a lathering surfactant and wherein the cleansing component exhibits a log greater than about 0.45.

2. The article of claim 1 wherein said cleansing component requires minimal to no drying such that said article is substantially dry prior to use.

3. The article of claim 1 wherein said cleansing component exhibits a complex viscosity measured under an oscillation stress of 1 Pa of greater than about 100 Pa·s at 25° C.

4. The article of claim 1 wherein said creped nonwoven layer exhibits a Crepe Ratio of from about 2.5 to about 45.

5. The article of claim 1 wherein said water insoluble substrate comprises at least one additional layer.

6. The article of claim 1 wherein said lathering surfactant is selected from the group consisting of anionic lathering surfactants, nonionic lathering surfactants, cationic lathering surfactants, amphoteric lathering surfactants, and combinations thereof.

7. The article of claim 5 wherein said cleansing component is disposed between said first layer and said additional layer.

8. The article of claim 5 wherein said first layer and said additional layer are spot bonded to one another.

9. The article of claim 1 that further comprises a therapeutic component, disposed adjacent to said water insoluble substrate, wherein said component comprises from about 10% to about 1000%, by weight of the water insoluble substrate, of a therapeutic benefit agent.

10. The article of claim 9 wherein said therapeutic benefit agent is selected from the group consisting of hydrophobic conditioning agents, hydrophilic conditioning agents, and combinations thereof.

11. The article of claim 9 wherein said therapeutic benefit component further comprises a therapeutic benefit agent selected from the group consisting of vitamin compounds, skin treating agents, anti-acne actives, anti-wrinkle actives, anti-skin atrophy actives, anti-inflammatory actives, topical anesthetics, artificial tanning actives and accelerators, anti-microbial actives, anti-fungal actives, anti-viral agents, enzymes, sunscreen actives, anti-oxidants, skin exfoliating agents, and combinations thereof.

12. A method of cleansing the skin and hair, said method comprising the steps of:
   a) wetting the article of claim 1; and
   b) contacting the skin or hair with the wetted article.

13. A method of cleansing and conditioning the skin and hair, said method comprising the steps of:
   a) wetting the article of claim 10; and
   b) contacting the skin and hair with the wetted article.

14. A substantially dry, disposable personal care article suitable for cleansing and conditioning, said article comprising:
   a) a water insoluble substrate comprising a first creped nonwoven layer;
   b) a cleansing component disposed adjacent to said water insoluble substrate, wherein said component comprises from about 10% to about 1000%, by weight of the water insoluble substrate, of a lathering surfactant;
   c) a therapeutic benefit component disposed adjacent to said water insoluble substrate, wherein said component comprises from about 10% to about 1000%, by weight of the water insoluble substrate, of a therapeutic benefit agent;

and wherein the cleansing component exhibits a log [($\eta$ @ 25° C.)/($\eta$ @ 200° C.)] greater than about 0.45 and also exhibits a complex viscosity measured under an oscillation stress of 1 Pa of greater than about 100 Pa·s at 25° C.

15. The article of claim 14 wherein said water insoluble substrate comprises at least one additional layer.

16. The article of claim 14 wherein said creped nonwoven layer exhibits a Crepe Ratio of from about 2.5 to about 4.5.

17. A personal care kit comprising the article of claim 1 and an additional article that comprises a substrate.

18. A personal care kit comprising the article of claim 14 and an additional article that comprises a substrate.

19. A substantially dry, disposable personal care article suitable for cleansing, said article comprising:
  a) a water insoluble substrate comprising a first creped nonwoven layer; and
  b) a cleansing component disposed adjacent to said water insoluble substrate, wherein said component comprises from about 10% to about 1000%, by weight of the water insoluble substrate, of a lathering surfactant and wherein the cleansing component exhibits a log [($\eta$ @ 25° C.)/($\eta$ @ 125° C.)] greater than about 3.

20. A substantially dry, disposable personal care article suitable for cleansing, said article comprising:
  a) a water insoluble substrate comprising a first creped nonwoven layer; and
  b) a cleansing component disposed adjacent to said water insoluble substrate, wherein said component comprises from about 10% to about 1000%, by weight of the water insoluble substrate, of a lathering surfactant and wherein the cleansing component exhibits a log [($\eta$ @ 25° C.)/($\eta$ @ 60° C.)] greater than about 5.

* * * * *